US008846037B2

(12) United States Patent
Rajpal et al.

(10) Patent No.: US 8,846,037 B2
(45) Date of Patent: Sep. 30, 2014

(54) ANTIBODIES TO IL-6 AND THEIR USES

(71) Applicants: Pfizer Inc., New York, NY (US); Bristol-Myers Squibb Company, Princeton, NJ (US)

(72) Inventors: Arvind Rajpal, San Francisco, CA (US); Madhav Narasimha Devalaraja, Gaithersburg, MD (US); Kristopher Toy, San Jose, CA (US); Lan Yang, Morgan Hill, CA (US); Haichun Huang, Fremont, CA (US); Jun Zhang, Tracy, CA (US); Peter Brams, Sacramento, CA (US); Brigitte Devaux, Palo Alto, CA (US); David B. Passmore, San Carlos, CA (US)

(73) Assignees: Pfizer Inc., New York, NY (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/857,867

(22) Filed: Apr. 5, 2013

(65) Prior Publication Data
US 2013/0280266 A1    Oct. 24, 2013

Related U.S. Application Data

(62) Division of application No. 13/454,296, filed on Apr. 24, 2012, now Pat. No. 8,436,158, which is a division of application No. 12/480,991, filed on Jun. 9, 2009, now Pat. No. 8,188,235.

(60) Provisional application No. 61/073,430, filed on Jun. 18, 2008.

(51) Int. Cl.
*A61K 39/395* (2006.01)
*A61K 39/00* (2006.01)
*C07K 16/24* (2006.01)

(52) U.S. Cl.
CPC ......... *C07K 16/248* (2013.01); *C07K 2317/565* (2013.01); *C07K 2317/92* (2013.01); *C07K 2317/567* (2013.01); *C07K 2317/56* (2013.01)
USPC ..................................... 424/130.1; 424/133.1

(58) Field of Classification Search
None
See application file for complete search history.

(56) References Cited

U.S. PATENT DOCUMENTS

| 5,001,116 | A | 3/1991 | Folkman et al. |
|---|---|---|---|
| 5,210,075 | A | 5/1993 | Scholz et al. |
| 5,326,859 | A | 7/1994 | Sugano et al. |
| 5,468,609 | A | 11/1995 | Revel et al. |
| 5,530,101 | A | 6/1996 | Queen et al. |
| 5,554,513 | A | 9/1996 | Revel et al. |
| 5,559,012 | A | 9/1996 | Brailly et al. |
| 5,591,827 | A | 1/1997 | Brakenhoff et al. |
| 5,618,700 | A | 4/1997 | Novick et al. |
| 5,618,920 | A | 4/1997 | Robinson et al. |
| 5,639,455 | A | 6/1997 | Shimamura et al. |
| 5,723,120 | A | 3/1998 | Brakenhoff et al. |
| 5,738,931 | A | 4/1998 | Sato et al. |
| 5,789,552 | A | 8/1998 | Savino et al. |
| 5,807,715 | A | 9/1998 | Morrison et al. |
| 5,817,790 | A | 10/1998 | Tsuchiya et al. |
| 5,849,283 | A | 12/1998 | Ciliberto et al. |
| 5,854,398 | A | 12/1998 | Chang et al. |
| 5,856,135 | A | 1/1999 | Tsuchiya et al. |
| 5,859,205 | A | 1/1999 | Adair et al. |
| 5,871,723 | A | 2/1999 | Strieter et al. |
| 5,888,510 | A | 3/1999 | Kishimoto et al. |
| 5,888,511 | A | 3/1999 | Skurkovich et al. |
| 5,914,106 | A | 6/1999 | Ciliberto et al. |
| 5,942,220 | A | 8/1999 | Warren et al. |
| 5,958,400 | A | 9/1999 | Ruben et al. |
| 5,972,902 | A | 10/1999 | Ciliberto et al. |
| 6,010,864 | A | 1/2000 | Hoeprich, Jr. |
| 6,036,978 | A | 3/2000 | Gombotz et al. |
| 6,086,874 | A | 7/2000 | Yoshida et al. |
| 6,121,423 | A | 9/2000 | Tsuchiya et al. |
| 6,261,560 | B1 | 7/2001 | Tsujinaka et al. |
| 6,461,604 | B1 | 10/2002 | Somers et al. |
| 6,482,411 | B1 | 11/2002 | Ahuja et al. |
| 2001/0001663 | A1 | 5/2001 | Kishimoto et al. |
| 2003/0017150 | A1 | 1/2003 | Torphy |
| 2003/0190316 | A1 | 10/2003 | Kakuta et al. |
| 2004/0028681 | A1 | 2/2004 | Ito et al. |
| 2006/0240012 | A1 | 10/2006 | Sugimura et al. |

(Continued)

FOREIGN PATENT DOCUMENTS

| EP | 0312996 | 4/1989 |
|---|---|---|
| EP | 0326120 | 8/1989 |

(Continued)

OTHER PUBLICATIONS

Neurath, "IL-6 signaling in autoimmunity, chronic inflammation and inflammation-associated cancer" Cytokine & Growth Factor Reviews 22 (2011) 83-89.*
Stefan Rose-John et al. (Expert Opin. Therapeutic. Targets (2007), 11(5): 613-624.*
Kishimoto, "IL-6: from its discovery to clinical applications" International Immunology, 22(5), pp. 347-352.*
Navarro et al. Influence of renal involvement on peripheral blood mononuclear cell expression behaviour of tumor necrosis factor-alpha and interleukin-6 in type 2 diabetic patients (Nephrol Dial Transplant (2008) 23: 919-926.*
Mihara et al. "The therapy of autoimmune diseaes by anti-interleukin-6 receptor antibody" Vaccines & Antibodies, 5(5): pp. 683-690, 2005.*
US 6,008,005, 12/1999, Shiraki et al (withdrawn).

(Continued)

*Primary Examiner* — Daniel E Kolker
*Assistant Examiner* — James Rogers
(74) *Attorney, Agent, or Firm* — Ropes & Gray LLP

(57) ABSTRACT

Antibodies and antigen-binding portions thereof that bind to human IL-6 are provided. Also provided are nucleic acids encoding such antibodies and antigen binding portions, methods of making such antibodies and antigen binding portions, compositions comprising such antibodies or antigen binding portions, and uses of such antibodies or antigen binding portions.

33 Claims, 7 Drawing Sheets

(56) References Cited

U.S. PATENT DOCUMENTS

| | | | |
|---|---|---|---|
| 2006/0246071 | A1 | 11/2006 | Green et al. |
| 2006/0257407 | A1 | 11/2006 | Chen et al. |
| 2007/0178098 | A1 | 8/2007 | Way et al. |
| 2008/0075726 | A1 | 3/2008 | Smith et al. |
| 2009/0022659 | A1 | 1/2009 | Olson et al. |
| 2009/0317402 | A1 | 12/2009 | Rajpal et al. |
| 2012/0202285 | A1 | 8/2012 | Rajpal et al. |

FOREIGN PATENT DOCUMENTS

| | | |
|---|---|---|
| EP | 0399429 | 11/1990 |
| EP | 0410813 | 1/1991 |
| EP | 0430193 | 6/1991 |
| EP | 0572118 | 12/1993 |
| EP | 0617126 | 9/1994 |
| EP | 0783893 | 7/1997 |
| EP | 0800829 | 10/1997 |
| EP | 1074268 | 2/2001 |
| EP | 1108435 | 6/2001 |
| EP | 1536012 | 6/2005 |
| WO | WO-9107986 | 6/1991 |
| WO | WO-9108774 | 6/1991 |
| WO | WO-9409138 | 4/1994 |
| WO | WO-9503036 | 2/1995 |
| WO | WO-9600081 | 1/1996 |
| WO | WO-9913092 | 3/1999 |
| WO | WO-0158956 | 8/2001 |
| WO | WO-02072788 | 9/2002 |
| WO | WO-03083061 | 10/2003 |
| WO | WO-2004039826 | 5/2004 |
| WO | WO-2004045507 | 6/2004 |
| WO | WO-2004071404 | 8/2004 |
| WO | WO-2004096273 | 11/2004 |
| WO | WO-2005005604 | 1/2005 |
| WO | WO-2005028514 | 3/2005 |
| WO | WO 2005/087797 | 9/2005 |
| WO | WO 2006/024694 | 3/2006 |
| WO | WO-2006099875 | 9/2006 |
| WO | WO-2006119115 | 11/2006 |
| WO | WO 2007/067992 | 6/2007 |
| WO | WO-2008019061 | 2/2008 |
| WO | WO-2008/065378 | 6/2008 |
| WO | WO-2008144763 | 11/2008 |

OTHER PUBLICATIONS

Aoki et al., "Angiogenesis and hematopoiesis induced by Kaposi's sarcoma-associated herpesvirus-encoded interleukin-6," Blood, 93(12):4034-4043 (1999).
Baselga et al., "Receptor blockade with monoclonal antibodies as anti-cancer therapy," Pharmaceutical Therapy, 64(1):127-154 (1994).
Bataille et al., "Biologic effects of anti-interleukin-6 murine monoclonal antibody in advanced multiple myeloma," Blood, 86(2):685-691 (1995).
Beiboer et al., "Guided selection of a pan carcinoma specific antibody reveals similar binding characteristics yet structural divergence between the original murine antibody and its human equivalent," Journal of Molecular Biology, 296(3):833-849 (2000).
Blay et al., "Serum level of interleukin 6 as a prognosis factor in metastatic renal cell carcinoma" Cancer Research, 52(12):3317-3322 (1992).
Brakenhoff et al., "Molecular cloning and expression of hybridoma growth factor in *Escherichia coli*," Journal of Immunology, 139(12):4116-4121 (1987).
Brakenhoff et al., "Structure-function analysis of human Il-6. Epitope mapping of neutralizing monoclonal antibodies with amino- and carboxyl-terminal deletion mutants," Journal of Immunology, 145(2):561-568 (1990).
Brown et al., "Tolerance of single, but not multiple, amino acid replacements in antibody VH CDR 2: a means of minimizing B cell wastage from somatic hypermutation?," Journal of Immunology, 156(9):3285-3291 (1996).

Chauhan et al., "SHP2 mediates the protective effect of interleukin-6 against dexamethasone-induced apoptosis in multiple myeloma cells," Journal of Biological Chemistry, 275(36):27845-27850 (2000).
Chien et al., "Significant structural and functional change of an antigen-binding site by a distant amino acid substitution: proposal of a structural mechanism," PNAS, 86(14):5532-5536 (1989).
Cohen et al., "Interleukin 6 induces the expression of vascular endothelial growth factor," Journal of Biological Chemistry, 271(2):736-741 (1996).
Colman, "Effects of Amino Acid Sequence Changes on Antibody-Antigen Interactions," Research in Immunology, 145:33-36 (1994).
Cruse and Lewis, Illustrated Dictionary of Immunology, p. 19, 1995.
Klimka et al., "Human anti-CD30 recombinant antibodies by guided phage antibody selection using cell panning," British Journal of Cancer, 83(2):252-260 (2000).
Liang et al., "Anti-interleukin-6 monoclonal antibody inhibits autoimmune responses in a murine model of systemic lupus erythematosus," Immunology, 119(3):296-305 (2006).
Matsuda et al., "Establishment of an interleukin 6 (IL 6)/B cell stimulatory factor 2-dependent cell line and preparation of anti-IL 6 monoclonal antibodies," European Journal of Immunology, 18(6):951-956 (1988).
Miki et al., "Interleukin-6 (IL-6) functions as an in vitro autocrine growth factor in renal cell carcinomas," FEBS Letters, 250(2):607-610 (1989).
Motro et al., "Pattern of interleukin 6 gene expression in vivo suggests a role for this cytokine in angiogenesis," PNAS, 87(8):3092-3096 (1990).
Naka et al., "The paradigm of IL-6: from basic science to medicine," Arthritis Research, 4(3):S233-S242 (2002).
Padlan, "Anatomy of the Antibody Molecule," Molecular Immunology, 31(3):169-217 (1994).
Paul, "Fv Structure and Diversity in Three Dimensions," Fundamental Immunology, 3rd Edition, pp. 292-295 (1993).
Petrov, "Immunology Reviews", Medicine Publishers, Russian Article and English Translation, Soviet Medical Reviews, Section D, 1:56-58 (1987).
Pourtau et al., "Cyclooxygenase-2 activity is necessary for the angiogenic properties of oncostatin M," FEBS Letters, 459(3):453-457 (1999).
Rudikoff et al., "Single amino acid substitution altering antigen-binding specificity," PNAS, 79(6):1979-1983 (1982).
Sato et al., "Humanization of an anti-human IL-6 mouse monoclonal antibody glycosylated in its heavy chain variable region," Human Antibodies and Hybridomas, 7(4):175-183 (1996).
Sato et al., "Reshaping a human antibody to inhibit the interleukin 6-dependent tumor cell growth," Cancer Research, 53(4):851-856 (1993).
Seideman et al., "A novel monoclonal antibody screening method using the Luminex-100 microsphere system," Journal of Immunological Methods, 267(2):165-171 (2002).
Shimamura et al., "Analysis of interleukin 6 (IL-6)/IL-6 receptor system using monoclonal anti-IL-6 antibodies," Molecular Immunology, 28(11):1155-1161 (1991).
Trikha et al., "Targeted anti-interleukin-6 monoclonal antibody therapy for cancer: a review of the rationale and clinical evidence," Clinical Cancer Research, 9(13:4653-4665 (2003).
Tsunenari et al., "Therapeutic potential of humanized anti-interleukin-6 receptor antibody: antitumor activity in xenograft model of multiple myeloma," Anticancer Research, 16(15A):2537-2544 (1996).
Vajdos et al., "Comprehensive functional maps of the antigen-binding site of an anti-ErbB2 antibody obtained with shotgun scanning mutagenesis," Journal of Molecular Biology, 320(2):415-428 (2002).
Van Zaanen et al., "Blocking interleukin-6 activity with chimeric anti-IL6 monoclonal antibodies in multiple myeloma: effects on soluble IL6 receptor and soluble gp130," Leukemia and Lymphoma, 31(5-6):551-558 (1998).
Van Zaanen et al., "Chimaeric anti-interleukin 6 monoclonal antibodies in the treatment of advanced multiple myeloma: a phase I dose-escalating study," British Journal of Haematology, 102(3):783-790 (1998).

(56) References Cited

OTHER PUBLICATIONS

Van Zaanen et al., "Endogenous interleukin 6 production in multiple myeloma patients treated with chimeric monoclonal anti-IL6 antibodies indicates the existence of a positive feed-back loop," Journal of Clinical Investigations, 98(6):1441-1448 (1996).

Vink et al., "Mouse plasmacytoma growth in vivo: enhancement by interleukin 6 (IL-6) and inhibition by antibodies directed against IL-6 or its receptor," Journal of Experimental Medicine, 172(3):997-1000 (1990).

Wei et al., "Interleukin-6 promotes cervical tumor growth by VEGF-dependent angiogenesis via a STAT3 pathway," Oncogene, 22(10):1517-1527 (2003).

Wendling et al., "Treatment of severe rheumatoid arthritis by anti-interleukin 6 monoclonal antibody," Journal of Rheumatology, 20(2):259-262 (1993).

Pakula et al., "Genetic analysis of protein stability and function," Annu. Rev. Gen., 23:289-310 (1989).

Roitt et al., "Chapter 6: Antibodies and Their Receptors", Immunology, $5^{th}$ ed., Mosby International, Ltd., London, pp. 71-82 (1998).

* cited by examiner

ANTI-IL6 22B5 VH REGION

```
GERMLINE  Q V Q L Q Q W G A G L L K P S E T L S L T C A V Y G G S F S G Y Y W S W I R Q P P
22B5 VH   - - - - - - - - - - - - - - - - - - - - - - - - - - - R - - - - - - - - - - - -

GERMLINE  G K G L E W I G E I N H S G S T N Y N P S L K S R V T I S V D T S K N Q F S L K L
22B5 VH   - - - - - - - - - - - - - - - - - F - - - - - - - - - - - - - - - - - - - - - -

GERMLINE  S S V T A A D T A V Y Y C A R # # # # A F D I W G Q G T M V T V S S    SEQ ID NO:46
22B5 VH   R - - - - - - - - - - - - - - - E D I D D - - - - - - - - - - - - -
```

FIG. 1A

ANTI-IL6 22B5 VK REGION

```
GERMLINE  D I Q M T Q S P S S L S A S V G D R V T I T C R A S Q G I S S W L A W Y Q Q K
22B5 VK2  - - - - - - - - - - - - - - - - - - - - - - - - - - - - - - - - - - - - - -

GERMLINE  P E K A P K S L I Y A A S S L Q S G V P S R F S G S G S G T D F T L T I S S L
22B5 VK2  - - - - - - - - - - - - - - - - - - - - - - - - - - - - - - - - - - - - - -

GERMLINE  Q P E D F A T Y Y C Q Q Y N S Y P W T F G Q G T K V E I K    SEQ ID NO: 47
22B5 VK2  - - - - - - - - - - - - - - K - - - R - - - - - - - - - -
```

FIG. 1B

| ANTI-IL-8 9C8 VH | | | | | | | | | | |
|---|---|---|---|---|---|---|---|---|---|---|
| GERMLINE | Q V Q L Q Q W G A G L L K P S E T L S L T C A V Y G G S F S G Y Y W S W I R Q P |
| 9C8 | . . . . . . . . . . . . . . . . . . I . . . . . . . . . . . . . R E . . . . . . |
| GERMLINE | P G K G L E W I G E I N H S G S T N Y N P S L K S R V T I S V D T S K N Q F S L |
| 9C8 | . . . . . . . . . . . . . . . F . . . . . . . . . . . . . . N . . . . . . . . . |
| GERMLINE | K L S V T A A D T A V Y Y C A R # # # # A R D I W G Q G T M V T V S S |
|         | SEQ ID NO:46 |
| 9C8 | . T . . . . . . . . . . . . . . . E E L D D . . . . . . . . . . . |

FIG. 1C

ANTI-IL-8 9C8 VK

GERMLINE   D I Q M T Q S P S S L S A S V G D R V T I T C R A S Q G I S S W L A W Y Q Q K P
9C8        - - - - - - - - - - - - - - - - - - - - - - - - - - - - - - - - - - - - - - -

GERMLINE   E K A P K S L I Y A A S S L Q S G V P S R F S G S G S G T D F T L T I S S L Q P
9C8        - - - - - - - - - - - - - - - - - - - - - - - - - - - - - - - - - - - - - - -

GERMLINE   E D F A T Y Y C Q Q Y N S Y P W T F G Q G T K V E I K   SEQ ID NO:47
9C8        - - - - - - - - - - - K - - - - - - R - - - - - - - -

FIG. 1D

ANTI-IL6 9C8 N68T, T83S V_H

```
GERMLINE    Q V Q L Q Q W G A G L L K P S E T L S L T C A V Y G G S F S G Y Y W S W I R Q P
9C8N68TT83S - - - - - - - - - - - - - - - - - - - - - - - I - - - - - - - - - R E - - - - -

GERMLINE    P G K G L E W I G E I N H S G S T N Y N P S L K S R V T I S V D T S K N Q F S L
9C8N68TT83S - - - - - - - - - - - - - - - F - - - - - - - - - - - - - - - - - - - - - - -

GERMLINE    K L S S V T A A D T A V Y Y C A R # # # # A F D I W G Q G T M V T V S S
            SEQ ID NO: 46
9C8N68TT83S - - - - - - - - - - - - - - - - - - E E L D D - - - - - - - - - - - -
```

FIG. 1E

ANTI-IL-6 9C8 N68T, T83S Vk

```
GERMLINE   D I Q M T Q S P S S L S A S V G D R V T I T C R A S Q G I S S W L A W Y Q Q K P
9C8N68TT83S  - - - - - - - - - - - - - - - - - - - - - - - - - - - - - - - - - - - - - -

GERMLINE   E K A P K S L I Y A A S S L Q S G V P S R F S G S G S G T D F T L T I S S L Q P
9C8N68TT83S  - - - - - - - - - - - - - - - - - - - - - - - - - - - - - - - - - - - - - -

GERMLINE   E D F A T Y Y C Q Q Y N S Y P W T F G Q G T K V E I K   SEQ ID NO:47
9C8N68TT83S  - - - - - - - - - - - K - - - - - R - - - - - - - - -
```

FIG. 1F

SEQUENCE LISTING

<160> NUMBER OF SEQ ID NOS: 60

<210> SEQ ID NO 1
<211> LENGTH: 1338

```
<212> TYPE: DNA
<213> ORGANISM: homo sapien

<400> SEQUENCE: 1
caggtgcagc tacagcagtg gggcgcagga ctgttgaagc cttcggagac cctgtccctc      60
acctgcgcta tctatggtgg gtccttcagg gagtactact ggagctggat ccgccagccc     120
ccagggaagg ggctggagtg gattggggaa atctttcata gtggaagcac caactacaac     180
ccgtccctca agagtcgagt caacatatca gtagacacgt ccaagaacca gttctccctg     240
aagctgacct ctgtgaccgc cgcggacacg gctgtgtatt actgtgcgag agaggaatta     300
gatgattttg atatctgggg ccaagggaca atggtcaccg tctcttcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338

<210> SEQ ID NO 2
<211> LENGTH: 348
<212> TYPE: DNA
<213> ORGANISM: homo sapien

<400> SEQUENCE: 2
caggtgcagc tacagcagtg gggcgcagga ctgttgaagc cttcggagac cctgtccctc      60
acctgcgcta tctatggtgg gtccttcagg gagtactact ggagctggat ccgccagccc     120
ccagggaagg ggctggagtg gattggggaa atctttcata gtggaagcac caactacaac     180
ccgtccctca agagtcgagt caacatatca gtagacacgt ccaagaacca gttctccctg     240
aagctgacct ctgtgaccgc cgcggacacg gctgtgtatt actgtgcgag agaggaatta     300
gatgattttg atatctgggg ccaagggaca atggtcaccg tctcttca                  348

<210> SEQ ID NO 3
<211> LENGTH: 446
<212> TYPE: PRT
<213> ORGANISM: homo sapien

<400> SEQUENCE: 3
```

-continued

```
Gln Val Gln Leu Gln Gln Trp Gly Ala Gly Leu Leu Lys Pro Ser Glu
  1               5                  10                  15
Thr Leu Ser Leu Thr Cys Ala Ile Tyr Gly Gly Ser Phe Arg Glu Tyr
             20                  25                  30
Tyr Trp Ser Trp Ile Arg Gln Pro Pro Gly Lys Gly Leu Glu Trp Ile
         35                  40                  45
Gly Glu Ile Phe His Ser Gly Ser Thr Asn Tyr Asn Pro Ser Leu Lys
 50                  55                  60
Ser Arg Val Asn Ile Ser Val Asp Thr Ser Lys Asn Gln Phe Ser Leu
 65                  70                  75                  80
Lys Leu Thr Ser Val Thr Ala Ala Asp Thr Ala Val Tyr Tyr Cys Ala
             85                  90                  95
Arg Glu Glu Leu Asp Asp Phe Asp Ile Trp Gly Gln Gly Thr Met Val
        100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
        210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
```

```
                         420                 425                 430
Asn His Tyr Thr Gln Lys Ser Leu Ser Leu Ser Pro Gly Lys
            435                 440                 445

<210> SEQ ID NO 4
<211> LENGTH: 116
<212> TYPE: PRT
<213> ORGANISM: homo sapien

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Arg Glu Tyr
            20                  25                  30

Tyr Trp Ser Trp Ile Arg Gln Pro Pro Gly Lys Gly Leu Glu Trp Ile
        35                  40                  45

Gly Glu Ile Phe His Ser Gly Ser Thr Asn Tyr Asn Pro Ser Leu Lys
    50                  55                  60

Ser Arg Val Asn Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Glu Leu Asp Asp Phe Asp Ile Trp Gly Gln Gly Thr Met Val
            100                 105                 110

Thr Val Ser Ser
        115

<210> SEQ ID NO 5
<211> LENGTH: 5
<212> TYPE: PRT
<213> ORGANISM: homo sapien

<400> SEQUENCE: 5

Glu Tyr Tyr Trp Ser
1               5

<210> SEQ ID NO 6
<211> LENGTH: 16
<212> TYPE: PRT
<213> ORGANISM: homo sapien

<400> SEQUENCE: 6

Glu Ile Phe His Ser Gly Ser Thr Asn Tyr Asn Pro Ser Leu Lys Ser
1               5                   10                  15

<210> SEQ ID NO 7
<211> LENGTH: 8
<212> TYPE: PRT
<213> ORGANISM: homo sapien

<400> SEQUENCE: 7

Glu Glu Leu Asp Asp Phe Asp Ile
1               5

<210> SEQ ID NO 8
<211> LENGTH: 30
<212> TYPE: PRT
<213> ORGANISM: homo sapien

<400> SEQUENCE: 8

Gln Val Gln Leu Gln Gln Trp Gly Ala Gly Leu Leu Lys Pro Ser Glu
```

```
1               5                   10                  15
Thr Leu Ser Leu Thr Cys Ala Ile Tyr Gly Gly Ser Phe Arg
                20                  25                  30
```

<210> SEQ ID NO 9
<211> LENGTH: 14
<212> TYPE: PRT
<213> ORGANISM: homo sapien

<400> SEQUENCE: 9

```
Trp Ile Arg Gln Pro Pro Gly Lys Gly Leu Glu Trp Ile Gly
1               5                   10
```

<210> SEQ ID NO 10
<211> LENGTH: 31
<212> TYPE: PRT
<213> ORGANISM: homo sapien

<400> SEQUENCE: 10

```
Arg Val Asn Ile Ser Val Asp Thr Ser Lys Asn Gln Phe Ser Leu Lys
1               5                   10                  15
Leu Thr Ser Val Thr Ala Ala Asp Thr Ala Val Tyr Tyr Cys Ala
                20                  25                  30
```

<210> SEQ ID NO 11
<211> LENGTH: 11
<212> TYPE: PRT
<213> ORGANISM: homo sapien

<400> SEQUENCE: 11

```
Trp Gly Gln Gly Thr Met Val Thr Val Ser Ser
1               5                   10
```

<210> SEQ ID NO 12
<211> LENGTH: 642
<212> TYPE: DNA
<213> ORGANISM: homo sapien

<400> SEQUENCE: 12

| | | | | | |
|---|---|---|---|---|---|
| gacatccaga | tgacccagtc | tccatcctca | ctgtctgcat | ctgtaggaga | cagagtcacc | 60 |
| atcacttgtc | gggcgagtca | gggtattagc | agctggttag | cctggtatca | gcagaaacca | 120 |
| gagaaagccc | ctaagtccct | gatctatgct | gcatccagtt | tgcaaagtgg | ggtcccatca | 180 |
| aggttcagcg | gcagtggatc | tgggacagat | ttcactctca | ccatcagtag | cctgcagcct | 240 |
| gaagattttg | caacttatta | ctgccaacag | tataaaagtt | accctcggac | gttcggccaa | 300 |
| gggaccaagg | tggaaatcaa | acgaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gt | | 642 |

<210> SEQ ID NO 13
<211> LENGTH: 321
<212> TYPE: DNA
<213> ORGANISM: homo sapien

<400> SEQUENCE: 13

```
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagtag cctgcagcct     240
gaagattttg caacttatta ctgccaacag tataaaagtt accctcggac gttcggccaa     300
gggaccaagg tggaaatcaa a                                                321
```

<210> SEQ ID NO 14
<211> LENGTH: 214
<212> TYPE: PRT
<213> ORGANISM: homo sapien

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 107
<212> TYPE: PRT
<213> ORGANISM: homo sapien

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Tyr Pro Arg
                 85                  90                  95

Thr Phe Gly Gln Gly Thr Lys Val Glu Ile Lys
            100                 105

<210> SEQ ID NO 16
<211> LENGTH: 11
<212> TYPE: PRT
<213> ORGANISM: homo sapien

<400> SEQUENCE: 16

Arg Ala Ser Gln Gly Ile Ser Ser Trp Leu Ala
1               5                   10

<210> SEQ ID NO 17
<211> LENGTH: 7
<212> TYPE: PRT
<213> ORGANISM: homo sapien

<400> SEQUENCE: 17

Ala Ala Ser Ser Leu Gln Ser
1               5

<210> SEQ ID NO 18
<211> LENGTH: 9
<212> TYPE: PRT
<213> ORGANISM: homo sapien

<400> SEQUENCE: 18

Gln Gln Tyr Lys Ser Tyr Pro Arg Thr
1               5

<210> SEQ ID NO 19
<211> LENGTH: 23
<212> TYPE: PRT
<213> ORGANISM: homo sapien

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 20
<211> LENGTH: 15
<212> TYPE: PRT
<213> ORGANISM: homo sapien

<400> SEQUENCE: 20

Trp Tyr Gln Gln Lys Pro Glu Lys Ala Pro Lys Ser Leu Ile Tyr
1               5                   10                  15

<210> SEQ ID NO 21
<211> LENGTH: 32
<212> TYPE: PRT
<213> ORGANISM: homo sapien

<400> SEQUENCE: 21

Gly Val Pro Ser Arg Phe Ser Gly Ser Gly Ser Gly Thr Asp Phe Thr

```
                1               5                  10                 15
          Leu Thr Ile Ser Ser Leu Gln Pro Glu Asp Phe Ala Thr Tyr Tyr Cys
                           20                  25                  30

<210> SEQ ID NO 22
<211> LENGTH: 10
<212> TYPE: PRT
<213> ORGANISM: homo sapien

<400> SEQUENCE: 22

Phe Gly Gln Gly Thr Lys Val Glu Ile Lys
 1               5                  10

<210> SEQ ID NO 23
<211> LENGTH: 1326
<212> TYPE: DNA
<213> ORGANISM: homo sapien

<400> SEQUENCE: 23
caggtgcagc tacagcagtg gggcgcagga ctgttgaagc cttcggagac cctgtccctc      60
acctgcgcta tctatggtgg gtccttcagg gagtactact ggagctggat ccgccagccc     120
ccagggaagg ggctggagtg gattggggaa atctttcata gtggaagcac caactacaac     180
ccgtccctca agagtcgagt caacatatca gtagacacgt ccaagaacca gttctccctg     240
aagctgacct ctgtgaccgc cgcggacacg gctgtgtatt actgtgcgag agaggaatta     300
gatgattttg atatctgggg ccaagggaca atggtcaccg tctcttcagc ctccaccaag     360
ggcccatcgg tcttccccct ggcgccctgc tccaggagca cctccgagag cacagcggcc     420
ctgggctgcc tggtcaagga ctacttcccc gaaccggtga cggtgtcgtg gaactcaggc     480
gctctgacca gcggcgtgca caccttcccg gctgtcctac agtcctcagg actctactcc     540
ctcagcagcg tagtgaccgt gccctccagc aacttcggca cccagaccta cacctgcaac     600
gtagatcaca agcccagcaa caccaaggtg gacaagacag ttgagcgcaa atgttgtgtc     660
gagtgcccac cgtgcccagc accacctgtg gcaggaccgt cagtcttcct cttcccccca     720
aaacccaagg acaccctcat gatctcccgg acccctgagg tcacgtgcgt ggtggtggac     780
gtgagccacg aagaccccga ggtccagttc aactggtacg tggacggcgt ggaggtgcat     840
aatgccaaga caaagccacg ggaggagcag ttcaacagca cgttccgtgt ggtcagcgtc     900
ctcaccgtcg tgcaccagga ctggctgaac ggcaaggagt acaagtgcaa ggtctccaac     960
aaaggcctcc cagcccccat cgagaaaacc atctccaaaa ccaaagggca gccccgagaa    1020
ccacaggtgt acaccctgcc cccatcccgg gaggagatga ccaagaacca ggtcagcctg    1080
acctgcctgg tcaaaggctt ctaccccagc gacatcgccg tggagtggga gagcaatggg    1140
cagccggaga acaactacaa gaccacacct cccatgctgg actccgacgg ctccttcttc    1200
ctctacagca agctcaccgt ggacaagagc aggtggcagc aggggaacgt cttctcatgc    1260
tccgtgatgc atgaggctct gcacaaccac tacacacaga gagcctctc  cctgtctccg   1320 ggtaaa                                                               1326

<210> SEQ ID NO 24
<211> LENGTH: 442
<212> TYPE: PRT
<213> ORGANISM: homo sapien

<400> SEQUENCE: 24

Gln Val Gln Leu Gln Gln Trp Gly Ala Gly Leu Leu Lys Pro Ser Glu
```

```
1               5                   10                  15
Thr Leu Ser Leu Thr Cys Ala Ile Tyr Gly Gly Ser Phe Arg Glu Tyr
                20                  25                  30

Tyr Trp Ser Trp Ile Arg Gln Pro Pro Gly Lys Gly Leu Glu Trp Ile
                35                  40                  45

Gly Glu Ile Phe His Ser Gly Ser Thr Asn Tyr Asn Pro Ser Leu Lys
                50                  55                  60

Ser Arg Val Asn Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Glu Leu Asp Asp Phe Asp Ile Trp Gly Gln Gly Thr Met Val
                100                 105                 110

Thr Val Ser Ser Ala Ser Thr Lys Gly Pro Ser Val Phe Pro Leu Ala
                115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
                180                 185                 190

Gly Thr Gln Thr Tyr Thr Cys Asn Val Asp His Lys Pro Ser Asn Thr
                195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
                260                 265                 270

Tyr Val Asp Gly Val Glu Val His Asn Ala Lys Thr Lys Pro Arg Glu
                275                 280                 285

Glu Gln Phe Asn Ser Thr Phe Arg Val Val Ser Val Leu Thr Val Val
                290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430
```

Gln Lys Ser Leu Ser Leu Ser Pro Gly Lys
        435                 440

<210> SEQ ID NO 25
<211> LENGTH: 642
<212> TYPE: DNA
<213> ORGANISM: homo sapien

<400> SEQUENCE: 25

```
gacatccaga tgacccagtc tccatcctca ctgtctgcat ctgtaggaga cagagtcacc      60
atcacttgtc gggcgagtca gggtattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagtag cctgcagcct    240
gaagattttg caacttatta ctgccaacag tataaaagtt accctcggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac agggagagt gt                         642
```

<210> SEQ ID NO 26
<211> LENGTH: 214
<212> TYPE: PRT
<213> ORGANISM: homo sapien

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

Phe Asn Arg Gly Glu Cys
        210

<210> SEQ ID NO 27
<211> LENGTH: 1326
<212> TYPE: DNA
<213> ORGANISM: homo sapien

<400> SEQUENCE: 27
caggtgcagc tacagcagtg gggcgcagga ctgttgaagc cttcggagac cctgtccctc        60
acctgcgcta tctatggtgg gtccttcagg gagtactact ggagctggat ccgccagccc       120
ccagggaagg ggctggagtg gattgggggaa atctttcata gtggaagcac caactacaac      180
ccgtccctca gagtcgagt caccatatca gtagacacgt ccaagaacca gttctccctg        240
aagctgagct ctgtgaccgc cgcggacacg gctgtgtatt actgtgcgag agaggaatta       300
gatgattttg atatctgggg ccaagggaca atggtcaccg tctcctcagc ctccaccaag       360
ggcccatcgg tcttccccct ggcgccctgc tccaggagca cctccgagag cacagcggcc       420
ctgggctgcc tggtcaagga ctacttcccc gaaccggtga cggtgtcgtg gaactcaggc       480
gctctgacca gcggcgtgca caccttcccg gctgtcctac agtcctcagg actctactcc       540
ctcagcagcg tagtgaccgt gccctccagc aacttcggca cccagaccta cacctgcaac       600
gtagatcaca agcccagcaa caccaaggtg gacaagacag ttgagcgcaa atgttgtgtc       660
gagtgcccac cgtgcccagc accacctgtg gcaggaccgt cagtcttcct cttccccccca      720 aaacccaagg acaccctcat gatctcccgg acccctgagg tcacgtgcgt ggtggtggac       780
gtgagccacg aagaccccga ggtccagttc aactggtacg tggacggcgt ggaggtgcat       840
aatgccaaga caaagccacg ggaggagcag ttcaacagca cgttccgtgt ggtcagcgtc       900
ctcaccgtcg tgcaccagga ctggctgaac ggcaaggagt acaagtgcaa ggtctccaac       960
aaaggcctcc cagcccccat cgagaaaacc atctccaaaa ccaaagggca gccccgagaa      1020
ccacaggtgt acaccctgcc cccatcccgg gaggagatga ccaagaacca ggtcagcctg      1080
acctgcctgg tcaaaggctt ctaccccagc gacatcgccg tggagtggga gagcaatggg      1140
cagccggaga caactacaa gaccacacct cccatgctgg actccgacgg ctccttcttc       1200
ctctacagca agctcaccgt ggacaagagc aggtggcagc aggggaacgt cttctcatgc      1260
tccgtgatgc atgaggctct gcacaaccac tacacgcaga agagcctctc cctgtctccg      1320
ggtaaa                                                                 1326

<210> SEQ ID NO 28
<211> LENGTH: 442
<212> TYPE: PRT
<213> ORGANISM: homo sapien

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Arg Glu Tyr
            20                  25                  30

Tyr Trp Ser Trp Ile Arg Gln Pro Pro Gly Lys Gly Leu Glu Trp Ile
        35                  40                  45

Gly Glu Ile Phe His Ser Gly Ser Thr Asn Tyr Asn Pro Ser Leu Lys
    50                  55                  60

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Glu Leu Asp Asp Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 29
<211> LENGTH: 116
<212> TYPE: PRT
<213> ORGANISM: homo sapien

<400> SEQUENCE: 29
```

```
Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Arg Glu Tyr
            20                  25                  30

Tyr Trp Ser Trp Ile Arg Gln Pro Pro Gly Lys Gly Leu Glu Trp Ile
            35                  40                  45

Gly Glu Ile Phe His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Glu Leu Asp Asp Phe Asp Ile Trp Gly Gln Gly Thr Met Val
            100                 105                 110

Thr Val Ser Ser
        115

<210> SEQ ID NO 30
<211> LENGTH: 32
<212> TYPE: PRT
<213> ORGANISM: homo sapien

<400> SEQUENCE: 30

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 31
<211> LENGTH: 1338
<212> TYPE: DNA
<213> ORGANISM: homo sapien

<400> SEQUENCE: 31
caggtgcagc tacagcagtg gggcgcagga ctgttgaagc cttcggagac cctgtccctc    60
acctgcgcta tctatggtgg gtccttcagg agtactact  ggagctggat ccgccagccc   120
ccagggaagg gctggagtg gattggggaa atctttcata gtggaagcac caactacaac   180
ccgtccctca gagtcgagt caccatatca gtagacacgt ccaagaacca gttctccctg   240
aagctgagct ctgtgaccgc cgcggacacg gctgtgtatt actgtgcgag agaggaatta   300
gatgattttg atatctgggg ccaagggaca atggtcaccg tctcctcagc tccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg aactcaggc   480
gccctgacca gcggcgtgca caccttcccg gctgtcctac agtcctcagg actctactcc   540
ctcagcagcg tagtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
```

```
aaggtctcca acaaagccct cccagccccc atcgagaaaa ccatctccaa agccaaaggg    1020
cagccccgag aaccacaggt gtacaccctg ccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctatag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 32
<211> LENGTH: 446
<212> TYPE: PRT
<213> ORGANISM: homo sapien

<400> SEQUENCE: 32

```
Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Arg Glu Tyr
            20                  25                  30

Tyr Trp Ser Trp Ile Arg Gln Pro Pro Gly Lys Gly Leu Glu Trp Ile
        35                  40                  45

Gly Glu Ile Phe His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Glu Leu Asp Asp Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
            435                 440                 445

<210> SEQ ID NO 33
<211> LENGTH: 348
<212> TYPE: DNA
<213> ORGANISM: homo sapien

<400> SEQUENCE: 33
caggtgcagc tacagcagtg gggcgcagga ctgttgaagc cttcggagac cctgtccctc     60
acctgcgcta tctatggtgg gtccttcagg gggtactact ggagctggat ccgccagccc    120
ccagggaagg ggctggagtg gattggggaa atctttcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag agaggaatta    300
gatgattttg atatctgggg ccaagggaca atggtcaccg tctcctca                 348

<210> SEQ ID NO 34
<211> LENGTH: 116
<212> TYPE: PRT
<213> ORGANISM: homo sapien

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Arg Gly Tyr
            20                  25                  30

Tyr Trp Ser Trp Ile Arg Gln Pro Pro Gly Lys Gly Leu Glu Trp Ile
        35                  40                  45

Gly Glu Ile Phe His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Glu Glu Leu Asp Asp Phe Asp Ile Trp Gly Gln Gly Thr Met Val
        100                 105                 110

Thr Val Ser Ser
            115

<210> SEQ ID NO 35
<211> LENGTH: 5
<212> TYPE: PRT
<213> ORGANISM: homo sapien

<400> SEQUENCE: 35

Gly Tyr Tyr Trp Ser
1               5

<210> SEQ ID NO 36
<211> LENGTH: 348
<212> TYPE: DNA
<213> ORGANISM: homo sapien

<400> SEQUENCE: 36
caggtgcagc tacagcagtg gggcgcagga ctgttgaagc cttcggagac cctgtccctc     60
acctgcgctg tctatggtgg gtccttcagg gagtactact ggagctggat ccgccagccc    120
ccagggaagg gctggagtg gattggggaa atctttcata gtggaagcac caactacaac     180
ccgtccctca agagtcgagt caccatatca gtagacacgt ccaagaacca gttctccctg    240
aagctgagct ctgtgaccgc cgcggacacg gctgtgtatt actgtgcgag agaggaatta    300
gatgattttg atatctgggg ccaagggaca atggtcaccg tctcctca                 348

<210> SEQ ID NO 37
<211> LENGTH: 116
<212> TYPE: PRT
<213> ORGANISM: homo sapien

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Glu Tyr
                20                  25                  30

Tyr Trp Ser Trp Ile Arg Gln Pro Pro Gly Lys Gly Leu Glu Trp Ile
            35                  40                  45

Gly Glu Ile Phe His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Glu Leu Asp Asp Phe Asp Ile Trp Gly Gln Gly Thr Met Val
            100                 105                 110

Thr Val Ser Ser
        115

<210> SEQ ID NO 38
<211> LENGTH: 30
<212> TYPE: PRT
<213> ORGANISM: homo sapien

<400> SEQUENCE: 38

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg
                20                  25                  30

<210> SEQ ID NO 39

<211> LENGTH: 348
<212> TYPE: DNA
<213> ORGANISM: homo sapien

<400> SEQUENCE: 39

```
caggtgcagc tacagcagtg gggcgcagga ctgttgaagc cttcggagac cctgtccctc    60
acctgcgctg tctatggtgg gtcattcaga ggttactact ggagctggat ccgccagccc   120
ccaggaaagg gactggagtg gattggggaa atctttcata gtggaagcac caactacaac   180
ccgtccctca agagtcgagt caccatatca gtagacacgt ccaagaacca gttctccctg   240
aaactgaggt ctgtgaccgc cgcggacacg gctgtgtatt actgtgcgag agaagatatt   300
gatgattttg atatctgggg ccaagggaca atggtcaccg tctcttca                348
```

<210> SEQ ID NO 40
<211> LENGTH: 116
<212> TYPE: PRT
<213> ORGANISM: homo sapien

<400> SEQUENCE: 40

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Arg Gly Tyr
            20                  25                  30
Tyr Trp Ser Trp Ile Arg Gln Pro Pro Gly Lys Gly Leu Glu Trp Ile
        35                  40                  45
Gly Glu Ile Phe His Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Arg Ser Val Thr Ala Ala Asp Thr Ala Val Tyr Tyr Cys Ala
                85                  90                  95
Arg Glu Asp Ile Asp Asp Phe Asp Ile Trp Gly Gln Gly Thr Met Val
            100                 105                 110
Thr Val Ser Ser
        115
```

<210> SEQ ID NO 41
<211> LENGTH: 8
<212> TYPE: PRT
<213> ORGANISM: homo sapien

<400> SEQUENCE: 41

```
Glu Asp Ile Asp Asp Phe Asp Ile
1               5
```

<210> SEQ ID NO 42
<211> LENGTH: 321
<212> TYPE: DNA
<213> ORGANISM: homo sapien

<400> SEQUENCE: 42

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagactttg caacttatta ttgccaacag tataagagtt accctcggac gttcggccaa   300
```
gggaccaagg tggaaatcaa a                                           321

<210> SEQ ID NO 43
<211> LENGTH: 107
<212> TYPE: PRT
<213> ORGANISM: homo sapien

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Arg
                85                  90                  95

Thr Phe Gly Gln Gly Thr Lys Val Glu Ile Lys
            100                 105

<210> SEQ ID NO 44
<211> LENGTH: 9
<212> TYPE: PRT
<213> ORGANISM: homo sapien
<220> FEATURE:
<221> NAME/KEY: MISC_FEATURE
<222> LOCATION: (2)..()
<223> OTHER INFORMATION: X = D, E, N, or Q
<220> FEATURE:
<221> NAME/KEY: MISC_FEATURE
<222> LOCATION: (2)..(2)
<223> OTHER INFORMATION: X = D, E, N, or Q
<220> FEATURE:
<221> NAME/KEY: MISC_FEATURE
<222> LOCATION: (3)..(3)
<223> OTHER INFORMATION: X = I, L, V, or M

<400> SEQUENCE: 44

Glu Xaa Xaa Leu Asp Asp Phe Asp Ile
1               5

<210> SEQ ID NO 45
<211> LENGTH: 9
<212> TYPE: PRT
<213> ORGANISM: homo sapien
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (3)..(3)
<223> OTHER INFORMATION: X = I or L

<400> SEQUENCE: 45

Glu Xaa Xaa Leu Asp Asp Phe Asp Ile
1               5

<210> SEQ ID NO 46
<211> LENGTH: 112
<212> TYPE: PRT
<213> ORGANISM: homo sapien

<400> SEQUENCE: 46

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Phe Asp Ile Trp Gly Gln Gly Thr Met Val Thr Val Ser Ser
            100                 105                 110

<210> SEQ ID NO 47
<211> LENGTH: 107
<212> TYPE: PRT
<213> ORGANISM: homo sapien

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 48
<211> LENGTH: 212
<212> TYPE: PRT
<213> ORGANISM: homo sapien

<400> SEQUENCE: 48

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu

```
              100                 105                 110
Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 49
<211> LENGTH: 25
<212> TYPE: DNA
<213> ORGANISM: Artificial Sequence
<220> FEATURE:
<223> OTHER INFORMATION: sequencing primer

<400> SEQUENCE: 49
ctttctgaga stcmtggakc tcmtg                                      25

<210> SEQ ID NO 50
<211> LENGTH: 20
<212> TYPE: DNA
<213> ORGANISM: Artificial Sequence
<220> FEATURE:
<223> OTHER INFORMATION: sequencing primer

<400> SEQUENCE: 50
tacgtgccaa gcatcctcgc                                            20

<210> SEQ ID NO 51
<211> LENGTH: 26
<212> TYPE: DNA
<213> ORGANISM: Artificial Sequence
<220> FEATURE:
<223> OTHER INFORMATION: sequencing primer

<400> SEQUENCE: 51
gsartcagwc ycwvycagga cacagc                                     26

<210> SEQ ID NO 52
<211> LENGTH: 23
<212> TYPE: DNA
<213> ORGANISM: Artificial Sequence
<220> FEATURE:
<223> OTHER INFORMATION: sequencing primer

<400> SEQUENCE: 52
aggctggaac tgaggagcag gtg                                        23

<210> SEQ ID NO 53
<211> LENGTH: 39
<212> TYPE: DNA
<213> ORGANISM: Artificial Sequence
<220> FEATURE:
<223> OTHER INFORMATION: cloning primer
```

<400> SEQUENCE: 53
ttacagtgcg cgcactccca ggtgcagcta cagcagtgg                    39

<210> SEQ ID NO 54
<211> LENGTH: 39
<212> TYPE: DNA
<213> ORGANISM: Artificial Sequence
<220> FEATURE:
<223> OTHER INFORMATION: cloning primer

<400> SEQUENCE: 54
ttacagtgtg cactccgaca tccagatgac ccagtctcc                    39

<210> SEQ ID NO 55
<211> LENGTH: 20
<212> TYPE: DNA
<213> ORGANISM: Artificial Sequence
<220> FEATURE:
<223> OTHER INFORMATION: cloning primer

<400> SEQUENCE: 55
gaagaccgat gggcccttgg                                         20

<210> SEQ ID NO 56
<211> LENGTH: 51
<212> TYPE: DNA
<213> ORGANISM: Artificial Sequence
<220> FEATURE:
<223> OTHER INFORMATION: cloning primer

<400> SEQUENCE: 56
tatattcctt aattaagtta ttctactcac gtttgatttc caccttggtc c      51

<210> SEQ ID NO 57
<211> LENGTH: 28
<212> TYPE: DNA
<213> ORGANISM: Artificial Sequence
<220> FEATURE:
<223> OTHER INFORMATION: mutagenesis primer

<400> SEQUENCE: 57
cctcacctgc gctgtctatg gtgggtcc                                28

<210> SEQ ID NO 58
<211> LENGTH: 29
<212> TYPE: DNA
<213> ORGANISM: Artificial Sequence
<220> FEATURE:
<223> OTHER INFORMATION: mutagenesis primer

<400> SEQUENCE: 58
gggtccttca gggggtacta ctggagctg                               29

<210> SEQ ID NO 59
<211> LENGTH: 34
<212> TYPE: DNA
<213> ORGANISM: Artificial Sequence
<220> FEATURE:
<223> OTHER INFORMATION: mutagensis primer

<400> SEQUENCE: 59
cctcaagagt cgagtcacca tatcagtaga cacg                         34

<210> SEQ ID NO 60
<211> LENGTH: 28

```
<212> TYPE: DNA
<213> ORGANISM: Artificial Sequence
<220> FEATURE:
<223> OTHER INFORMATION: mutagenesis primer

<400> SEQUENCE: 60
ctccctgaag ctgagctctg tgaccgcc                                              28
```

ANTIBODIES TO IL-6 AND THEIR USES

CROSS-REFERENCE TO RELATED PATENTS AND PATENT APPLICATIONS

This application is a divisional application of U.S. patent application Ser. No. 13/454,296, filed Apr. 24, 2012, which is a divisional application of U.S. patent application Ser. No. 12/480,991, filed Jun. 9, 2009 and issued as U.S. Pat. No. 8,188,235 on May 29, 2012, which claims the benefit of U.S. Provisional Patent Application Ser. No. 61/073,430 filed Jun. 18, 2008. The disclosures of all of the aforementioned priority applications are incorporated herein by reference in their entirety.

The instant application contains a Sequence Listing that has been submitted in ASCII format via EFS-Web and is hereby incorporated by reference in its entirety. Said ASCII file, created on Mar. 25, 2013, is named PCFC-596-103-Sequence-Listing.txt and is 50,074 bytes in size.

JOINT RESEARCH AGREEMENT

The disclosure and claims herein were made as a result of activities undertaken within the scope of a joint research agreement in effect on or before the date the claimed invention was made between Pfizer Inc. and Medarex, Inc.

BACKGROUND

This invention relates to antibodies and antigen-binding portions thereof that bind to human IL-6. This invention also relates to nucleic acids encoding such antibodies and antigen binding portions thereof; methods of making such antibodies and antigen binding portions thereof; compositions comprising such antibodies or antigen binding portions thereof; and uses of such antibodies or antigen binding portions thereof.

Interleukin-6 (IL-6), which is also known as interferon B2 (IFNB2), is a pleiotropic cytokine that belongs to the family of gp130 ligands and is produced by many cell types, including T lymphocytes, fibroblasts and monocytes. IL-6 is produced constitutively at low levels and is readily induced by infectious stimuli or inflammatory cytokines. IL-6 binds to a specific receptor IL-6R (gp80) which heterodimerizes with cell-bound or soluble gp130 to form a functional receptor complex. Binding of IL-6 to its receptor initiates cellular events including activation of the JAK-STAT3 pathway and ras-mediated MAP kinase signaling. IL-6 can elicit a diverse array of effects such as proliferation and differentiation of B cells and monocytes, T cell activation, hematopoiesis, osteoclast activation, keratinocyte growth, neuronal growth, hepatocyte activation and acute phase protein induction from hepatocytes.

IL-6 plays an important role in B cell abnormalities as demonstrated in systemic lupus erythematosus, multiple myeloma and lymphoproliferative disorders. Similarly, IL-6 is also implicated in the pathogenesis of autoimmune and inflammatory diseases such as rheumatoid arthritis and osteoarthritis. Recently, indirect evidence suggests an association between IL-6 and chronic obstructive pulmonary disease and insulin resistance in type 2 diabetes. IL-6 has both pro-inflammatory and anti-inflammatory effects in the immune system, indicating that this cytokine likely plays a central role in regulating the physiological response to disease. Therefore, targeting IL-6 can potentially provide therapeutic benefit in a variety of disease areas.

An increase in the production of IL-6 has been observed in a number of diseases including: Alzheimer's disease, autoimmune diseases, such as rheumatoid arthritis, inflammation, myocardial infarction, Paget's disease, osteoporosis, liver fibrosis, solid tumors (renal cell carcinoma), prostatic and bladder cancers, neurological cancers, and B-cell malignancies (e.g., Casteleman's disease, certain lymphomas, chronic lymphocytic leukemia, and multiple myeloma). Research has indicated that IL-6 is linked to the pathogenesis of many of these diseases, particularly, cancer and rheumatoid arthritis and, therefore, blocking IL-6 should translate into clinical benefits.

SUMMARY

An isolated antibody or antigen-binding portion thereof that specifically binds IL-6 and may act as an IL-6 receptor antagonist, and compositions comprising the antibody or portion are produced.

Compositions comprising (i) the heavy and/or light chain, the variable domains thereof, or antigen-binding portions thereof, of the anti-IL-6 antibody, or nucleic acid molecules encoding them; and (ii) a pharmaceutically acceptable carrier are provided. The compositions may further comprise another component, such as a therapeutic agent or a diagnostic agent.

Diagnostic and therapeutic methods are also provided. Similarly, the anti-IL-6 antibodies and antigen-binding portions thereof are provided for the manufacture of medicaments to treat inflammatory and non-inflammatory disorders.

Vectors and host cells comprising the nucleic acid molecules, as well as methods of recombinantly producing the polypeptides encoded by the nucleic acid molecules are provided.

BRIEF DESCRIPTION OF THE DRAWINGS

FIG. 1 shows an alignment of the germline amino acid sequences of the heavy and light chain variable regions compared to the respective anti-IL-6 antibodies 9C8, 9C8 N68T T83S and 22B5 heavy and light chain variable regions (only mismatches are shown for the 9C8, 9C8 N68T T83S, and 22B5 antibody). FIG. 1A shows the heavy chain variable region of the 22B5 antibody. FIG. 1B shows the light chain variable region of the 22B5 antibody. FIG. 1C shows the heavy chain variable region of the 9C8 antibody. FIG. 1D shows the light chain variable region of the 9C8 antibody. FIG. 1E shows the heavy chain variable region of the 9C8 N68T T83S antibody. FIG. 1F shows the light chain variable region of the 9C8 N68T T83S antibody. The CDRs are underlined and mismatched gap(s) are indicated by a pound sign (#).

DETAILED DESCRIPTION

Definitions and General Techniques

Figure 2:
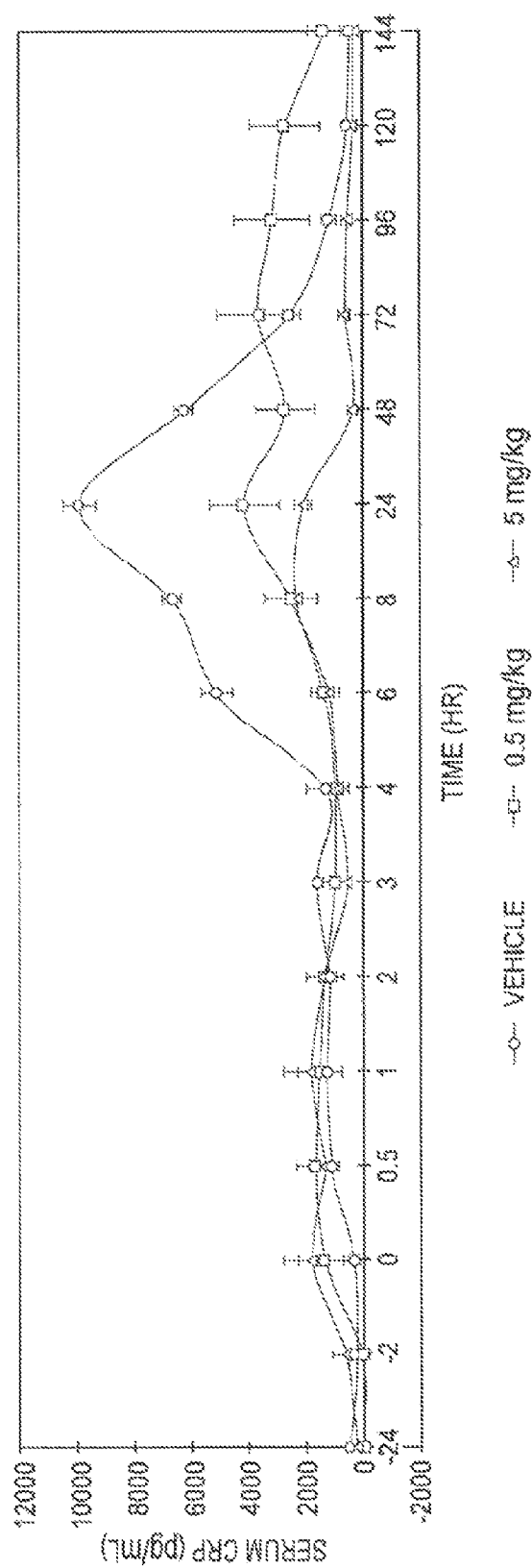
FIG. 2 shows the total serum C-reactive protein (CRP) for the vehicle and the 9C8 N68T T83S IgG$_2$ antibody as determined by Electrochemiluminescence Immuno-Assay. Each point represents an average value of serum CRP from 3 cynomolgus monkeys (±SE) dosed with vehicle or anti-IL-6 antibody 9C8 N68T T83S IgG$_2$ at 0.5 mg/kg and 5.0 mg/kg. Serum CRP was measured by Meso Scale Discovery (MSD). LPS was administered at the 0 hour time point.

The term "antibody" is synonymous with immunoglobulin and is to be understood as commonly known in the art. In particular, the term antibody is not limited by any particular method of producing the antibody. For example, the term antibody includes, inter alia, recombinant antibodies, monoclonal antibodies, and polyclonal antibodies.

The basic antibody structural unit is a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 120 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids.

The variable regions of each heavy/light chain pair ($V_H$ and $V_L$), respectively, form the antigen binding site. Thus, an intact IgG antibody, for example, has two binding sites. Except in bifunctional or bispecific antibodies, the two binding sites are the same.

The variable regions of the heavy and light chains exhibit the same general structure of relatively conserved framework regions (FR) joined by three hyper variable regions, also called complementary determining regions or CDRs. The term "variable" refers to the fact that certain portions of the variable domains differ extensively in sequence among antibodies and are used in the binding and specificity of each particular antibody for its particular antigen. The variability, however, is not evenly distributed throughout the variable domains of antibodies, but is concentrated in the CDRs, which are separated by the more highly conserved FRs. The CDRs from the two chains of each pair are aligned by the FRs, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. *Nature* 342:878-883 (1989), the disclosures of which are herein incorporated by reference.

As used herein, an antibody that is referred to by number is the same as a monoclonal antibody that is obtained from the hybridoma of the same number. For example, anti-IL-6 monoclonal antibody 9C8 is the same antibody as one obtained from hybridoma 9C8, or a subclone thereof.

The term "analog" or "polypeptide analog" means a polypeptide that comprises a segment that has substantial identity to some reference amino acid sequence and has substantially the same function or activity as the reference amino acid sequence. Typically, polypeptide analogs comprise one or more conservative amino acid substitution (or insertion or deletion) with respect to the reference sequence. Analogs can be at least 20 or 25 amino acids long, or can be at least 50, 60, 70, 80, 90, 100, 150 or 200 amino acids long or longer, and can often be as long as the full-length polypeptide. Some embodiments include polypeptide analogs with 1, 2, 3, 4, 5, 6, 7, 8, 9, 10, 11, 12, 13, 14, 15, 16 or 17 substitutions from the reference amino acid sequence. In some instances, the reference amino acid sequence is a germline sequence. Analogs of antibodies or immunoglobulin molecules can be readily prepared by those of ordinary skill in the art.

As discussed herein, amino acid substitutions to an IL-6 antibody or antigen-binding portion thereof are those which typically: (1) reduce susceptibility to proteolysis, (2) reduce susceptibility to oxidation, (3) alter binding affinity for forming protein complexes, (4) delete or create a site for glycosylation, or (4) confer or modify other physicochemical or functional properties of such analogs, but still retain specific binding to IL-6.

Analogs can include various substitutions to the normally-occurring peptide sequence. For example, single or multiple amino acid substitutions, preferably conservative amino acid substitutions, may be made in the normally-occurring sequence. A conservative amino acid substitution typically does not substantially change the structural characteristics of the parent sequence.

The term "antigen-binding portion" of an antibody refers to a fragment of an antibody that retains the ability to specifically bind to an antigen (e.g., IL-6). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a domain antibody, (dAb) (Ward et al., (1989) Nature 341:544-546), which consists of a $V_H$ domain; and (vi) an isolated complementary determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. In addition, one or more CDRs from an antibody may be incorporated into a larger polypeptide chain, which can be covalently or non-covalently linked to another. In embodiments having one or more binding sites, the binding sites may be identical to one another or may be different.

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule and use of a cysteine residue, a marker peptide and a C-terminal polyhistidine tag to make bivalent and biotinylated scFv molecules. Other examples include where one or more CDRs from an antibody are incorporated into a molecule either covalently or noncovalently to make it an immunoadhesin that specifically binds to an antigen of interest, such as IL-6. In such embodiments, the CDR(s) may be incorporated as part of a larger polypeptide chain, may be covalently linked to another polypeptide chain, or may be incorporated noncovalently. Antibody portions, such as Fab and F(ab')$_2$ fragments, can be prepared from whole antibodies using any suitable technique, such as papain or pepsin digestion, respectively, of whole antibodies. Moreover, antibodies, antibody portions and immunoadhesion molecules can be obtained using various recombinant DNA techniques.

The term "chimeric antibody" means an antibody that comprises regions from two or more different antibodies, including antibodies from different species. For example, one or more of the CDRs of a chimeric antibody can be derived from a human IL-6 antibody. In one example, the CDRs from a human antibody can be combined with CDRs from a non-human antibody, such as mouse or rat. In another example, all of the CDRs can be derived from human IL-6 antibodies. In another example, the CDRs from more than one human IL-6 antibody can be combined in a chimeric antibody. For instance, a chimeric antibody may comprise a CDR1 from the light chain of a first human IL-6 antibody, a CDR2 from the light chain of a second human IL-6 antibody and a CDR3 from the light chain of a third human IL-6 antibody, and CDRs from the heavy chain may be derived from one or more other IL-6 antibodies. Further, the framework regions may be derived from one of the IL-6 antibodies from which one or more of the CDRs are taken or from one or more different human antibodies. Further, the term "chimeric antibody" is intended to encompass any of the above mentioned combinations where the combinations involved human and non-human antibodies.

The term "compete" means that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies can be useful for the methods disclosed herein.

The term "conservative amino acid substitution" means an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups can be, for example, valine-leucine-isoleucine, phenylalanine-tyrosine, lysine-arginine, alanine-valine, glutamate-aspartate, and asparagine-glutamine.

A conservative replacement is also any change having a positive value in the PAM250 log-likelihood matrix disclosed in Gonnet et al., Science 256:1443-45 (1992), incorporated herein by reference. A "moderately conservative" replacement is any change having a non-negative value in the PAM250 log-likelihood matrix.

"Contacting" refers to bringing an antibody or antigen binding portion thereof and a target IL-6, or epitope thereof, together in such a manner that the antibody can affect the biological activity of the IL-6. Such "contacting" can be accomplished in vitro, e.g., in a test tube, a petri dish, or the like. In a test tube, contacting may involve only an antibody or antigen binding portion thereof and IL-6 or epitope thereof or it may involve whole cells. Cells may also be maintained or grown in cell culture dishes and contacted with antibodies or antigen binding portions thereof in that environment. In this context, the ability of a particular antibody or antigen binding portion thereof to affect an IL-6 related disorder, i.e., the $IC_{50}$ of the antibody, can be determined before use of the antibody in vivo with more complex living organisms. For cells outside the organism, multiple methods exist, and are well-known to those skilled in the art, to contact IL-6 with the antibodies or antigen-binding portions thereof.

The term "ELISA" refers to an enzyme-linked immunosorbent assay. This kind of assay is well known to those of skill in the art.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, antibodies to that epitope can be generated. An approach to achieve this is to conduct cross-competition studies to find antibodies that competitively bind with one another, i.e., the antibodies compete for binding to the antigen. A high throughput process for "binning" antibodies based upon their cross-competition is described in International Patent Publication No. WO 03/48731.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "germline" refers to the nucleotide sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation.

The term "human antibody" means any antibody in which the variable and constant domain sequences are human sequences. The term encompasses antibodies with sequences derived from human genes, including those which have been changed, e.g., to decrease possible immunogenicity, increase affinity, eliminate cysteine residues that might cause undesirable folding, etc. The term also encompasses such antibodies produced recombinantly in non-human cells, which might impart glycosylation not typical of human cells. These antibodies may be prepared in a variety of ways.

The term "humanized antibody" refers to antibodies of non-human origin, wherein the amino acid residues that are characteristic of antibody sequences of the non-human species are replaced with residues found in the corresponding positions of human antibodies. This "humanization" process can reduce the immunogenicity in humans of the resulting antibody. Antibodies of non-human origin can be humanized using any suitable technique well known in the art. The antibody of interest may be engineered by recombinant DNA techniques to substitute the CH1, CH2, CH3, hinge domains, and/or the framework domain with the corresponding human sequence. The term "humanized antibody" further includes within its meaning, chimeric human antibodies and CDR-grafted antibodies. Chimeric human antibodies include the $V_H$ and $V_L$ of an antibody of a non-human species and the $C_H$ and $C_L$ domains of a human antibody. The CDR-transplanted antibodies result from the replacement of CDRs of the $V_H$ and $V_L$ of a human antibody with those of the $V_H$ and $V_L$, respectively, of an antibody of an animal other than a human.

The term "isolated polynucleotide" as used herein means a polynucleotide of genomic, cDNA, or synthetic origin or a combination thereof, which by virtue of its origin the "isolated polynucleotide" (1) is not associated with all or a portion of polynucleotides with which the "isolated polynucleotide" is found in nature, (2) is operably linked to a polynucleotide to which it is not linked in nature, or (3) does not occur in nature as part of a larger sequence.

The term "isolated protein", "isolated polypeptide" or "isolated antibody" is a protein, polypeptide or antibody that by virtue of its origin or source of derivation: (1) is not associated with naturally associated components that accompany it in its native state; (2) is free of other proteins from the same species; (3) is expressed by a cell from a different species; or (4) does not occur in nature. Thus, a polypeptide that is, e.g., chemically synthesized or synthesized in a cellular system different from the cell from which it naturally originates will be "isolated" from its naturally associated components. A protein may also be rendered substantially free of naturally associated components by isolation, using any suitable protein purification technique.

Examples of isolated antibodies include an IL-6 antibody that has been affinity purified using IL-6, and an IL-6 antibody that has been synthesized by a cell line in vitro.

The term "$K_D$" refers to the binding affinity equilibrium constant of a particular antibody-antigen interaction. An antibody is said to specifically bind an antigen when the $K_D$ is ≤1 mM, preferably ≤100 nM, and most preferably ≤10 nM. A $K_D$ binding affinity constant can be measured by surface plasmon resonance, for example using the BIACORE™ system as discussed in EXAMPLE 7.

The term "$k_{off}$" refers to the dissociation rate constant of a particular antibody-antigen interaction. A $k_{off}$ dissociation rate constant can be measured by surface plasmon resonance, for example using the BIACORE™ system as discussed in EXAMPLE 7.

The term "naturally occurring nucleotides" as used herein includes deoxyribonucleotides and ribonucleotides. The term "modified nucleotides" as used herein includes, for example, nucleotides with modified or substituted sugar groups. The term "oligonucleotide linkages" referred to herein includes oligonucleotide linkages such as, for example, phosphorothioate, phosphorodithioate, phosphoroselenoate, phosphorodiselenoate, phosphoroanilothioate, phoshoraniladate, phosphoroamidate. An oligonucleotide can include a label for detection, if desired.

"Operably linked" sequences include both expression control sequences that are contiguous with the gene of interest and expression control sequences that act in trans or at a distance to control the gene of interest.

The term "percent sequence identity" in the context of nucleic acid sequences means the residues in two sequences that are the same when aligned for maximum correspondence. The length of sequence identity comparison may be over at least about nine nucleotides, usually at least about 18 nucleotides, more usually at least about 24 nucleotides, typically at least about 28 nucleotides, more typically at least about 32 nucleotides, and at least about 36, 48 or more nucleotides. There are a number of different algorithms known in the art which can be used to measure nucleotide sequence identity. For instance, polynucleotide sequences can be compared using FASTA, Gap or Besffit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); incorporated herein by reference). Default parameters for a particular program or algorithm are typically used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

The term "percent sequence identity" in the context of amino acid sequences means the residues in two sequences that are the same when aligned for maximum correspondence. The length of sequence identity comparison may be over at least about five amino acids, usually at least about 20 amino acids, more usually at least about 30 amino acids, typically at least about 50 amino acids, more typically at least about 100 amino acids, and even more typically about 150, 200 or more amino acids. There are a number of different algorithms known in the art that can be used to measure amino acid sequence identity. For instance, amino acid sequences can be compared using FASTA, Gap or Bestfit, which are programs in Wisconsin Package Version 10.0, Genetics Computer Group (GCG), Madison, Wis.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and an analog thereof. See, e.g., GCG Version 6.1 (University of Wisconsin, Wis.). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another algorithm when comparing a sequence to a database containing a large number of sequences from different organisms is the computer program BLAST, especially blastp or tblastn, using default parameters as supplied with the programs. See, e.g., Altschul et al., J. Mol. Biol. 215:403-410 (1990); Altschul et al., Nucleic Acids Res. 25:3389-402 (1997).

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein can typically comprise about 50%, 60%, 70%, 80% or 90% w/w of a protein sample, more usually about 95%, and preferably can be over 99% pure. Protein purity or homogeneity may be indicated by any suitable means, such as polyacrylamide gel electrophoresis of a protein sample followed by visualizing a single polypeptide band upon staining the gel with a stain. As one skilled in the art will appreciate, higher resolution may be provided by using HPLC or other means for purification.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, at least about 90%, and at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" or "substantial similarity" means that two amino acid sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions.

The term "surface plasmon resonance" refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin. 51:19-26 (1993); Jonsson U. et al., Biotechniques 11:620-627 (1991); Jonsson B. et al., J. Mol. Recognit. 8:125-131 (1995); and Johnsson B. et al., Anal. Biochem. 198:268-277 (1991).

"Therapeutically effective amount" refers to that amount of the therapeutic agent being administered which will relieve to some extent one or more of the symptoms of the disorder being treated. In reference to the treatment of rheumatoid arthritis, a therapeutically effective amount refers to that amount which has at least one of the following effects: reducing the structural damage of joints; inhibiting (that is, slowing to some extent, preferably stopping) the accumulation of fluid in the joint area; and relieving to some extent (or, preferably, eliminating) one or more symptoms associated with rheumatoid arthritis.

"Treat", "treating" and "treatment" refer to a method of alleviating or abrogating a biological disorder and/or its attendant symptoms.

The term "utilizes" with reference to a particular gene means that the amino acid sequence of a particular region in an antibody was ultimately derived from that gene during B-cell maturation. For example, the phrase "a heavy chain variable region amino acid sequence that utilizes a human $V_H$-3 family gene" refers to the situation where the $V_H$ region of the antibody was derived from the VH-3 family of gene segments during B-cell maturation. In human B-cells, there are more than 30 distinct functional heavy chain variable genes with which to generate antibodies. Use of a particular heavy chain variable gene, therefore, is indicative of a binding motif of the antibody-antigen interaction with respect to the combined properties of binding to the antigen and functional activity. As will be appreciated, gene utilization analysis provides only a limited overview of antibody structure. As human B-cells stocastically generate V-D-J heavy or V-J kappa light chain transcripts, there are a number of secondary processes that occur, including, without limitation, somatic hypermutation, additions, and CDR3 extensions. See, for example, Mendez et al. *Nature Genetics* 15:146-156 (1997).

The term "vector", as used herein, means a nucleic acid molecule capable of transporting another nucleic acid to which it has been linked. In some cases, the vector is a plasmid, i.e., a circular double stranded piece of DNA into which additional DNA segments may be ligated. For example, the vector is a viral vector, wherein additional DNA segments may be ligated into the viral genome. In another case, the vectors are capable of autonomous replication in a host cell into which they are introduced (e.g., bacterial vectors having a bacterial origin of replication and episomal mammalian vectors). In another example, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The terms "label" or "labeled" refers to incorporation of another molecule in the antibody. For example, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some cases, labels are attached by spacer arms of various lengths to reduce potential steric hindrance.

Therapeutic Methods of Use

Also provided are methods for inhibiting IL-6 activity by administering an IL-6 antibody to a patient in need thereof. Any of the antibodies or antigen-binding portions thereof described herein may be used therapeutically. In a preferred embodiment, the IL-6 antibody is a human, chimeric or humanized antibody. In another preferred embodiment, the IL-6 is human and the patient is a human patient. Alternatively, the patient may be a mammal that expresses an IL-6 that the IL-6 antibody cross-reacts with. The antibody may be administered to a non-human mammal expressing IL-6 purposes or as an animal model of human disease. Such animal models may be used for demonstrating the therapeutic efficacy of the antibodies.

An IL-6 antibody or antibody portion thereof may be administered to a patient who expresses abnormally high levels of IL-6. The antibody may be administered once, or may be administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via a mucosal, buccal, intranasal, inhalable, intravenous, subcutaneous, intramuscular, parenteral, or intratumor route. The antibody may be administered once, at least twice or for at least the period of time until the condition is treated, palliated or cured. The antibody generally will be administered for as long as the condition is present. The antibody will generally be administered as part of a pharmaceutical composition as described herein. The dosage of antibody will generally be in the range of 0.1 to 100 mg/kg, 0.5 to 50 mg/kg, 1 to 20 mg/kg, and 1 to 10 mg/kg. The serum concentration of the antibody may be measured by any suitable method.

Also provided are methods for the treatment of abnormal cell infiltration in a mammal, including a human, comprising administering to the mammal a therapeutically effective amount of an IL-6 antibody or antigen binding portion thereof, as described herein, that is effective in treating abnormal cell infiltration.

The IL-6 antibodies or antigen-binding portions thereof can be used to treat rheumatoid arthritis. They also can be used to treat other diseases in which IL-6 is implicated. Examples of other diseases that can be treated using the IL-6 antibodies or antigen binding portions thereof include osteoarthritis, particularly the pain associated with osteoarthritis, Castleman's disease, juvenile idiopathic arthritis, adult-onset Still's disease, osteoporosis, sepsis, multiple myeloma, renal cell carcinoma, and Crohn's disease.

Some of the diseases that can be treated with the antibodies or antigen-binding portions thereof are discussed below.

Rheumatoid arthritis (RA) is considered a chronic autoimmune and inflammatory disease producing inflamed joints, which eventually swell, become painful, and experience degradation of cartilage, bone, and ligaments of the joint. A result of RA is deformity, instability, and stiffness of the joint and scarring within the joint. The joints deteriorate at a highly variable rate. Many factors, including genetic predisposition, may influence the pattern of the disease. People with rheumatoid arthritis may have a mild course, occasional flare-ups with long periods of remission without disease, or a steadily progressive disease, which may be slow or rapid. Rheumatoid arthritis may start suddenly, with many joints becoming inflamed at the same time. More often, it starts subtly, gradually affecting different joints. Usually, the inflammation is symmetric, with joints on both sides of the body affected. Typically, the small joints in the fingers, toes, hands, feet, wrists, elbows, and ankles become inflamed first, followed by the knees and hips.

Rheumatoid arthritic pain is typically a somatic nociceptive joint pain. Swollen wrists can pinch a nerve and result in numbness or tingling due to carpal tunnel syndrome. Cysts may develop behind affected knees, can rupture, causing pain and swelling in the lower legs.

Osteoarthritis is characterized by loss of articular cartilage and hypertrophy of bone. Onset of osteoarthritis is usually gradual with pain being a common early symptom. As osteoarthritis progresses, joint motion diminishes, and tenderness and grating sensations can occur. Osteoarthritis commonly affects the hands, feet, spine, and large weight-bearing joints, such as the hips and knees. The diagnosis of osteoarthritis is typically based on symptoms or by X-ray, which can show narrowing of the joint space, increased density of subchondral bone, formation of osteophytes at the periphery of joints, and formation of pseudocysts in the subchondral marrow. Blood tests are performed to exclude other conditions that can mimic osteoarthritis. In addition, in diagnosing osteoarthritis, arthrocentesis can be performed, whereby a sterile needle is used to remove joint fluid. Joint fluid analysis is useful in excluding gout, infection, and other causes of arthritis. Osteoarthritis is also known as degenerative joint disease, degenerative arthritis, or osteoarthritis.

Reiter's syndrome (reactive arthritis) is inflammation of the joints and tendon attachments at the joints, often accompanied by inflammation of the eye's conjunctiva and the mucous membranes, such as those of the mouth and genitourinary tract, and by a distinctive rash. Reiter's syndrome is also called reactive arthritis because the joint inflammation appears to be a reaction to an infection originating in the intestine or genital tract. This syndrome is most common in men aged 20 to 40. There are two forms of Reiter's syndrome:

one occurs with sexually transmitted diseases such as a chlamydial infection and the other usually follows an intestinal infection such as shigellosis or salmonellosis. (Most people who have these infections do not develop Reiter's syndrome.) People who develop Reiter's syndrome after exposure to these infections appear to have a genetic predisposition to this type of reaction, related in part to the same gene found in people who have ankylosing spondylitis.

Infectious arthritis is inflammation in a joint resulting from bacterial, fungal, or viral infection of synovial or periarticular tissues. Risk factors for infectious arthritis include advanced age (i.e., greater than 60 years); alcoholism; anemia; arthrocentesis or surgery; chronic medical illness (e.g., lung or liver disease); diabetes; hemophilia; immunodeficiency, including HIV; immunosuppressive therapy, including corticosteroids; IV drug use; malignancy; prosthetic joint implant; renal failure; rheumatoid arthritis; sickle cell disease; skin infections; and systemic lupus erythematosus. Patients with rheumatoid arthritis are at particularly increased risk for bacterial arthritis. Joint infections may be acute, with sudden onset of joint pain and swelling (e.g., within a few hours to a few days), or chronic, with insidious development of milder symptoms. Acute bacterial arthritis is commonly accompanied by moderate to severe joint pain, warmth, tenderness, and restricted motion. Chronic bacterial arthritis is commonly accompanied by gradual swelling, mild warmth, minimal or no redness of the joint area, and aching pain, which may be mild.

Psoriatic arthritis is an inflammatory arthritis affecting the joints that occurs in a minority of psoriasis patients and increasingly in some acquired immune deficiency syndrome (AIDS) patients. Psoriatic arthritis may be mild or may produce severe joint deformities resembling joint changes observed in rheumatoid arthritis. Joints that may be affected by psoriatic arthritis include distal interphalangeal (DIP) joints of fingers and toes, and commonly the asymmetric involvement of large and small joints such as sacroiliacs and spine. Psoriasis of the skin or nails may precede or follow joint involvement. The time course of psoriatic arthritis is characterized by arthritic exacerbations and remissions that may or may not coincide with skin exacerbations and remissions, and progression to chronic arthritis may occur. Diagnosis includes a diagnosis of psoriasis, a family history of psoriasis, X-ray findings showing DIP joint involvement, asymmetric large joint involvement, a negative blood test for rheumatoid factor to rule out rheumatoid arthritis, and, in some patients, the presence of HLA-B27 antigen, especially when the spine is involved.

Polyarthritis is any type of arthritis which involves five or more joints. Arthritis of two, three or four joints is called oligoarthritis or pauciarthritis. Polyarthritis is most often caused by an autoimmune disorder such as rheumatoid arthritis, psoriatic arthritis, or lupus erythematosus, but can also be caused by infections. Polyarthritis may be experienced at any age and is not gender specific.

Juvenile arthritis is arthritis that begins before age 16. There are several different types of juvenile arthritis. The most common type is juvenile rheumatoid arthritis (JRA), also known as juvenile idiopathic arthritis. JRA includes systemic onset JRA, pauciarticular JRA, which involves fewer than five joints, and polyarticular JRA, which affects five or more joints. Diagnosis of JRA involves considering the symptoms, taking x-rays and doing blood analyses. Specific tests that doctor may use to diagnose JRA include complete blood counts, blood cultures for infections, bone marrow examinations, examination of erythrocyte sedimentation rate, rheumatoid factor antibody determination, antinuclear antibody determination, and bone scans.

Juvenile rheumatoid arthritis is persistent or recurring inflammation of the joints similar to rheumatoid arthritis but beginning before age 16 and is characterized by inflammation of joints or connective tissue. There are several types of juvenile rheumatoid arthritis, which are determined by the symptoms that develop during the first months of the disease and how many joints are affected. These types include pauciarticular juvenile rheumatoid arthritis, polyarthritis, and systemic disease (Still's disease). In pauciarticular juvenile rheumatoid arthritis, four or fewer joints, usually those of the leg are affected. In polyarthritis, five or more (sometimes as many as 20 to 40) joints are affected. In systemic disease (Still's disease), any number of joints can be involved.

Juvenile reactive arthritis is persistent or recurring inflammation of the joints similar to reactive arthritis but beginning before age 16.

Juvenile psoriatic arthritis is psoriatic arthritis that begins in a patient before the age of 16 years and is characterized by the presence of chronic arthritis and psoriasis; or chronic arthritis and at least two of the following: dactylitis, nail abnormalities (e.g., pitting or onycholysis), and a family history of psoriasis in at least one immediate relative. As in adults with psoriatic arthritis, the arthritis may precede the skin condition. The predominant pattern at onset of juvenile psoriatic arthritis is an asymmetric oligoarthritis of small and large joints often with dactylitis.

In one aspect, the IL-6 mediated disorder is characterized by fibrosis. The term "fibrosis" as used herein refers to a pathological condition characterized by excessive deposition and metabolism of fibrotic material (e.g., extracellular matrix) in response to tissue damage. In many cases, fibrosis represents a normal repair process (i.e., wound healing) gone awry due to chronic or excessive tissue insult leading to fibroblast or stellate cell activation and proliferation and collagen accumulation. Fibrosis conditions include fibroproliferative disorders that are associated with vascular diseases, such as cardiac disease, cerebral disease, and peripheral vascular disease, as well as all the main tissues and organ systems such as the eye, skin, kidney, lung, gut and liver (Wynn, *Nature Reviews* 4:583-594 (2004); Bataller, R and Brenner, D., *J. Clin. Invest.* 115:209-218 (2005)). Other sources are chemotherapeutic drugs, radiation-induced fibrosis, and injuries and burns. While fibrosis conditions cover a wide group of pathologies, it is believed that for most of these conditions, the general mechanisms leading to fibrotic tissue accumulation have many elements in common. Often the condition is initiated in response to an influx of inflammatory cells and perpetuated by the subsequent cytokine signaling pathways between the infiltrating cells (e.g., macrophages, T cells) and resident cells within the tissue (e.g., stellate, myofibroblast. Kupffer cells). In addition, pericytes are a key fibrogenic cell type involved in the development of scleroderma and PDGF receptor tyrosine kinase inhibitors (RTKI) have been shown to slow the proliferation of pericytes and suppress skin lesions in patients with this progressive disease. In the kidney, leukocyte infiltration plays a major role in mediating tubulointerstitial inflammation and fibrosis in chronic kidney disease.

As used herein the term "fibrosis" is also used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts or stellate cells migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called α-chains, which are wound around each other in a ropelike helix. Collagen exists in several forms or types; of these, type I, the most common, is found in skin, tendon, and bone; and type III is found in skin, blood vessels, and internal organs. Exemplary fibrosis conditions include, but are not limited to (I) Lung diseases associated with fibrosis, e.g., idiopathic pulmonary fibrosis, radiation induced fibrosis, chronic obstructive pulmonary disease (COPD), scleroderma, bleomycin induced pulmonary fibrosis, chronic asthma, silicosis, asbestos induced pulmonary fibrosis, acute lung injury and acute respiratory distress (including bacterial pneumonia induced, trauma induced, viral pneumonia induced, ventilator induced, non-pulmonary sepsis induced, and aspiration induced);

(II) Chronic nephropathies associated with injury/fibrosis (kidney fibrosis), e.g., lupus, diabetes, scleroderma, glomerular nephritis, focal segmental glomerular sclerosis, IgA nephropathy, hypertension, allograft, Lupus, and Alport;

(III) Gut fibrosis, e.g., scleroderma, and radiation induced gut fibrosis;

(IV) Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g. chronic HCV infection), and autoimmune hepatitis;

(V) Head and neck fibrosis, e.g., radiation induced;

(VI) Corneal scarring, e.g., LASIX™, corneal transplant, and trabeculectomy;

(VII) Hypertrophic scarring and keloids, e.g., burn induced and surgical; and other fibrotic diseases, e.g., sarcoidosis, scleroderma, spinal cord injury/fibrosis, myelofibrosis, vascular restenosis, atherosclerosis, Wegener's granulomatosis, mixed connective tissue disease, and Peyronie's disease.

The term "fibromyalgia" is also known as fibromyalgia syndrome. The American College of Rheumatology (ACR) 1990 classification criteria for fibromyalgia include a history of chronic, widespread pain for more than three months, and the presence of pain at 11 (or more) out of 18 tender points upon physical examination, wherein the tender points occur both above and below the waist and on both sides of the body (see e.g., Wolfe et al., Arthritis Rheum., 1990; 33:160-172). Fibromyalgia patients generally display pain perception abnormalities in the form of both allodynia (pain in response to a normally non-painful stimulus) and hyperalgesia (an increased sensitivity to a painful stimulus). The effects of fibromyalgia in a human patient may be assessed using the ACR criteria, a Fibromyalgia Index Questionnaire (FIQ) total score, indices of pain severity (e.g., VAS or Likert pain scales) and interference, the number of tender points, or a pain threshold assessment.

Although chronic, widespread pain is a hallmark symptom of fibromyalgia, patients typically also exhibit other symptoms, including one or more of the following: fatigue, sleep disturbances, migraine or tension headaches, irritable bowel syndrome, changes in urinary frequency, morning stiffness, numbness and tingling, dysmenorrhea, multiple chemical sensitivities, difficulty concentrating, and circulatory problems that affect the small blood vessels of the skin (Raynaud's phenomenon). As with many conditions that cause chronic pain, fibromyalgia patients may also experience fibromyalgia-induced anxiety, depression, or both. Some fibromyalgia patients find that cold, damp weather, emotional stress, over-exertion, and other factors exacerbate their symptoms.

Pain associated with fibromyalgia refers to any pain associated with fibromyalgia syndrome, including the chronic, widespread pain that is a hallmark of fibromyalgia and pain associated with other symptoms of fibromyalgia.

Ankylosing spondylitis is a rheumatic disease that causes arthritis of the spine and sacroiliac joints. It varies from intermittent episodes of back pain that occur throughout life to a severe chronic disease that attacks the spine, peripheral joints and other body organs. Typically, the first symptoms are frequent pain and stiffness in the lower back and buttocks, which comes on gradually over the course of a few weeks or months. The pain is usually dull and diffuse, rather than localized. Ankylosing spondylitis is typically diagnosed with a thorough physical exam including x-rays, individual medical history, and a family history of ankylosing spondylitis, as well as blood work including a test for HLA-B27.

Psoriasis is a chronic inflammatory skin disorder that may afflict people of all ages. Clinically, psoriasis most frequently affects the skin of the elbows, knees, scalp, lumbosacral areas, intergluteal cleft, or glans penis. Skin affected by psoriasis typically contains one or more dry lesions comprised of a well-demarcated, pink to salmon-colored plaque covered by loosely adherent scales that are characteristically silver-white in color. In about 30% of psoriasis patients, the nails are also affected by, for example, pitting or onycholysis. All forms of psoriasis are contemplated, including psoriasis annularis and psoriasis annulata, which are also known as psoriasis circinata; psoriasis arthropica; psoriasis diffusa or diffused psoriasis; exfoliative psoriasis; flexural psoriasis; psoriasis geographica; psoriasis gyrate; psoriasis nummularis; palmar psoriasis; psoriasis punctata; and a rare variant form known as generalized pustular psoriasis of Zambusch or simply just pustular psoriasis. Morphologically, established lesions of psoriasis have well known histologic characteristics such as epidermal thickening and parakeratotic scale. Pathologically, psoriasis is currently believed to be a T-cell mediated autoimmune disorder. Onset of psoriasis is usually gradual and the typical time course is characterized by chronic remissions and recurrences and, occasionally, acute exacerbations. Diagnosis of psoriasis is made by evaluating a patient's clinical signs and symptoms and family history of psoriasis. Diagnosing psoriasis by just visually inspecting the patient's skin lesions is rarely difficult and usually this is all that is required for a complete diagnosis. Occasionally, however, a skin biopsy is subjected to a histologic analysis to look for signs of psoriasis.

Systemic lupus erythematosus ("SLE"), also called disseminated lupus erythematosus, is a chronic inflammatory connective tissue disorder of unknown cause that can involve joints, kidneys, serous surfaces, and vessel walls and that occurs predominantly in young women but also in children. Ninety percent of SLE cases occur in women. SLE may begin abruptly with fever, simulating acute infection, or may develop insidiously over months or years with episodes of fever and malaise. Vascular headaches, epilepsy, or psychoses may be initial findings. Manifestations referable to any organ system may appear. Articular symptoms, ranging from intermittent arthralgias to acute polyarthritis, occur in approximately 90% of patients and may exist for years before other manifestations appear. In long-standing disease, capsular insertional erosions at the metacarpophalangeal joints with marked secondary joint deformity may occur without x-ray evidence of obvious marginal erosions (Jaccoud's arthritis). However, most lupus polyarthritis is nondestructive and nondeforming.

Systemic lupus erythematosus is rare under the age of 5, and most children with SLE develop the disease during adolescence. Signs and symptoms of juvenile SLE are similar to those in adults. However, children have a particularly high level of transition from the discoid to the systemic disease.

Gout (also known as gouty arthritis) is recurrent acute or chronic arthritis of peripheral joints results from a build-up in the body of too much uric acid, which forms crystals that deposit in joints and cause inflammation. During an acute attack of gout there is swelling, inflammation, and extreme pain in a joint, frequently that of the big toe. Chronic gout can set in after several years of attacks, permanently damaging and deforming joints and destroying cells of the kidney. Most cases occur in men and the first attack rarely occurs before the age of 30.

Undifferentiated Spondyloarthropathy (USpA) is a term used to describe symptoms and signs of spondylitis in someone who does not meet the criteria for a definitive diagnosis of ankylosing spondylitis or related disease. A number of well-established syndromes are included within the spondyloarthropathy family including ankylosing spondylitis, psoriatic arthritis, the arthritis of inflammatory bowel disease, Reiter's syndrome, chronic reactive arthritis and enthesitis related juvenile arthritis. Over time, some people with USpA will develop a well-defined form of spondylitis such as ankylosing spondylitis.

Juvenile-onset spondyloarthritis (JSpA), also known as Juvenile Spondyloarthropathy, is the medical term for a group of childhood rheumatic diseases, which cause arthritis before the age of 16 and may span through adult life. The juvenile spondyloarthropathies include undifferentiated spondyloarthropathy, juvenile ankylosing spondylitis, juvenile psoriatic arthritis, the arthritis associated with inflammatory bowel disease (enteropathogenic arthritis), reactive arthritis, (Reiter's syndrome is one type of reactive arthritis), and the SEA syndrome (seronegativity, enthesopathy, arthropathy). JSpA typically causes pain and inflammation in the joints in the lower part of the body, for example, the pelvis, hips, knees and ankles. Other areas of the body can also be affected, such as the spine, eyes, skin and bowels. Fatigue and lethargy can also occur.

Crohn's disease is a nonspecific chronic transmural inflammatory disease that most commonly affects the distal ileum and colon but may occur in any part of the GI tract. Chronic diarrhea with abdominal pain, fever, anorexia, weight loss, and a right lower quadrant mass or fullness are the most common symptoms of Crohn's disease. Less common symptoms include poor appetite, fever, night sweats, rectal pain, and rectal bleeding. Crohn's disease may affect the colon, the rectum, and the small intestine and, in rare instances, also the stomach, mouth, and esophagus. The most common patterns of Crohn's disease pathology are (1) inflammation characterized by right lower quadrant abdominal pain and tenderness; (2) recurrent partial obstruction caused by intestinal stenosis and leading to severe colic, abdominal distention, constipation, and vomiting; (3) diffuse jejunoileitis, with inflammation and obstruction resulting in malnutrition and chronic debility; and (4) abdominal fistulas and abscesses, usually late developments, often causing fever, painful abdominal masses, and generalized wasting. Crohn's disease should be suspected in a patient with the inflammatory or obstructive symptoms described above and in a patient without prominent GI symptoms but with perianal fistulas or abscesses or with otherwise unexplained arthritis, erythema nodosum, fever, anemia, or stunted growth (in a child). Laboratory findings are nonspecific and may include anemia, leukocytosis, hypoalbuminemia, and increased levels of acute-phase reactants reflected in elevated ESR, C-reactive protein, or orosomucoids. Elevated alkaline phosphatase and γ-glutamyl transpeptidase accompanying colonic disease often reflect primary sclerosing cholangitis. Diagnosis is usually made by x-ray.

In advanced cases, the string sign may be seen with marked ileal strictures and separation of bowel loops. In earlier cases, x-ray diagnosis may sometimes be difficult, but air double-contrast barium enema and enteroclysis may show superficial aphthous and linear ulcers. Colonoscopy and biopsy may help confirm the diagnosis of Crohn's colitis and allow direct visualization and biopsy of the terminal ileum. Upper GI endoscopy may identify gastroduodenal involvement in Crohn's disease patients with upper GI symptoms.

Ulcerative colitis is a chronic, inflammatory, and ulcerative disease arising in the colonic mucosa, characterized most often by bloody diarrhea. Bloody diarrhea of varied intensity and duration is interspersed with asymptomatic intervals are the most common symptoms of ulcerative colitis. Usually an attack begins insidiously, with increased urgency to defecate, mild lower abdominal cramps, and blood and mucus in the stools. However, an attack may be acute and fulminant, with sudden violent diarrhea, high fever, signs of peritonitis, and profound toxemia. Some cases develop following a documented infection (e.g., amebiasis, bacillary dysentery). When ulceration is confined to the rectosigmoid, the stool may be normal or hard and dry, but rectal discharges of mucus loaded with red blood cells and white blood cells accompany or occur between bowel movements. Systemic symptoms are mild or absent. If ulceration extends proximally, stools become looser and the patient may have >10 bowel movements/day, often with severe cramps and distressing rectal tenesmus, without respite at night. The stools may be watery, may contain mucus, and frequently consist almost entirely of blood and pus. Malaise, fever, anemia, anorexia, weight loss, leukocytosis, and hypoalbuminemia may be present with extensive active ulcerative colitis. The patient's history and stool examination permit a presumptive diagnosis of ulcerative colitis that should always be confirmed by sigmoidoscopy, which provides a direct, immediate indication of disease activity. In early cases, the mucous membrane is finely granular and friable, with loss of the normal vascular pattern and often with scattered hemorrhagic areas; minimal trauma (friability) causes bleeding in multiple pinpoint spots. The mucosa soon breaks down into a red, spongy surface dotted with many tiny blood- and pus-oozing ulcers. As the mucosa becomes progressively involved, the inflammation and hemorrhage extend into the bowel muscle. Large mucosal ulcers with copious purulent exudate characterize severe disease. Islands of relatively normal or hyperplastic inflammatory mucosa (pseudopolyps) project above areas of ulcerated mucosa. Biopsies may be nonspecific and sometimes cannot exclude acute infectious (self-limited) colitis; however, features that suggest chronicity (e.g., distorted crypt architecture, crypt atrophy, a chronic inflammatory infiltrate) support the diagnosis of ulcerative colitis. Even during asymptomatic intervals, the sigmoidoscopic appearance is rarely normal; some degree of friability or granularity almost always persists. There is loss of the normal vascular pattern, and biopsy shows evidence of chronic inflammation. Plain x-rays of the abdomen sometimes help to judge the severity and proximal extent of the colitis by showing loss of haustration, mucosal edema, and absence of formed stool in the diseased bowel. Later in the course of disease, however, the entire colon should be evaluated to determine the extent of involvement. Total colonoscopy is the most sensitive and widely used method, although barium enema can be informative. Colonoscopy with biopsy is mandatory to evaluate the nature of a stricture. Biopsy may also help distinguish ulcerative colitis from Crohn's disease if the inflammation is highly focal or if a granuloma is seen.

Irritable bowel syndrome (IBS) is a motility disorder involving the entire GI tract, causing recurring upper and lower GI symptoms, including variable degrees of abdominal pain, constipation and/or diarrhea, and abdominal bloating. The cause of irritable bowel syndrome (IBS) is unknown. No anatomic cause can be found. Emotional factors, diet, drugs, or hormones may precipitate or aggravate heightened GI motility. Features of IBS are pain relieved by defecation, an alternating pattern of bowel habits, abdominal distention, mucus in the stool, and sensation of incomplete evacuation after defecation. In general, the character and location of pain, precipitating factors, and defecatory pattern are distinct for each patient. Patients with IBS may also have extraintestinal symptoms (e.g., fibromyalgia, headaches, dyspareunia, temporomandibular joint syndrome). Two major clinical types of IBS have been described. In constipation-predominant IBS, constipation is common, but bowel habits vary. Most patients have pain over at least one area of the colon, associated with periodic constipation alternating with a more normal stool frequency. Stool often contains clear or white mucus. The pain is either colicky, coming in bouts, or a continuous dull ache; it may be relieved by a bowel movement. Eating commonly triggers symptoms. Bloating, flatulence, nausea, dyspepsia, and pyrosis can also occur. Diarrhea-predominant IBS is characterized by precipitous diarrhea that occurs immediately on rising or during or immediately after eating. Nocturnal diarrhea is unusual. Pain, bloating, and rectal urgency are common, and incontinence may occur. Diagnosis of IBS is based on characteristic bowel patterns, time and character of pain, and exclusion of other disease processes through physical examination and routine diagnostic tests. Due to a lack of a readily identifiable structural or biochemical abnormality in this syndrome, the medical community has developed a consensus definition and criteria, known as the Rome criteria, to aid in diagnosis of IBS. According to the Rome criteria, IBS is indicated by abdominal pain or discomfort which is (1) relieved by defection and/or (2) associated with a change in frequency or consistency of stools, plus two or more of the following: altered stool frequency, altered stool formation, altered stool passage, passage of mucus, and bloating or feeling of abdominal distention. Palpation of the abdomen may reveal tenderness, particularly in the left lower quadrant, at times associated with a palpable, tender sigmoid. A routine digital rectal examination should be performed on all patients, and a pelvic examination on women.

Irritable bowel disease (IBD), also known as inflammatory bowel disease, is characterized by chronic inflammation at various sites in the GI tract. IBD comprises two known clinical subtypes, Crohn's Disease (CD) and ulcerative colitis (UC). Certain differences in disease patterns justify a distinction between Crohn's disease and ulcerative colitis.

Pain associated with IBD and IBS may present as either chronic or acute pain. For example a feature of IBS is acute pain relieved by defication while chronic abdominal pain is typical of Crohn's disease. While pain associated with IBD and IBS may occur extraintestinal or extravisceral generally these ailments produce visceral pain. Viceral pain is pain associated with the viscera, which encompasses the organs of the abdominal cavity. These organs include the sex organs, spleen intestines, colon, rectum and other organs of the digestive system. Visceral pain has five important clinical characteristics: (1) it is not evoked from all viscera (organs such as liver, kidney, most solid viscera, and lung parenchyma are not sensitive to pain); (2) it is not always linked to visceral injury; (3) it is diffuse and poorly localized; (4) it is referred to other locations; and (5) it is accompanied with motor and autonomic reflexes, such as the nausea, vomiting, and lower-back muscle tension that occurs in renal colic.

Pain is an important physiological protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibers are known as nociceptors and are characteristically small diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinically, pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibers. Myelinated A-delta fibers transmit rapidly and are responsible for sharp and stabbing pain sensations, while unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumor related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intravertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

IL-6 antibodies or antigen-binding portions thereof can be used in combination with one or more other therapeutic agents. For example, an antibody or antigen-binding portions thereof can be used with a COX-2 inhibitor, such as celecoxib, for the treatment of diseases such as rheumatoid arthritis, osteoarthritis and pain. IL-6 antibodies or antigen-binding portions thereof and the other therapeutic agents can be administered to the patient in the same dosage form or in different dosage forms. Moreover, they can be administered at the same time or at different times. Below are some examples of therapeutic agents that can be used in combination with anti-IL-6 antibodies or antigen-binding portions thereof.

Rheumatoid Arthritis

IL-6 antibodies and antigen binding portions thereof may also be used in co-therapies. Suitable antiinflammatory co-therapy compounds include: cyclosporine, zoledronic acid, efalizumab, alefacept, etodolac, lornoxicam, OM-89, valdecoxib, tocilizumab, abatacept, meloxicam, etanercept, nambumetone, rimexolone, 153Sm-EDTMP, prosorba, imidazole salicylate, oprelvekin, hylauronic acid, naproxen, piroxicam, diacerein, lumericoxib, tacrolimus, aceclofenac, actarit, tenoxicam, rosiglitazone, deflazacort, adalimumab, leflunomide, risedronate sodium, misoprostol and diclofenac, SK-1306X, infliximab, anakinra, celecoxib, diclofenac, etoricoxib and felbinac, reumacon, golimumab, denosumab, ofatumumab, 10rT1 antibody, pelubiprofen, licofelone, temsirolimus, eculizumab, iguratimod, and prednisone. Other suitable antiinflammatories include CP-481715, ABN-912, MLN-3897, HuMax-IL-15, RA-1, paclitaxel, Org-37663, Org 39141, AED-9056, AMG-108, fontolizumab, pegsunercept, pralnacasan, apilimod, GW-274150, AT-001, 681323 (GSK) K-832, R-1503, ocrelizumab, DE-096, Cpn10, THC+ CBD (GW Pharma), 856553 (GSK), ReN-1869, immunoglobulin, mm-093, amelubant, SC10-469, ABT-874, LenkoVAX, LY-2127399, TRU-015, KC-706, amoxapinet and dipyridamole, TAK-715, PG 760564, VX-702, prednisolone and dipyridamole, PMX-53, belimumab, prinaberel, CF-101, tgAAV-TNFR:Fc, R-788, prednisolone and SSRI, CP-690550 and PMI-001.

Osteoarthritis

IL-6 antibodies and antigen binding portions thereof may further be co-administered for the treatment of osteoarthritis with one or more agents useful for treating one or more indicia of osteoarthritis. Examples of agents useful for treating one or more indicia of osteoarthritis to be used in combination with anti-IL-6 antibodies or antigen-binding portions thereof include matrix metalloproteinase (MMP) inhibitors, aggrecanase inhibitors, inducible nitric oxide (iNOS) inhibitors, inhibitors of insulin-like growth factor (IGF) expression or activity, inhibitors of fibroblast growth factor (FGF) expression or activity, inhibitors of CD 44 expression or activity, inhibitors of interleukin (IL) expression or activity, inhibitors of tumor necrosis factor alpha (TNF-alpha) expression or activity, inhibitors of tumor necrosis factor-inducible protein 6 (TSG-6) expression or activity, inhibitors of Bikunin expression or activity, inhibitors of beta-secretase (BACE), inhibitors of PACE-4, inhibitors of nuclear receptor rev-ErbA alpha (NR1D1) expression or activity, inhibitors of endothelial differentiation sphingolipid G-protein-coupled receptor 1 (EDG-1) expression or activity, inhibitors of proteinase-activated receptor (PAR) expression or activity, inhibitors of cartilage-derived retinoic-acid-sensitive protein (CD-RAP) expression or activity, inhibitors of protein kinase C zeta (PKCz), inhibitors of resistin expression or activity, inhibitors of a disintegrin and metalloproteinase 8 (ADAMS), inhibitors of complement component 1 s subcomponent (C1s) expression or activity, inhibitors of formyl peptide receptor-like 1 (FPRL1) expression or activity.

Additional examples of agents useful in combination with IL-6 antibodies and antigen binding portions thereof include inhibitors of MMP-2, -3, -9, or -13; inhibitors of aggrecanase-1 or -2; inhibitors of IGF-1 or -2 expression or activity; inhibitors of FGF-2, -18, or -9 expression or activity; and inhibitors of IL-1, -4 or -6 expression or activity.

Further examples of agents useful in combination with IL-6 antibodies and antigen binding portions thereof include IGF-1 or -2 antibodies; FGF receptor-2 or -3 antagonists, CD 44 antibodies, IL-1, -4 or -6 antibodies, TNF-alpha antibodies; TSG-6 antibodies; bikunin antibodies; NR1D1 antagonists; EDG-1 antagonists; PAR antagonists, CD-RAP antibodies, resistin antibodies, C1s antibodies, and FPRL1 antibodies.

Pain

IL-6 antibodies or antigen binding portions thereof can be administered in combination with one or more additional pharmacologically active compounds for the treatment of pain. The compounds may be administered at the same time in a single dosage form or separately in dosage forms that can be the same or different. Alternatively, the compounds can be administered sequentially. The pharmaceutically acceptable salts of the pharmacologically active compounds may also be used in the combinations.

Examples of compounds that can be administered with IL-6 antibodies or antigen binding portions thereof include:

Cyclooxygenase-2 (COX-2) selective inhibitors such as celecoxib, rofecoxib, parecoxib, valdecoxib, deracoxib, etoricoxib, and lumiracoxib; opioid analgesics such as morphine, hydromorphone, oxymorphone, fentanyl, codeine, dihydrocodeine, oxycodone, hydrocodone, buprenorphine, tramadol, and nalbuphine; nonsteroidal antiinflammatory drugs (NSAIDs) such as aspirin, diclofenac, diflunisal, ibuprofen, fenoprofen, naproxen, nepafenac, and acetaminophen; Phosphodiesterase V inhibitors (PDEV) such as sildenafil; alpha-2-delta ligands such as gabapentin and pregabalin; and local anaesthetics such as benzocaine, lidocaine, ropivacaine, menthol, camphor and methyl salicylate.

Examples of other types of compounds and classes of compounds that can be used in combination with IL-6 antibodies and antigen binding portions thereof include: barbiturate sedatives; benzodiazepines; Histamine $H_1$ antagonists having a sedative action; sedatives; skeletal muscle relaxants; N-methyl-D-aspartic acid (NMDA) receptor antagonists; alpha-adrenergics; tricyclic antidepressants; anticonvulsants such as carbamazepine; tachykinin (NK) antagonists, particularly NK-3, NK-2 or NK-1 antagonists; muscarinic antagonists; neuroleptics; vanilloid receptor agonists or antagonists; beta-adrenergics; corticosteroids; Serotonin (5-HT) receptor agonists or antagonists such as a $5\text{-}HT_{1B/1D}$, $5\text{-}HT_{2A}$, and $5\text{-}HT_3$ receptor antagonists; cholinergic (nicotinic) analgesics; cannabinoids; metabotropic glutamate subtype 1 receptor (mGluR1) antagonists; serotonin reuptake inhibitors such as sertraline; noradrenaline (norepinephrine) reuptake inhibitors such as reboxetine, in particular (S,S)-reboxetine; dual serotonin-noradrenaline reuptake inhibitors such as duloxetine; inducible nitric oxide synthase (iNOS) inhibitors such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, and guanidinoethyldisulfide; acetylcholinesterase inhibitors; prostaglandin $E_2$ subtype 4 (EP4) antagonists such as N-[({2-[4-(2-ethyl-4,6-dimethyl-1H-imidazo[4,5-c]pyridin-1-yl) phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid; leukotriene B4 antagonists such as 1-(3-biphenyl-4-ylmethyl-4-hydroxychroman-7-yl)-cyclopentanecarboxylic acid; 5-lipoxygenase inhibitors; and sodium channel blockers.

Fibromyalgia Syndrome

Products: analgesics such as acetaminophen, naproxen sodium, ibuprofen, tramadol, trazodone; cyclobenzaprine; aspirin, celecoxib, valdecoxib, indomethacin, and other NSAIDs; antidepressants such as tricyclic antidepressants and selective serotonin reuptake inhibitors, for example antidepressants such as amitriptyline, imipramine, nortriptyline, doxepin, fluoxetine, sertraline, and paroxetine; muscle relaxants such as cyclobenzaprine; sleeping aids such as zolpidem.

Classes: norepinephrine-serotonin reuptake inhibitors (NSRIs and SNRIs); norepinephrine reuptake inhibitor (NRIs); selective serotonin reuptake inhibitors (SSRIs); tricyclic antidepressants; selective cyclooxygenase-2 (COX-2) inhibitors; nonsteroidal anti-inflammatory drugs (NSAIDs); analgesics.

Ankylosing Spondylitis

Products: analgesics such as acetaminophen, naproxen sodium, ibuprofen, tramadol, aspirin, celecoxib, valdecoxib, indomethacin, and other NSAIDs; disease-modifying anti-rheumatic drugs (DMARDs) such as sulfasalazine or methotrexate; corticosteroids; and tumor necrosis factor (TNF) blockers such as etanercept and infliximab.

Classes: analgesics; NSAIDs; COX-2 inhibitors; DMARDs; corticosteroids; TNF blockers.

Psoriasis

Products: phototherapy, including psoralen ultraviolet A (psoralen UVA or PUVA) therapy, narrow-band ultraviolet B (UVB) therapy, and combination light therapy; topical corticosteroids; vitamin D analogs such as calcipotriene; anthralin; topical retinoids (i.e., vitamin A derivatives) such as acitretin and tazarotene; clobetasol propionate; methotrexate; azathioprine; cyclosporine; hydroxyurea; and immune-modulating drugs such as alefacept, efalizumab, and etanercept.

Classes: phototherapy; corticosteroids; vitamin D analogs; vitamin A derivatives.

Gout

Products: NSAIDs such as acetaminophen, naproxen sodium, ibuprofen, tramadol, aspirin, celecoxib, valdecoxib, and indomethacin; and corticosteroids such as prednisone.

Classes: analgesics; NSAIDs; COX-2 inhibitors; and corticosteroids.

Crohn's Disease

Products: analgesics such as acetaminophen, naproxen sodium, ibuprofen, tramadol, aspirin, celecoxib, valdecoxib, indomethacin, and other NSAIDs; anti-inflammatory drugs; sulfasalazine, mesalamine, balsalazide, and olsalazine; and corticosteroids such as prednisone and budesonide; immunosuppressant drugs such as azathioprine, mercaptopurine, TNF blockers such as infliximab and adalimumab, methotrexate, and cyclosporine; antibiotics such as metronidazole and ciprofloxacin; anti-diarrheals such as loperamide; and laxatives.

Classes: analgesics; NSAIDs; COX-2 inhibitors; anti-inflammatory drugs; TNF blockers; antibiotics; anti-diarrheals; and laxatives.

Ulcerative Colitis

Classes: analgesics such as acetaminophen, naproxen sodium, ibuprofen, tramadol, aspirin, celecoxib, valdecoxib, indomethacin, and other NSAIDs; anti-inflammatory drugs; sulfasalazine, mesalamine, balsalazide, and olsalazine; corticosteroids; immunosuppressant drugs such as azathioprine, mercaptopurine, TNF blockers such as infliximab and adalimumab, methotrexate, and cyclosporine; anti-diarrheals such as loperamide; and laxatives.

Classes: NSAIDs; COX-2 inhibitors; anti-inflammatory drugs; TNF blockers; corticosteroids; immunosuppressants; Janus kinase-3 (Jak-3) inhibitors; TNF blockers; anti-diarrheals; and laxatives.

Irritable Bowel Syndrome

Products: anti-diarrheals such as loperamide; laxatives; anticholinergic drugs; antidepressants such as tricyclic antidepressants and selective serotonin reuptake inhibitors, for example antidepressants such as amitriptyline, imipramine, nortriptyline, doxepin, fluoxetine, sertraline, and paroxetine; alosetron; and tegaserod.

Classes: anti-diarrheals; laxatives; anticholinergic drugs; norepinephrine-serotonin reuptake inhibitors (NSRIs and SNRIs); norepinephrine reuptake inhibitor (NRIs); selective serotonin reuptake inhibitors (SSRIs); tricyclic antidepressants.

Pharmaceutical Compositions and Administration

Also provided are pharmaceutical compositions for the treatment of abnormal cell infiltration in a mammal, including a human, comprising an amount of an IL-6 antibody or antigen binding portion thereof, as described herein, that is effective in treating abnormal cell infiltration, and a pharmaceutically acceptable carrier. The compositions provide a therapeutic benefit to patients with one of more of a variety of inflammatory and autoimmune diseases, such as rheumatoid arthritis, atherosclerosis, granulomatous diseases, multiple sclerosis, asthma and cancer.

IL-6 antibodies and antigen-binding portions thereof can be incorporated into pharmaceutical compositions suitable for administration to a subject. Typically, the pharmaceutical composition comprises an IL-6 antibody or antigen-binding portion thereof and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application. Typical compositions are in the form of injectable or infusible solutions, such as compositions similar to those used for passive immunization of humans. In one case the mode of administration is parenteral (e.g., intravenous, subcutaneous, intraperitoneal, intramuscular). In another case, the antibody is administered by intravenous infusion or injection. In another case, the antibody is administered by intramuscular or subcutaneous injection. Formulations for injection may be presented in unit dosage form, e.g., in ampoules or in multi-dose containers, with or without an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. Sterile injectable solutions can be prepared by incorporating the IL-6 antibody in the required amount in an appropriate solvent with one or a combination of ingredients enumerated above, as required, followed by filter sterilization. In one case, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80 or polysorbate 20, from about 100 millimolar to about 400 millimolar of a non-reducing sugar selected from but not limited to trehalose or sucrose, from about 0.01 millimolar to about 1.0 millimolar of disodium EDTA dihydrate and optionally comprise a pharmaceutically acceptable antioxidant in addition to a chelating agent. Suitable antioxidants include, but are not limited to, methionine, sodium thiosulfate, catalase, and platinum. For example, the composition may contain methionine in a concentration that ranges from 1 mM to about 100 mM, and in particular, is about 27 mM. In some cases, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. In the case of sterile powders for the preparation of sterile injectable solutions, the suitable methods of preparation include vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

IL-6 antibodies or antigen-binding portions thereof can be administered by a variety of methods, although for many therapeutic applications, the route/mode of administration can be subcutaneous, intramuscular, or intravenous infusion. As will be appreciated by the skilled artisan, the route and/or mode of administration will vary depending upon the desired results.

In certain cases, the IL-6 antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations may be used. See, e.g., Sustained and Controlled Release Drug Delivery Systems, J. R. Robinson, ed., Marcel Dekker, Inc., New York, 1978, which is incorporated herein by reference.

Additional active compounds also can be incorporated into the compositions. In some cases, an inhibitory IL-6 antibody is co-formulated with and/or co-administered with one or more additional therapeutic agents. These agents include, without limitation, antibodies that bind other targets, anti-tumor agents, anti-angiogenesis agents, signal transduction inhibitors, anti-proliferative agents, chemotherapeutic agents, or peptide analogues that inhibit IL-6. Such combination therapies may require lower dosages of the inhibitory IL-6 antibody as well as the co-administered agents, thus avoiding possible toxicities or complications associated with the various monotherapies.

The compositions may include a "therapeutically effective amount" or a "prophylactically effective amount" of an antibody or antigen-binding portion. A "therapeutically effective amount" refers to an amount effective, at dosages and for periods of time necessary, to achieve the desired therapeutic result. A therapeutically effective amount of the antibody or antigen-binding portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antigen-binding portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of IL-6 antibody or antigen binding portion thereof calculated to produce the desired therapeutic effect in association with the required pharmaceutical carrier.

An exemplary, non-limiting range for a therapeutically or prophylactically effective amount of an IL-6 antibody or antibody portion is 0.025 to 50 mg/kg, 0.1 to 50 mg/kg, 0.1-25, 0.1 to 10 or 0.1 to 3 mg/kg. In one case, the IL-6 antibody or antibody portion thereof is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

Another aspect provided herein are kits comprising an IL-6 antibody or antigen-binding portion or a composition comprising such an antibody or antigen-binding portion. A kit may include, in addition to the antibody or composition, diagnostic or therapeutic agents. A kit can also include instructions for use in a diagnostic or therapeutic method. In one case, the kit includes the antibody or a composition comprising it and a diagnostic agent that can be used in a method described herein. In another case, the kit includes the antibody or a composition comprising it and one or more therapeutic agents that can be used in a method described herein.

Diagnostic Methods of Use

Another aspect provided herein are diagnostic methods. The anti-IL-6 antibodies or antigen binding portion thereof can be used to detect IL-6 in a biological sample in vitro or in vivo. One aspect provides a method for diagnosing the presence or location of IL-6-expressing cells in a subject in need thereof, comprising the steps of injecting the antibody into the subject, determining the expression of IL-6 in the subject by localizing where the antibody has bound, comparing the expression in the subject with that of a normal reference subject or standard, and diagnosing the presence or location of the cells. The anti-IL-6 antibodies may also be used as a marker for inflammation and/or for the infiltration of immune cells, such as monocytes and T cells, into a tissue.

The anti-IL-6 antibodies can be used in any suitable immunoassay, including, without limitation, an ELISA, a RIA, flow cytometry, tissue immunohistochemistry, a Western blot or an immunoprecipitation. The anti-IL-6 antibodies or antigen binding portion thereof can be used to detect IL-6 from humans. In another case, the anti-IL-6 antibodies can be used to detect IL-6 from cynomolgus monkeys, rhesus monkeys and rodents, such as mice and rats.

Methods for detecting IL-6 in a biological sample generally comprise contacting the biological sample with an anti-IL-6 antibody or antigen binding portions thereof and detecting the bound antibody. In one case, the anti-IL-6 antibody or antigen binding portion thereof is directly labeled with a detectable label. In another case, the anti-IL-6 antibody (the first antibody) is unlabeled and a second antibody or other molecule that can bind the anti-IL-6 antibody is labeled. A second antibody is chosen that is able to specifically bind the particular species and class of the first antibody. For example, if the anti-IL-6 antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody are disclosed herein and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

IL-6 can also be assayed in a biological sample by a competition immunoassay utilizing IL-6 standards labeled with a detectable substance and an unlabeled anti-IL-6 antibody. In this assay, the biological sample, the labeled IL-6 standards and the anti-IL-6 antibody are combined and the amount of labeled IL-6 standard bound to the unlabeled antibody is determined. The amount of IL-6 in the biological sample is inversely proportional to the amount of labeled IL-6 standard bound to the anti-IL-6 antibody.

One can use such immunoassays for a number of purposes. For example, the anti-IL-6 antibodies or antigen binding portions thereof can be used to detect IL-6 in cultured cells. In one case, the anti-IL-6 antibodies or antigen binding portions thereof are used to determine the amount of IL-6 on the surface of cells that have been treated with various compounds. This method can be used to identify compounds that modulate IL-6 protein levels. According to this method, one sample of cells is treated with a test compound for a period of time while another sample is left untreated. If the total IL-6 expression is to be measured, the cells are lysed and the total IL-6 expression is measured using any suitable immunoassay. The total IL-6 expression in the treated versus the untreated cells is compared to determine the effect of the test compound.

Immunoassays for measuring total IL-6 expression include flow cytometry and immunohistochemistry. If the cell surface IL-6 expression is to be measured, the cells are not lysed, and the cell surface levels of IL-6 are measured using one of the immunoassays described above. A preferred immunoassay for determining cell surface levels of IL-6 includes the steps of labeling the cell surface proteins with a detectable label, such as biotin or $^{125}$I, immunoprecipitating the IL-6 with an anti-IL-6 antibody and then detecting the labeled IL-6.

Another immunoassay for determining the localization of IL-6, e.g., cell surface levels, is by using immunohistochemistry. An immunoassay to detect cell surface levels of IL-6 includes binding of an anti-IL-6 antibody labeled with an appropriate fluorophore, such as fluorescein or phycoerythrin, and detecting the primary antibody using flow cytometry. In another example, the anti-IL-6 antibody is unlabeled and a second antibody or other molecule that can bind the anti-IL-6 antibody is labeled. Methods such as ELISA, RIA, flow cytometry, Western blot, immunohistochemistry, cell surface labeling of integral membrane proteins and immunoprecipitation are well known in the art. See, e.g., Harlow and Lane. In addition, the immunoassays can be scaled up for high throughput screening in order to test a large number of compounds for either activation or inhibitors of IL-6.

The anti-IL-6 antibodies or antigen binding portions thereof also can be used to determine the levels of IL-6 in a tissue or in cells derived from the tissue. In some examples, the tissue is a diseased tissue or a tissue biopsy. The tissue or biopsy can be used in an immunoassay to determine, e.g., total IL-6 expression, cell surface levels of IL-6 or localization of IL-6 by the methods discussed above. Such methods can be used to determine whether a tissue expresses high levels of IL-6, which could be indicative that the tissue is a target for treatment with anti-IL-6 antibody.

IL-6 antibodies and antigen-binding portios thereof also can be used in vivo to identify tissues and organs that express IL-6. In some cases, the anti-IL-6 antibodies are used to identify IL-6-expressing cells. Human anti-IL-6 antibodies may safely be used in vivo without eliciting a substantial immune response to the antibody upon administration, unlike antibodies of non-human origin or with humanized or chimeric antibodies.

The method comprises the steps of administering a detectably labeled anti-IL-6 antibody or a composition comprising them to a patient in need of such a diagnostic test and subjecting the patient to imaging analysis to determine the location of the IL-6-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radioisotopes, such as $^{99}$Tc. In another case, the anti-IL-6 antibody will be unlabeled and will be imaged by administering a second antibody or other molecule that is detectable and that can bind the anti-IL-6 antibody. In one example, a biopsy is obtained from the patient to determine whether the tissue of interest expresses IL-6.

The detectably labeled anti-IL-6 may comprise a fluorophore. In certain cases, the fluorophore is selected from the group consisting of a near-infrared fluorescent dye, dinitrophenyl, fluorescein and derivatives thereof, rhodamine, derivatives of rhodamine, phycoerythrin, phycocyanin, allophycocyanin, o-phthaldehyde and fluorescamine, Texas red, Rhodamine green, Oregon green, Cascade blue, phycoerythrin, CY3, CY5, CY2, CY7, coumarin, infrared 40, MR 200, IRD 40, Alexa Fluor, Cascade Blue, Tetramethylrhodamine, Pacific Blue, SYBR, and BODIPY. In another example, the fluorophore includes one of the following compounds with their emission maxima indicated in nm in parentheses, Cy2™. (506), GFP (Red Shifted) (507), YO-PRO®-1 (509), YOYO®-1 (509), Calcein (517), FITC (518), Fluor X® (519), Alexa® (520), Rhodamine 110 (520), 5-FAM (522), Oregon Green® 500 (522), Oregon Green® 488 (524), RiboGreen® (525), Rhodamine Green® (527), Rhodamine 123 (529), Magnesium Green® (531), Calcium Green® (533), TO-PRO®-1 (533), TOTO®-1 (533), JOE (548), BODIPY® 530/550 (550), DiI (565), BODIPY® (568), BODIPY® 558/568 (568), BODIPY® 564/570 (570), Cy3® (570), Alexa® 546 (570), TRITC (572), Magnesium Orange® (575), Phycoerythrin R&B (575), Rhodamine Phalloidin (575), Calcium Orange® (576), Pyronin Y (580), Rhodamine B (580), TAMRA (582), Rhodamine Red® (590), Cy3.5® (596), ROX (608), Calcium Crimson™ (615), Alexa® 594 (615), Texas Red® (615), Nile Red (628), YO-PRO®-3 (631), YOYO®-3 (631), R-phycocyanin (642), C-Phycocyanin (648), TO-PRO®-3 (660), TOTO®-3 (660), DiD DiIC(5) (665), Cy5™ (670), Thiadicarbocyanine (671) and Cy5.5 (694).

In yet a further example, the anti-IL-6 antibodies may also be used to determine the reduction in surface cell expression of IL-6 on cells, for example, lymphocytes or monocytes.

Human anti-IL-6 antibodies or antigen-binding portions thereof minimize the immunogenic and allergic responses intrinsic to non-human or non-human-derivatized monoclonal antibodies (Mabs), and thus increase the efficacy and safety of the administered antibodies or antigen-binding portions thereof.

Another aspect provides human anti-IL-6 antibodies encoded in part by a human germline sequence. The $V_H$, $V_K$, $V_\lambda$ genes are classified into families on the basis of sequence homology. Two $V_H$, $V_K$, or $V_\lambda$ genes belong to the same family if they share the same nucleotide sequence at more than 80% of the positions. An anti-IL-6 antibody may comprise a human kappa light chain ($V_K$) or a human lambda light chain ($V_\lambda$) or an amino acid sequence derived therefrom. In some cases comprising a lambda light chain, the light chain variable domain ($V_L$) is encoded in part by a human $V_\lambda 1$, $V_\lambda 2$, $V_\lambda 3$, $V_\lambda 4$, $V_\lambda 5$, $V_\lambda 6$, $V_\lambda 7$, $V_\lambda 8$, $V_\lambda 9$, or $V_\lambda 10$ family gene (Williams S. C. et al. *J. Mol. Bio.* 264:220-232, 1996). In some cases comprising a kappa light chain, the light chain variable domain ($V_L$) is encoded in part by a human $V_K I$, $V_K II$, $V_K III$, $V_K IV$, $V_K V$, or $V_K VI$ family gene (Cox J. P. L., et al, *Eur. J. Immunol* 24:827-836, 1994), preferably a $V_K I$, $V_K II$, $V_K III$, or $V_K IV$ family gene, and preferably a $V_K I$ or $V_K VI$ family gene. In some cases, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain cases, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. An anti-IL-6 antibody may comprise a heavy chain variable domain ($V_H$) encoded by a human $V_H 1$, $V_H 2$, $V_H 3$, $V_H 4$, $V_H 5$, $V_H 6$ or $V_H 7$ family gene. In particular examples, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81. In particular cases, the light chain variable region and/or heavy chain variable region comprises a framework region or at least a portion of a framework region (e.g., containing 2 or 3 subregions, such as FR2 and FR3). In certain cases, at least FRL1, FRL2, FRL3, or FRL4 is fully human. In other examples, at least FRH1, FRH2, FRH3, or FRH4 is fully human. In some cases, at least FRL1, FRL2, FRL3, or FRL4 is a germline sequence (e.g., human germline) or comprises human consensus sequences for the particular framework (readily available at the sources of known human Ig sequences described herein). In other examples, at least FRH1, FRH2, FRH3, or FRH4 is a germline sequence (e.g., human germline) or comprises human consensus sequences for the particular framework.

The $V_L$ of the IL-6 antibody may comprise one or more amino acid substitutions relative to the germline amino acid sequence of the human gene. In some cases, the $V_L$ of the IL-6 antibody comprises 1, 2, 3, 4, 5, 6, 7, 8, 9, or 10 amino acid substitutions relative to the germline amino acid sequence. In an example, one or more of those substitutions from germline is in the CDR regions of the light chain. In one example, the amino acid substitutions relative to germline are at one or more of the same positions as the substitutions relative to germline in any one or more of the $V_L$ of antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1. For example, the $V_L$ of an IL-6 antibody may contain one or more amino acid substitutions compared to germline found in the $V_L$ of antibody 9C8 IgG1. In some cases, the amino acid changes are at one or more of the same positions, but involve a different substitution than in the reference antibody.

In some cases, amino acid changes relative to germline occur at one or more of the same positions as in any of the $V_L$ of antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1, but the changes may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline is serine, one may conservatively substitute threonine for serine at that position.

In some cases, the light chain of the human anti-IL-6 antibody comprises the $V_L$ amino acid sequence of antibody 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1 or the amino acid sequence having up to 1, 2, 3, 4, 5, 6, 7, 8, 9, or 10 conservative amino acid substitutions and/or a total of up to 3 non-conservative amino acid substitutions. In some cases, the light chain comprises the amino acid sequence from the beginning of the CDR1 to the end of the CDR3 of any one of the foregoing antibodies.

In some cases, the light chain may comprise CDR1, CDR2 and CDR3 regions independently selected from the light chain CDR1, CDR2 and CDR3, respectively, of the light chain of antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1, or CDR regions each having less than 4 or less than 3 conservative amino acid substitutions and/or a total of three or fewer non-conservative amino acid substitutions. In some cases, the light chain of the anti-IL-6 antibody comprises a light chain CDR1, CDR2, and CDR3, each of which are independently selected from the light chain CDR1, CDR2 and CDR3 regions of monoclonal antibody 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1. In certain cases, the light chain of the anti-IL-6 antibody comprises the light chain CDR1, CDR2 and CDR3 regions of an antibody comprising the amino acid sequence of the $V_L$ region of an antibody selected from 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1 or the CDR regions each having less than 4 or less than 3 conservative amino acid substitutions and/or a total of three or fewer non-conservative amino acid substitutions.

In some cases, the variable domain ($V_H$) is encoded, at least in part, by a human gene. In some cases, the $V_H$ sequence of the IL-6 antibody contains one or more amino acid substitutions, deletions or insertions (additions) relative to the germline amino acid sequence. In some cases, the variable domain of the heavy chain comprises 1, 2, 3, 4, 5, 6, 7, 8, 9, 10, 11, 12, 13, 14, 15, 16, or 17 mutations from the germline amino acid sequence. In some cases, the mutation(s) are non-conservative substitutions, deletions or insertions, compared to the germline amino acid sequence. In some examples, the mutations are in the CDR regions of the heavy chain. In some examples, the amino acid changes are made at one or more of the same positions as the mutations from germline in any one or more of the $V_H$ of antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1. In other examples, the amino acid changes are at one or more of the same positions but involve a different mutation than in the reference antibody.

In some cases, the heavy chain comprises the $V_H$ amino acid sequence of antibody 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1 the $V_H$ amino acid sequence having up to 1, 2, 3, 4, 6, 8, or 10 conservative amino acid substitutions and/or a total of up to 3 non-conservative amino acid substitutions. In some examples, the heavy chain comprises the amino acid sequence from the beginning of the CDR1 to the end of the CDR3 of any one of the foregoing antibodies.

In some cases, the heavy chain comprises the heavy chain CDR1, CDR2 and CDR3 regions of antibody 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1 or the CDR regions each having less than 8, less than 6, less than 4, or less than 3 conservative amino acid substitutions and/or a total of three or fewer non-conservative amino acid substitutions.

In some cases, the heavy chain CDR regions are independently selected from the CDR regions of antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1. In other cases, the heavy chain comprises CDR regions independently selected from two or more $V_H$ regions selected from 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I124V N68T T83S IgG2 and 22B5 IgG1.

In other cases, the antibody comprises a light chain and a heavy chain. In a further example, the light chain CDRs and the heavy chain CDRs are from the same antibody.

One type of amino acid substitution that may be made is to change one or more cysteines in the antibody, which may be chemically reactive, to another residue, such as, without limitation, alanine or serine. In one example, there is a substitution of a non-canonical cysteine. The substitution can be made in a CDR or framework region of a variable domain or in the constant domain of an antibody. In some cases, the cysteine is canonical.

Another type of amino acid substitution that may be made is to change any potential proteolytic sites in the antibody. Such sites may occur in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues.

In certain cases, the heavy and light chains of the IL-6 antibodies may optionally include a signal sequence.

In some cases, the antibody comprises the heavy and light chain variants of monoclonal antibodies 9C8 IgG1, 9C8 IgG2, 9C8 N68T T83S IgG1, 9C8 N68T T83S IgG2, 9C8 E31G N68T T83S IgG1, 9C8 E31G N68T T83S IgG2, 9C8 I124V N68T T83S IgG1, 9C8 I24V N68T T83S IgG2 and 22B5 IgG1. As discussed in greater detail in EXAMPLE 3, numerous heavy and light chain variant mutations were made to match those in the germline CDR regions. The specific amino acids that were mutated to arrive at the germline versions are apparent to those of skill in the art by comparing the sequences of the germline vs. a non-germline antibody. For example, one amino acid substitution is provided in the heavy chain of antibody 9C8, wherein an isoleucine at residue 24 is changed to a valine and is referred to as 9C8 I124V. A second exemplary amino acid substitution is in the light chain of antibody 9C8, and substitutes the lysine at residue 92 with an asparagine and is referred to as 9C8 K92N.

As will be appreciated, gene utilization analysis provides only a limited overview of antibody structure. As human B-cells stocastically generate V-D-J heavy or V-J kappa light chain transcripts, there are a number of secondary processes that occur, including, without limitation, somatic hypermutation, additions, and CDR3 extensions. Accordingly, to further examine antibody structures, predicted amino acid sequences of the antibodies were generated from the cDNAs obtained from the clones. In addition, N-terminal amino acid sequences were obtained through protein sequencing.

Class and Subclass of Anti-IL-6 Antibodies

The class (e.g., IgG, IgM, IgE, IgA, or IgD) and subclass (e.g. IgG1, IgG2, IgG3, or IgG4) of IL-6 antibodies may be determined by any suitable method. In general, the class and subclass of an antibody may be determined using antibodies that are specific for a particular class and subclass of antibody. Such antibodies are commercially available. The class and subclass can be determined by ELISA, or Western Blot, as well as other techniques.

Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. The IL-6 antibodies can be an IgG, an IgM, an IgE, an IgA, or an IgD molecule. For example, the IL-6 antibodies can be an IgG that is an IgG1, IgG2, IgG3, or an IgG4 subclass. In one example, the IL-6 antibodies are IgG2 subclass. In another example, the IL-6 antibodies are IgG1 subclass.

In one aspect methods are provided for converting the class or subclass of an IL-6 antibody to another class or subclass. In some cases, a nucleic acid molecule encoding a $V_L$ or $V_H$ that does not include sequences encoding $C_L$ or $C_H$ is isolated using any suitable methods. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an IL-6 antibody that was originally IgM can be class switched to an IgG. Further, the class switching may be used to convert one IgG subclass to another, e.g., from IgG1 to IgG2. Another method for producing an antibody comprising a desired isotype comprises the steps of isolating a nucleic acid encoding a heavy chain of an IL-6 antibody and a nucleic acid encoding a light chain of an IL-6 antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the IL-6 antibody with the desired isotype.

Binding Affinity of IL-6 Antibodies to IL-6

The binding affinity and dissociation rate of an anti-IL-6 antibody to IL-6 can be determined by any suitable method. The binding affinity can be measured by ELISAs, RIAs, flow cytometry, and surface plasmon resonance, such as BIACORE™. The dissociate rate can be measured by surface plasmon resonance. One can determine whether an antibody has substantially the same $K_D$ as an anti-IL-6 antibody by using any suitable method. Example 7 exemplifies a method for determining affinity constants of anti-IL-6 monoclonal antibodies.

Identification of IL-6 Epitopes Recognized by Anti-IL-6 Antibodies

One can determine whether an antibody binds to the same epitope or cross-competes for binding with an IL-6 antibody by using any suitable method. In one example, one allows an IL-6 antibody to bind to IL-6 under saturating conditions and then measures the ability of the test antibody to bind to IL-6. If the test antibody is able to bind to IL-6 at the same time as the IL-6 antibody, then the test antibody binds to a different epitope as the IL-6 antibody. However, if the test antibody is not able to bind to IL-6 at the same time, then the test antibody binds to the same epitope, an overlapping epitope, or an epitope that is in close proximity to the epitope bound by the human IL-6 antibody. This experiment can be performed using an ELISA, a RIA, BIACORE™, or flow cytometry (FACS).

To test whether an IL-6 antibody cross-competes with another IL-6 antibody, one may use the competition method described herein in two directions, i.e., determining if the reference antibody blocks the test antibody and vice versa. In one example, the experiment is performed using an ELISA.

Methods of Producing Antibodies

IL-6 antibodies or antigen-binding portions thereof can be produced by a variety of techniques, including conventional monoclonal antibody methodology, for example the standard somatic cell hybridization technique of Kohler and Milstein (1975) Nature 256: 495. Other techniques for producing monoclonal antibodies can also be employed such as viral or oncogenic transformation of B lymphocytes.

An exemplary animal system for preparing hybridomas is a murine system. Immunization protocols and techniques for isolation of immunized splenocytes for fusion are known in the art. Fusion partners (e.g., murine myeloma cells) and fusion procedures are also known.

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539, and U.S. Pat. Nos. 5,530,101; 5,585,089; 5,693,762; and 6,180,370).

In one case, the anti-IL-6 antibodies are human monoclonal antibodies. Such human monoclonal antibodies directed against IL-6 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994); reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; U.S. Pat. No. 5,545,807; PCT Publication Nos.: WO 92/03918, WO 93/12227, WO 94/25585, WO 97/13852, WO 98/24884 and WO 99/45962; and PCT Publication No. WO 01/14424.

In another aspect, human anti-IL-6 antibodies can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication No. WO 02/43478.

Still further, alternative transgenic animal systems expressing human immunoglobulin genes are available in the art and can be used to raise IL-6 antibodies. For example, an alternative transgenic system referred to as the Xenomouse™ (Abgenix, Inc.) can be used; such mice are described in, for example, U.S. Pat. Nos. 5,939,598; 6,075,181; 6,114,598; 6,150,584; and 6,162,963.

Moreover, alternative transchromosomic animal systems expressing human immunoglobulin genes are available in the art and can be used to raise IL-6 antibodies. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise IL-6 antibodies.

Human monoclonal antibodies can also be prepared using SCID mice into which human immune cells have been reconstituted such that a human antibody response can be generated upon immunization. Such mice are described in, for example, U.S. Pat. Nos. 5,476,996; and 5,698,767.

Immunization of Human Ig Mice

Production of Antibodies and Antibody-Producing Cell Lines

After immunization of an animal with an IL-6 antigen, antibodies and/or antibody-producing cells can be obtained from the animal. In some cases, IL-6 antibody-containing serum is obtained from the animal by bleeding or sacrificing the animal. The serum may be used as it is obtained from the animal, an immunoglobulin fraction may be obtained from the serum, or the IL-6 antibodies may be purified from the serum.

In some cases, antibody-producing immortalized cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. If fusion with myeloma cells is used, the myeloma cells preferably do not secrete immunoglobulin polypeptides (a non-secretory cell line). Immortalized cells are screened using IL-6, a portion thereof, or a cell expressing IL-6. In some cases, the initial screening is performed using an enzyme-linked immunoassay (ELISA) or a radioimmunoassay. An example of ELISA screening is provided in PCT Publication No. WO 00/37504, incorporated herein by reference.

IL-6 antibody-producing cells, e.g., hybridomas, are selected, cloned and further screened for desirable characteristics, including robust growth, high antibody production and desirable antibody characteristics. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In one example, the immunized animal is a non-human animal that expresses human immunoglobulin genes and the splenic B cells are fused to a myeloma cell line from the same species as the non-human animal. One such immunized animal is a Kirin TC Mouse™ mouse and the myeloma cell line is a non-secretory mouse myeloma. In a further example the myeloma cell line is Sp2/0-Ag14 (American Type Culture Collection (ATCC) CRL-1581).

Also provided are methods for producing a cell line that produces a human monoclonal antibody or a antigen-binding portion thereof directed to IL-6 comprising: (a) immunizing a non-human transgenic animal described herein with IL-6, a portion of IL-6 or a cell or tissue expressing 11-6; (b) allowing the transgenic animal to mount an immune response to IL-6; (c) isolating antibody-producing cells from the transgenic animal; (d) immortalizing the antibody-producing cells; (e) creating individual monoclonal populations of the immortalized antibody-producing cells; and (f) screening the immortalized antibody-producing cells to identify an antibody directed to IL-6.

In another aspect, hybridomas are provided that produce a human IL-6 antibody. The human IL-6 antibody produced by the hybridoma may be an antagonist of IL-6. The hybridomas may be produced in a non-human, non-mouse species such as, for example, rats, sheep, pigs, goats, cattle or horses.

In one case, antibody-producing cells are isolated and expressed in a host cell, for example myeloma cells. In still another example, a transgenic animal is immunized with IL-6, primary cells (e.g., spleen or peripheral blood cells) are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al. (1996) Proc. Natl. Acad. Sci. USA 93: 7843-48, incorporated herein by reference. IL-6 antibodies may then be identified and isolated.

Recombinant Methods of Producing Antibodies

IL-6 antibodies or antigen-binding portions thereof can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Various recombinant DNA methodologies are used to obtain antibody heavy and light chain genes, to incorporate these genes into recombinant expression vectors and to introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397, the disclosures of which are incorporated herein by reference.

Mutations and Modifications

To express the IL-6 antibodies, DNA fragments encoding $V_H$ and $V_L$ regions can first be obtained using any of the methods discussed herein. Various mutations, deletions, and/or additions can also be introduced into the DNA sequences using various suitable methods. For example, mutagenesis can be carried out using standard methods, such as PCR-mediated mutagenesis, in which the mutated nucleotides are incorporated into the PCR primers such that the PCR product contains the desired mutations or site-directed mutagenesis. One type of substitution, for example, that may be made is to change one or more cysteines in the antibody, which may be chemically reactive, to another residue, such as, without limitation, alanine or serine. For example, there can be a substitution of a non-canonical or canonical cysteine. The substitution can be made in a CDR or framework region of a variable domain or in the constant domain of an antibody. The antibodies may also be mutated in the variable domains of the heavy and/or light chains, e.g., to alter a binding property of the antibody. For example, a mutation may be made in one or more of the CDR regions to increase or decrease the $K_D$ of the antibody for IL-6, to increase or decrease $k_{off}$, or to alter the binding specificity of the antibody. Techniques in site-directed mutagenesis include, for example, Sambrook et al. and Ausubel et al., which are incorporated herein by reference.

A mutation may also be made in a framework region or constant domain to increase the half-life of an IL-6 antibody. See, e.g., PCT Publication No. WO 00/09560, incorporated herein by reference. A mutation in a framework region or constant domain can also be made to alter the immunogenicity of the antibody, to provide a site for covalent or non-covalent binding to another molecule, or to alter such properties as complement fixation, FcR binding and antibody-dependent cell-mediated cytotoxicity (ADCC). A single antibody may have mutations in any one or more of the CDRs or framework regions of the variable domain or in the constant domain.

In a process known as "germlining", certain amino acids in the $V_H$ and $V_L$ sequences can be mutated to match those found naturally in germline $V_H$ and $V_L$ sequences. In particular, the amino acid sequences of the framework regions in the $V_H$ and $V_L$ sequences can be mutated to match the germline sequences to reduce the risk of immunogenicity when the antibody is administered. Germline DNA sequences for human $V_H$ and $V_L$ genes are known in the art (see e.g., the "Vbase" human germline sequence database; see also Kabat, E. A., et al. (1991) Sequences of Proteins of Immunological Interest, Fifth Edition, U.S. Department of Health and Human Services, NIH Publication No. 91-3242; Tomlinson et al. (1992) J. Mol. Biol. 227:776-798; and Cox et al. Eur. J. Immunol. 24:827-836 (1994); the contents of each of which are incorporated herein by reference).

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an IL-6 antibody can be cleaved. In various examples, the heavy and light chains of the IL-6 antibodies may optionally include a signal sequence. In some cases, the C-terminal lysine of the heavy chain of the anti-IL-6 antibody may be proteolytically cleaved.

Once DNA fragments encoding the $V_H$ and $V_L$ segments are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG1 constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al. Science 242:423-426 (1988); Huston et al. Proc. Natl. Acad. Sci. USA 85:5879-5883 (1988); McCafferty et al., Nature 348:552-554 (1990)). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to IL-6 and to another molecule.

In another case, a fusion antibody may be made that comprises all or a portion of an IL-6 antibody linked to another polypeptide. In another case, only the variable domains of the IL-6 antibody are linked to the polypeptide. In another case, the $V_H$ domain of an IL-6 antibody is linked to a first polypeptide, while the $V_L$ domain of an IL-6 antibody is linked to a second polypeptide that associates with the first polypeptide in a manner such that the $V_H$ and $V_L$ domains can interact with one another to form an antigen binding site. In another case, the $V_H$ domain is separated from the $V_L$ domain by a linker such that the $V_H$ and $V_L$ domains can interact with one another. The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other cases, other modified antibodies may be prepared using IL-6 antibody encoding nucleic acid molecules. For instance, "Kappa bodies" (Ill et al., Protein Eng. 10: 949-57 (1997)), "Minibodies" (Martin et al., EMBO J. 13: 5303-9 (1994)), "Diabodies" (Holliger et al., Proc. Natl. Acad. Sci. USA 90: 6444-6448 (1993)), or "Janusins" (Traunecker et al., EMBO J. 10:3655-3659 (1991) and Traunecker et al., Int. J. Cancer (Suppl.) 7:51-52 (1992)) may be prepared using suitable molecular biological techniques following the teachings discussed herein.

Bispecific antibodies or antigen-binding fragments can be produced by a variety of methods including fusion of hybridomas or linking of Fab' fragments. See, e.g., Songsivilai & Lachmann, Clin. Exp. Immunol. 79:315-321 (1990), Kostelny et al., J. Immunol. 148:1547-1553 (1992). In addition, bispecific antibodies may be formed as "diabodies" or "Janusins." In some cases, the bispecific antibody binds to two different epitopes of IL-6. In some cases, the modified antibodies described herein are prepared using one or more of the variable domains or CDR regions from a human IL-6 antibody.

Vectors and Host Cells

To express IL-6 antibodies and antigen-binding portions thereof, DNAs encoding partial or full-length light and heavy chains, obtained as described herein, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. Expression vectors include, for example, plasmids, retroviruses, adenoviruses, adeno-associated viruses (AAV), plant viruses such as cauliflower mosaic virus, tobacco mosaic virus, cosmids, YACs, and EBV derived episomes. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or both genes are inserted into the same expression vector. The antibody genes are inserted into the expression vector by various methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The design of the expression vector, including the selection of regulatory sequences may depend on such factors as the choice of the host cell to be transformed, the level of expression of protein desired. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615, incorporated herein by reference. Methods for expressing antibodies in plants, including a description of promoters and vectors, as well as transformation of plants is known in the art. See, e.g., U.S. Pat. No. 6,517,529, incorporated herein by reference.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification), the neomycin phosphotransferase gene (for G418 selection), and the glutamate synthetase gene.

Nucleic acid molecules encoding IL-6 antibodies and vectors comprising these nucleic acid molecules can be used for transfection of a suitable mammalian, plant, bacterial or yeast host cell. Transformation can be any suitable method for introducing polynucleotides into a host cell. Methods for introduction of heterologous polynucleotides into mammalian cells include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, for example, Chinese hamster ovary (CHO) cells, NSO cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using various protein purification methods. Bacterial host cells include *E. coli* and *Streptomyces* species. Yeast host cells include *Schizosaccharomyces pombe, Saccharomyces cerevisiae* and *Pichia pastoris*.

Further, expression of antibodies from production cell lines can be enhanced using any suitable techniques. For example, the glutamine synthetase (the GS system) and DHFR gene expression systems are common approaches for enhancing expression under certain conditions. High expressing cell clones can be identified using conventional techniques, such as limited dilution cloning and Microdrop technology. The GS system is discussed in European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the present disclosure, regardless of the glycosylation of the antibodies.

Phage Display Libraries

Also provided are methods for producing an IL-6 antibody or antigen-binding portion thereof comprising the steps of synthesizing a library of human antibodies on phage, screening the library with IL-6 or a portion thereof, isolating phage that bind IL-6, and obtaining the antibody from the phage. By way of example, one method for preparing the library of antibodies for use in phage display techniques comprises the steps of immunizing a non-human animal comprising human immunoglobulin loci with IL-6 or an antigenic portion thereof to create an immune response, extracting antibody-producing cells from the immunized animal; isolating RNA encoding heavy and light chains of antibodies from the extracted cells, reverse transcribing the RNA to produce cDNA, amplifying the cDNA using primers, and inserting the cDNA into a phage display vector such that antibodies are expressed on the phage. Recombinant IL-6 antibodies may be obtained in this way.

Recombinant IL-6 human antibodies can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85 (1992); Huse et al., Science 246:1275-1281 (1989); McCafferty et al., Nature 348:552-554 (1990); Griffiths et al., EMBO J. 12:725-734 (1993); Hawkins et al., J. Mol. Biol. 226:889-896 (1992); Clackson et al., Nature 352:624-628 (1991); Gram et al., Proc. Natl. Acad. Sci. USA 89:3576-3580 (1992); Garrad et al., Bio/Technology 9:1373-1377 (1991); Hoogenboom et al., Nuc. Acid Res. 19:4133-4137 (1991); and Barbas et al., Proc. Natl. Acad. Sci. USA 88:7978-7982 (1991), all incorporated herein by reference.

To isolate and produce human IL-6 antibodies with the desired characteristics, a human IL-6 antibody is first used to select human heavy and light chain sequences having similar binding activity toward IL-6, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., Nature 348:552-554 (1990); and Griffiths et al., EMBO J. 12:725-734 (1993), all incorporated herein by reference.

Once initial human $V_L$ and $V_H$ domains are selected, "mix and match" experiments are performed, in which different pairs of the initially selected $V_L$ and $V_H$ segments are screened for IL-6 binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to IL-6.

Following screening and isolation of an IL-6 antibody from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms, as described herein. To express a recombinant human antibody isolated by screening of a combinatorial library, the DNA encoding the antibody is cloned into a recombinant expression vector and introduced into mammalian host cells, as described above.

Deimmunized Antibodies

In another aspect, the IL-6 antibodies or antigen binding portions thereof may be deimmunized to reduce their immunogenicity using the techniques described in, e.g., PCT Publication Nos.: WO98/52976 and WO00/34317 (incorporated herein by reference).

Derivatized and Labeled Antibodies

An IL-6 antibody or antigen-binding portion can be derivatized or linked to another molecule (e.g., another peptide or protein). In general, the antibodies or antigen-binding portion thereof are derivatized such that the IL-6 binding is not affected adversely by the derivatization or labeling. Accordingly, the antibodies and antigen-binding portions are intended to include both intact and modified forms of the human IL-6 antibodies described herein. For example, an antibody or antigen-binding portion can be functionally linked (by chemical coupling, genetic fusion, noncovalent association or otherwise) to one or more other molecular entities, such as another antibody (e.g., a bispecific antibody or a diabody), a detection agent, a label, a cytotoxic agent, a pharmaceutical agent, and/or a protein or peptide that can mediate association of the antibody or antigen-binding portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion may be derivatized include fluorescent compounds, including, for example, fluorescein, fluorescein isothiocyanate, rhodamine, 5-dimethylamine-1-naphthalenesulfonyl chloride, phycoerythrin, lanthanide phosphors. An antibody can also be labeled with enzymes that are useful for detection, such as, for example, horseradish peroxidase, β-galactosidase, luciferase, alkaline phosphatase, or glucose oxidase. When an antibody is labeled with a detectable enzyme, it is detected by adding additional reagents that the enzyme uses to produce a reaction product that can be discerned. For example, when the agent horseradish peroxidase is present the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some cases, labels are attached by spacer arms of various lengths to reduce potential steric hindrance. An IL-6 antibody can also be derivatized with a chemical group such as polyethylene glycol (PEG), a methyl or ethyl group, or a carbohydrate group. These groups are useful to improve the biological characteristics of the antibody, e.g., to increase serum half-life.

The specific Examples set forth herein are intended to illustrate particular aspects of the disclosure and are not intended to limit the scope of the claims.

EXAMPLE 1

Generation of Hybridomas Producing Anti-IL-6 Antibody

Exemplary antibodies in accordance with the disclosure were prepared, selected, and assayed as follows:
Mouse Strains Fully human monoclonal antibodies to human IL-6 were prepared using human Ig transgenic mouse strains HCo7 and HCo12, as well as the human transchromosomal/transgenic strain, KM (Medarex, Inc.). These strains all express fully human antibodies that are indistinguishable from antibodies isolated from humans.

In all three strains, both the endogenous mouse kappa light chain gene and the endogenous mouse heavy chain gene have been homozygously disrupted as described in Chen et al. (1993) EMBO J. 12:811-820 and in Example 1 of PCT Publication WO 01/09187, respectively. Moreover, all three carry a human kappa light chain transgene, KCo5, as described in Fishwild et al. (1996) Nature Biotechnology 14:845-851. In contrast, the three strains are distinct with respect to their human heavy chain genes. The HCo7 strain carries the HCo7 human heavy chain transgene as described in U.S. Pat. Nos. 5,545,806, 5,625,825, and 5,545,807; the HCo12 strain carries the HCo12 human heavy chain transgene as described in Example 2 of PCT Publication WO 01/09187; and the KM strain carries a human mini-chromosome as described in Ishida et al., (2002), Cloning and Stem Cells, 4: 91-102.
Immunization with IL-6 Antigen and Selection of HuMab Mice Producing Anti-IL-6 Monoclonal Antibodies General immunization schemes for HuMab mice are described in Lonberg et al (1994) Nature 368(6474): 856-859; Fishwild et al. (1996) Nature Biotechnology 14: 845-851 and PCT Publication WO 98/24884. In the present case, a total of 81 HuMab mice of the HCo7, HCo12 and KM strains were immunized beginning at 6-16 weeks of age with 5-25 µgs of purified human IL-6 in Ribi adjuvant. Human IL-6 was isolated from a human bone marrow-derived stromal cell, HS-5 (ATCC CRL-11882, Roecklein B. A. & Torok-Storb B., *Blood* 85: 997-1005, 1995), which endogenously secretes IL-6 into the media. Human IL-6 was purified from IL-6 expressing HS-5 media, which was concentrated by ultrafiltration followed by a Q Sepharose anion exchange chromatography step and an affinity chromatography step using a mouse anti-hIL-6 MAb (R&D Systems, Catalog number MAB2061, clone 1936). The purified human IL-6 had a purity of about 90% by SDS-PAGE. The major bands were excised from the SDS-PAGE gel, digested with trypsin and the extracted gel purified tryptic peptides were analyzed via MALDI/MS on the 4700 TOF/TOF Proteomics Analyzer and were confirmed to be human IL-6. Alternatively, one can use recombinant human IL-6 from commercial sources (for example, Recombinant Human IL-6, catalog number 206-IL-6/CF. R&D System Inc. 614 Mckinley Place Nebr., Minneapolis, Minn. 55413). Administration was via injection intraperitoneally, subcutaneously or into the footpad at 3-14 day intervals, up to a total of 8 immunizations. Immune response was monitored via ELISA screening, as described below.
Selection of HuMab Mice Producing Anti-IL-6 Antibodies Blood from the transgenic mice described above was obtained via retro-orbital bleeds and analyzed by ELISA for specific binding to purified human IL-6 recombinant protein, as described by Fishwild et al. (1996), Nature Biotechnology 14: 845-851.

Briefly, microtiter plates were coated using 50 µl/well of a purified recombinant IL-6 solution containing 1 µg/ml in PBS, and incubated overnight at 4° C. The wells were then blocked using 200 μl/well of 5% chicken serum in PBS/Tween (0.05%). Dilutions of plasma from IL-6-immunized mice were added to each well and incubated for 1 hour at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Moss Inc, product #: ABTS-1000 mg/ml) and analyzed by spectrophotometer at OD 415-495. Mice that developed the highest titers of anti-IL-6 antibodies (22 animals total) were used for fusions. Generation of Hybridomas Producing Human Monoclonal Antibodies to IL-6:

The mice selected above were boosted intravenously with IL-6 at 3 days and then again at 2 days prior to sacrifice and removal of the spleen and/or lymph nodes. A total of 17 fusions were performed.

The mouse splenocytes and/or lymph node lymphocytes isolated from immunized HuMab or KM mice, were fused to SP2/0 non-secreting mouse myeloma cells (ATCC, CRL-1581, ATCC American Type Culture Collection, 1080 University Boulevard, Manassas, Va. 20110-2209 USA) using electrofusion (E-fusion, Cyto Pulse™ technology, Cyto Pulse™ Sciences, Inc., Glen Burnie, Md.), according to standard or manufacturer-recommended protocols.

Briefly, single cell suspensions of splenocytes and/or lymph node lymphocytes from immunized mice were prepared and then combined with an equal number of Sp2/0 non-secreting mouse myeloma cells; E-fusion was then performed.

The cells were then plated at $2 \times 10^4$ cells/well in flat bottom microtiter plate, and incubated for 10-14 days in selective medium containing 10% fetal bovine serum, 10% P388D1 (ATCC, CRL-TIB-63) conditioned medium, 3-5% (IGEN) in DMEM (Mediatech, Herndon, Va., Cat. No. CRL 10013, with high glucose, L-glutamine and sodium pyruvate), 5 mM HEPES, 0.055 mM 2-mercaptoethanol, 50 mg/ml gentamycin and 1×HAT (Sigma, Cat. No. CRL-P-7185).

After 1-2 weeks, cells were cultured in medium in which the HAT was replaced with HT. Approximately 10-14 days after cell plating supernatants from individual wells were screened for the presence of human gamma, kappa antibodies. The supernatants which scored positive for human gamma, kappa were then screened by ELISA (using the protocol described above) for human anti-IL-6 monoclonal IgG antibodies. The antibody-secreting hybridomas were transferred to 24 well plates, screened again and, if confirmed positive for human anti-IL-6 IgG monoclonal antibodies, were subcloned at least twice by limiting dilution. The stable subclones were then cultured in vitro to generate small amounts of antibody in tissue culture medium for further characterization.

EXAMPLE 2

Sequencing of IL-6 Antibodies

Full-length anti-IL-6 antibodies were cloned and sequence verified from hybridomas as follows: Poly(A)$^+$ mRNA was isolated using an RNeasy Mini Kit (Qiagen) and cDNA synthesized from the mRNA with the Advantage RT-for-PCR kit (BD Biosciences) using oligo(dT) priming. The oligo(dT) primed cDNA for clone 9C8 was amplified using degenerate primers listed in Table 1 respectively.

TABLE 1

| Degenerate primers (5' to 3') for 9C8 | |
|---|---|
| VH4_5UTR_F | CTTTCTGAGASTCMTGGAKCTCMTG SEQ ID NO: 49 |
| G_3UTR_R | TACGTGCCAAGCATCCTCGC SEQ ID NO: 50 |
| VK1a_5UTR_F | GSARTCAGWCYCWVYCAGGACACAGC SEQ ID NO: 51 |
| K_3UTR_F | AGGCTGGAACTGAGGAGCAGGTG SEQ ID NO: 52 |

Amplification was achieved using the High Fidelity Polymerase (Roche) and a PTC-200 DNA Engine (MJ Research) with cycling as follows: 2'@95° C.; 25× (20"@95° C., 30"@52° C., 2'@72° C.); 10'@72° C. PCR amplicons were cloned into the pCR2.1 TOPO and transformed into TOP10 chemically competent cells (Invitrogen) using the standard protocol. Clones were sequence verified using Grills 16$^{th}$ BDTv3.1/dGTP chemistry (Applied Biosystems Inc) and a 3730×1 DNA Analyzer (Applied Biosystems Inc). All sequences were analyzed by alignments to the 'V BASE sequence directory' (Tomlinson, et al, *J. Mol. Biol.*, 227, 776-798 (1992); *Hum. Mol. Genet.*, 3, 853-860 (1994); *EMBO J.*, 14, 4628-4638 (1995). The germline gene segment usages of exemplary anti IL-6 antibodies are listed in Table 2.

TABLE 2

| | Heavy chain | | | Light chain | | |
|---|---|---|---|---|---|---|
| Clone | $V_H$ | D | $J_H$ | $V_K$ | $J_K$ | Subtype |
| 9C8 | 4-34 | — | 3b | L15 | JK1 | IgG1 |
| 22B5 | 4-34 | — | 3b | L15 | JK1 | IgG1 |

Full-Length Sequences of the ANTI-IL-6 Antibody Derived from Hybridomas 9C8

```
DNA sequence of 9C8 heavy chain from hybridoma cells
(variable domain in uppercase)
                                              SEQ ID NO: 1
CAGGTGCAGCTACAGCAGTGGGGCGCAGGACTGTTGAAGCCTTCGGAGACCCTGTCCCTCAC

CTGCGCTATCTATGGTGGGTCCTTCAGGGAGTACTACTGGAGCTGGATCCGCCAGCCCCCAG

GGAAGGGGCTGGAGTGGATTGGGGAAATCTTTCATAGTGGAAGCACCAACTACAACCCGTCC

CTCAAGAGTCGAGTCAACATATCAGTAGACACGTCCAAGAACCAGTTCTCCCTGAAGCTGAC

CTCTGTGACCGCCGCGGACACGGCTGTGTATTACTGTGCGAGAGAGGAATTAGATGATTTTG

ATATCTGGGGCCAAGGGACAATGGTCACCGTCTCTTCAgcctccaccaagggcccatcggtc ttccccctggcacctcctccaagagcacctctgggggcacagcggccctgggctgctggt
```

-continued caaggactacttccccgaaccggtgacggtgtcgtggaactcaggcgccctgaccagcggcg tgcacaccttcccggctgtcctacagtcctcaggactctactccctcagcagcgtggtgacc gtgccctccagcagcttgggcacccagacctacatctgcaacgtgaatcacaagcccagcaa caccaaggtggacaagagagttgagcccaaatcttgtgacaaaactcacacatgcccaccgt gcccagcacctgaactcctggggggaccgtcagtcttcctcttccccccaaaacccaaggac accctcatgatctcccggacccctgaggtcacatgcgtggtggtggacgtgagccacgaaga ccctgaggtcaagttcaactggtacgtggacggcgtggaggtgcataatgccaagacaaagc cgcgggaggagcagtacaacagcacgtaccgtgtggtcagcgtcctcaccgtcctgcaccag gactggctgaatggcaaggagtacaagtgcaaggtctccaacaaagccctcccagcccccat cgagaaaaccatctccaaagccaaagggcagccccgagaaccacaggtgtacaccctgcccc catcccgggatgagctgaccaagaaccaggtcagcctgacctgcctggtcaaaggcttctat cccagcgacatcgccgtggagtgggagagcaatgggcagccggagaacaactacaagaccac gcctcccgtgctggactccgacggctccttcttcctctacagcaagctcaccgtggacaaga gcaggtggcagcaggggaacgtcttctcatgctccgtgatgcatgaggctctgcacaaccac tacacgcagaagagcctctccctgtctccgggtaaa Derived protein sequence (by translation) of 9C8 heavy chain
from hybridoma cells (variable domain in uppercase)
                                               SEQ ID NO: 3
QVQLQQWGAGLLKPSETLSLTCAIYGGSFREYYWSWIRQPPGKGLEWIGEIFHSGSTNYNPS LKSRVNISVDTSKNQFSLKLTSVTAADTAVYYCAREELDDFDIWGQGTMVTVSSastkgpsv fplapssкstsggtaalgclvkdyfpepvtvswnsgaltsgvhtfpavlqssglyslssvvt vpssslgtqtyicnvnhkpsntkvdkrvepkscdkthtcppcpapellggpsvflfppkpkd tlmisrtpevtcvvvdvshedpevkfnwyvdgvevhnaktkpreeqynstyrvvsvltvlhq dwlngkeykckvsnkalpapiektiskakgqprepqvytlppsrdeltknqvsltclvkgfy psdiavewesngqpennykttppvldsdgsfflyskltvdksrwqqgnvfscsvmhealhnh ytqkslslspgk DNA sequence of 9C8 light chain from hybridoma cells
(variable domain in uppercase)
                                               SEQ ID NO: 12
GACATCCAGATGACCCAGTCTCCATCCTCACTGTCTGCATCTGTAGGAGACAGAGTCACCAT

CACTTGTCGGGCGAGTCAGGGTATTAGCAGCTGGTTAGCCTGGTATCAGCAGAAACCAGAGA

AAGCCCCTAAGTCCCTGATCTATGCTGCATCCAGTTTGCAAAGTGGGGTCCCATCAAGGTTC

AGCGGCAGTGGATCTGGGACAGATTTCACTCTCACCATCAGTAGCCTGCAGCCTGAAGATTT

TGCAACTTATTACTGCCAACAGTATAAAAGTTACCCTCGGACGTTCGGCCAAGGGACCAAGG

TGGAAATCAAAcgaactgtggctgcaccatctgtcttcatcttcccgccatctgatgagcag ttgaaatctggaactgcctctgttgtgtgcctgctgaataacttctatcccagagaggccaa agtacagtggaaggtggataacgccctccaatcgggtaactcccaggagagtgtcacagagc aggacagcaaggacagcacctacagcctcagcagcaccctgacgctgagcaaagcagactac gagaaacacaaagtctacgcctgcgaagtcacccatcagggcctgagctcgcccgtcacaaa gagcttcaacaggggagagtgt Derived protein sequence (by translation) of 9C8 light chain
from hybridoma cells (variable domain in uppercase)
SEQ ID NO: 14
DIQMTQSPSSLSASVGDRVTITCRASQGISSWLAWYQQKPEKAPKSLIYAASSLQSGVPSRF SGSGSGTDFTLTISSLQPEDFATYYCQQYKSYPRTFGQGTKVEIKrtvaapsvfifppsdeq lksgtasvvcllnnfypreakvqwkvdnalqsgnsqesvteqdskdstyslsstltlskady ekhkvyacevthqglsspvtksfnrgec ANTI-IL-6 Antibodies Variable Domains were Cloned into Expression Vectors as Follows:

The variable domains were amplified from pCR2.1 cloned cDNA using primers listed in Table 3. Amplification was achieved using the Pfx Platinum polymerase (Invitrogen) and a PTC-200 DNA Engine (MJ Research) with cycling as follows: 2'@94° C.; 20× (30"@94° C., 45"@55° C., 1'@68° C.); 5'@68° C. The variable domains were then cloned into expression vectors containing constant domains of the appropriate isotype. These clones were sequence verified using Grills 16$^{th}$ BDTv3.1/dGTP chemistry (Applied Biosystems Inc) and a 3730×1 DNA Analyzer (Applied Biosystems Inc).

TABLE 3

| Variable domain primers (5' to 3') for 9C8 | |
|---|---|
| H4_34 | ttacagtGCGCGCACTCCCAGGTGCAGCTACAGCAGTGG SEQ ID NO: 53 |
| K_O12 | ttacagtGTGCACTCCGACATCCAGATGACCCAGTCTCC SEQ ID NO: 54 |
| G1/2_ch1 (ApaI)_R | GAAGACCGATGGGCCCTTGG SEQ ID NO: 55 |
| JK1_R | tatattccttaattaagttattctactcacGTTTGATTT CCACCTTGGTCCCT SEQ ID NO: 56 |

Full-Length Sequences of Recombinant ANTI-IL-6 Antibodies 9C8

DNA sequence of recombinant 9C8 IgG2 heavy chain
(variable domain in uppercase)
SEQ ID NO: 23
CAGGTGCAGCTACAGCAGTGGGGCGCAGGACTGTTGAAGCCTTCGGAGACCCTGTCCCTCAC

CTGCGCTATCTATGGTGGGTCCTTCAGGGAGTACTACTGGAGCTGGATCCGCCAGCCCCAG

GGAAGGGGCTGGAGTGGATTGGGGAAATCTTTCATAGTGGAAGCACCAACTACAACCCGTCC

CTCAAGAGTCGAGTCAACATATCAGTAGACACGTCCAAGAACCAGTTCTCCCTGAAGCTGAC

CTCTGTGACCGCCGCGGACACGGCTGTGTATTACTGTGCGAGAGAGGAATTAGATGATTTTG

ATATCTGGGGCCAAGGGACAATGGTCACCGTCTCTTCAgcctccaccaagggcccatcggtc ttccccctggcgccctgctccaggagcacctccgagagcacagcggccctgggctgcctggt caaggactacttccccgaaccggtgacggtgtcgtggaactcaggcgctctgaccagcggcg tgcacaccttcccggctgtcctacagtcctcaggactctactccctcagcagcgtagtgacc gtgccctccagcaacttcggcacccagacctacacctgcaacgtagatcacaagcccagcaa caccaaggtggacaagacagttgagcgcaaatgttgtgtcgagtgcccaccgtgcccagcac cacctgtggcaggaccgtcagtcttcctcttccccccaaaacccaaggacaccctcatgatc tcccggacccctgaggtcacgtgcgtggtggtggacgtgagccacgaagaccccgaggtcca gttcaactggtacgtggacggcgtggaggtgcataatgccaagacaaagccacgggaggagc agttcaacagcacgttccgtgtggtcagcgtcctcaccgtcgtgcaccaggactggctgaac ggcaaggagtacaagtgcaaggtctccaacaaaggcctcccagcccccatcgagaaaaccat ctccaaaaccaaagggcagccccgagaaccacaggtgtacaccctgcccccatcccgggagg agatgaccaagaaccaggtcagcctgacctgcctggtcaaaggcttctacccagcgacatc gccgtggagtgggagagcaatgggcagccggagaacaactacaagaccacacctcccatgct ggactccgacggctccttcttcctctacagcaagctcaccgtggacaagagcaggtggcagc aggggaacgtcttctcatgctccgtgatgcatgaggctctgcacaaccactacacacagaag agcctctccctgtctccgggtaaa Derived protein sequence (by translation) of recombinant 9C8
IgG2 heavy chain (variable domain in uppercase)

SEQ ID NO: 24

QVQLQQWGAGLLKPSETLSLTCAIYGGSFREYYWSWIRQPPGKGLEWIGEIFHSGSTNYNPS

LKSRVNISVDTSKNQFSLKLTSVTAADTAVYYCAREELDDFDIWGQGTMVTVSSastkgpsv fplapcsrstsestaalgclvkdyfpepvtvswnsgaltsgvhtfpavlqssglyslssvvt vpssnfgtqtytcnvdhkpsntkvdktverkccvecppcpappvagpsvflfppkpkdtlmi srtpevtcvvvdvshedpevqfnwyvdgvevhnaktkpreeqfnstfrvvsvltvvhqdwln gkeykckvsnkglpapiektisktkgqprepqvytlppsreemtknqvsltclvkgfypsdi avewesngqpennykttppmldsdgsfflyskltvdksrwqqgnvfscsvmhealhnhytqk slslspgk DNA sequence of recombinant 9C8 Kappa light chain
(variable domain in uppercase)

SEQ ID NO: 25

GACATCCAGATGACCCAGTCTCCATCCTCACTGTCTGCATCTGTAGGAGACAGAGTCACCAT

CACTTGTCGGGCGAGTCAGGGTATTAGCAGCTGGTTAGCCTGGTATCAGCAGAAACCAGAGA

AAGCCCCTAAGTCCCTGATCTATGCTGCATCCAGTTTGCAAAGTGGGGTCCCATCAAGGTTC

AGCGGCAGTGGATCTGGGACAGATTTCACTCTCACCATCAGTAGCCTGCAGCCTGAAGATTT

TGCAACTTATTACTGCCAACAGTATAAAAGTTACCCTCGGACGTTCGGCCAAGGGACCAAGG

TGGAAATCAAAcgaactgtggctgcaccatctgtcttcatcttcccgccatctgatgagcag ttgaaatctggaactgcctctgttgtgtgcctgctgaataacttctatcccagagaggccaa agtacagtggaaggtggataacgccctccaatcgggtaactcccaggagagtgtcacagagc aggacagcaaggacagcacctacagcctcagcagcaccctgacgctgagcaaagcagactac gagaaacacaaagtctacgcctgcgaagtcacccatcagggcctgagctcgcccgtcacaaa gagcttcaacaggggagagtgt Derived protein sequence (by translation) of recombinant 9C8
Kappa light chain (variable domain in uppercase)

SEQ ID NO: 26

DIQMTQSPSSLSASVGDRVTITCRASQGISSWLAWYQQKPEKAPKSLIYAASSLQSGVPSRF

SGSGSGTDFTLTISSLQPEDFATYYCQQYKSYPRTFGQGTKVEIKrtvaapsvfifppsdeq lksgtasvvcllnnfypreakvqwkvdnalqsgnsqesvteqdskdstyslsstltlskady ekhkvyacevthqglsspvtksfnrgec

EXAMPLE 3

Mutagenesis of Anti-IL-6 Antibody

Amino acid substitution variants of the anti-IL-6 antibody 9C8 in the heavy chain variable domain were made at positions 24 (I24V), 30 (R30S), 31 (E31G), 52 (F52N), 68 (N68T), 83 (T83S) either singly or in combination both in the context of an IgG1 or an IgG2 format. Amino acid substitution variants of the anti-IL-6 antibody 9C8 in the light chain variable domain were made at 92 (K92N) both as an IgG1 or an IgG2 format. Antibodies having both a heavy chain variable domain and a light chain variable domain variant were made. Some of the various mutation combinations are shown in Table 6a and 6b. Mutagenesis, in the $V_H$ (I24V), $V_H$ (E31G), $V_H$ (N68T), and $V_H$ (T83S) regions of clone 9C8, was conducted with the primers listed in Table 4 (sense strands shown; targeted residue shown in bold) and the QuickChange kit (Stratagene) according to the manufacturer's instructions. The mutated variants were sequence verified and cloned into expression vectors by standard procedures.

TABLE 4

| Mutagenic primers (5' to 3') for 9C8 | | |
|---|---|---|
| 9C8_H_I24V | CCTCACCTGCGCTGTCTATGGTGGGTCC | SEQ ID NO: 57 |
| 9C8_H_E31G | GGGTCCTTCAGGGGGTACTACTGGAGCTG | SEQ ID NO: 58 |
| 9C8_H_N68T | CCTCAAGAGTCGAGTCACCATATCAGTAGACACG | SEQ ID NO: 59 |

TABLE 4 -continued

Mutagenic primers (5' to 3') for 9C8

9C8_H_T83S CTCCCTGAAGCTGAGCTCTGTGACCGCC SEQ ID NO: 60

DNA sequence of recombinant 9C8 IgG2 heavy chain (N68T, T83S)
heavy chain
SEQ ID NO: 27
CAGGTGCAGCTACAGCAGTGGGGCGCAGGACTGTTGAAGCCTTCGGAGACCCTGTCCCTCAC

CTGCGCTATCTATGGTGGGTCCTTCAGGGAGTACTACTGGAGCTGGATCCGCCAGCCCCCAG

GGAAGGGGCTGGAGTGGATTGGGGAAATCTTTCATAGTGGAAGCACCAACTACAACCCGTCC

CTCAAGAGTCGAGTCACCATATCAGTAGACACGTCCAAGAACCAGTTCTCCCTGAAGCTGAG

CTCTGTGACCGCCGCGGACACGGCTGTGTATTACTGTGCGAGAGAGGAATTAGATGATTTTG

ATATCTGGGGCCAAGGGACAATGGTCACCGTCTCCTCAgcctccaccaagggcccatcggtc ttccccctggcgccctgctccaggagcacctccgagagcacagcggccctgggctgcctggt caaggactacttccccgaaccggtgacggtgtcgtggaactcaggcgctctgaccagcggcg tgcacaccttcccggctgtcctacagtcctcaggactctactccctcagcagcgtagtgacc gtgccctccagcaacttcggcacccagacctacacctgcaacgtagatcacaagcccagcaa caccaaggtggacaagacagttgagcgcaaatgttgtgtcgagtgcccaccgtgcccagcac cacctgtggcaggaccgtcagtcttcctcttccccccaaaacccaaggacaccctcatgatc tcccggacccctgaggtcacgtgcgtggtggtggacgtgagccacgaagaccccgaggtcca gttcaactggtacgtggacggcgtggaggtgcataatgccaagacaaagccacgggaggagc agttcaacagcacgttccgtgtggtcagcgtcctcaccgtcgtgcaccaggactggctgaac ggcaaggagtacaagtgcaaggtctccaacaaaggcctcccagcccccatcgagaaaaccat ctccaaaaccaaagggcagccccgagaaccacaggtgtacaccctgcccccatcccgggagg agatgaccaagaaccaggtcagcctgacctgcctggtcaaaggcttctaccccagcgacatc gccgtggagtgggagagcaatgggcagccggagaacaactacaagaccacacctcccatgct ggactccgacggctccttcttcctctacagcaagctcaccgtggacaagagcaggtggcagc aggggaacgtcttctcatgctccgtgatgcatgaggctctgcacaaccactacacgcagaag agcctctccctgtctccgggtaaa Derived protein sequence (by translation) of recombinant 9C8
IgG2 heavy chain (N68T, T83S) heavy chain
SEQ ID NO: 28
QVQLQQWGAGLLKPSETLSLTCAIYGGSFREYYWSWIRQPPGKGLEWIGEIFHSGSTNYNPS LKSRVTISVDTSKNQFSLKLSSVTAADTAVYYCAREELDDFDIWGQGTMVTVSSastkgpsv fplapcsrstsestaalgclvkdyfpepvtvswnsgaltsgvhtfpavlqssglyslssvvt vpssnfgtqtytcnvdhkpsntkvdktverkccvecppcpappvagpsvflfppkpkdtlmi srtpevtcvvvdvshedpevqfnwyvdgvevhnaktkpreeqfnstfrvvsvltvvhqdwln gkeykckvsnkglpapiektisktkgqprepqvytlppsreemtknqvsltclvkgfypsdi avewesngqpennykttppmldsdgsfflyskltvdksrwqqgnvfscsvmhealhnhytqk slslspgk DNA sequence of recombinant 9C8 IgG1 heavy chain (N68T, T83S)
heavy chain

SEQ ID NO: 31
CAGGTGCAGCTACAGCAGTGGGGCGCAGGACTGTTGAAGCCTTCGGAGACCCTGTCCCTCAC

CTGCGCTATCTATGGTGGGTCCTTCAGGGAGTACTACTGGAGCTGGATCCGCCAGCCCCCAG

GGAAGGGGCTGGAGTGGATTGGGGAAATCTTTCATAGTGGAAGCACCAACTACAACCCGTCC

CTCAAGAGTCGAGTCACCATATCAGTAGACACGTCCAAGAACCAGTTCTCCCTGAAGCTGAG

CTCTGTGACCGCCGCGGACACGGCTGTGTATTACTGTGCGAGAGAGGAATTAGATGATTTTG

ATATCTGGGGCCAAGGGACAATGGTCACCGTCTCCTCAgcctccaccaagggcccatcggtc ttccccctggcaccctcctccaagagcacctctgggggcacagcggccctgggctgcctggt caaggactacttccccgaaccggtgacggtgtcgtggaactcaggcgccctgaccagcggcg tgcacaccttcccggctgtcctacagtcctcaggactctactccctcagcagcgtagtgacc gtgccctccagcagcttgggcacccagacctacatctgcaacgtgaatcacaagcccagcaa caccaaggtggacaagaaagttgagcccaaatcttgtgacaaaactcacacatgcccaccgt gcccagcacctgaactcctggggggaccgtcagtcttcctcttccccccaaaacccaaggac accctcatgatctcccggacccctgaggtcacatgcgtggtggtggacgtgagccacgaaga ccctgaggtcaagttcaactggtacgtggacggcgtggaggtgcataatgccaagacaaagc cgcgggaggagcagtacaacagcacgtaccgtgtggtcagcgtcctcaccgtcctgcaccag gactggctgaatggcaaggagtacaagtgcaaggtctccaacaaagccctcccagcccccat cgagaaaaccatctccaaagccaaagggcagccccgagaaccacaggtgtacaccctgcccc catcccgggaggagatgaccaagaaccaggtcagcctgacctgcctggtcaaaggcttctat cccagcgacatcgccgtggagtgggagagcaatgggcagccggagaacaactacaagaccac gcctcccgtgctggactccgacggctccttcttcctctatagcaagctcaccgtggacaaga gcaggtggcagcaggggaacgtcttctcatgctccgtgatgcatgaggctctgcacaaccac tacacgcagaagagcctctccctgtctccgggtaaa Protein sequence of recombinant 9C8 IgG1 heavy chain (N68T, T83S)
heavy chain
SEQ ID NO: 32
QVQLQQWGAGLLKPSETLSLTCAIYGGSFREYYWSWIRQPPGKGLEWIGEIFHSGSTNYNPS LKSRVTISVDTSKNQFSLKLSSVTAADTAVYYCAREELDDFDIWGQGTMVTVSSastkgpsv fplapsskstsggtaalgclvkdyfpepvtvswnsgaltsgvhtfpavlqssglyslssvvt vpssslgtqtyicnvnhkpsntkvdkkvepkscdkthtcppcpapellggpsvflfppkpkd tlmisrtpevtcvvvdvshedpevkfnwyvdgvevhnaktkpreeqynstyrvvsvltvlhq dwlngkeykckvsnkalpapiektiskakgqprepqvytlppsreemtknqvsltclvkgfy psdiavewesngqpennykttppvldsdgsfflyskltvdksrwqqgnvfscsvmhealhnh ytqkslslspgk Variable domain DNA sequence of recombinant 9C8 (E31G, N68T, T83S)
heavy chain
SEQ ID NO: 33
CAGGTGCAGCTACAGCAGTGGGGCGCAGGACTGTTGAAGCCTTCGGAGACCCTGTCCCTCAC

CTGCGCTATCTATGGTGGGTCCTTCAGGGGGTACTACTGGAGCTGGATCCGCCAGCCCCCAG

GGAAGGGGCTGGAGTGGATTGGGGAAATCTTTCATAGTGGAAGCACCAACTACAACCCGTCC

CTCAAGAGTCGAGTCACCATATCAGTAGACACGTCCAAGAACCAGTTCTCCCTGAAGCTGAG

CTCTGTGACCGCCGCGGACACGGCTGTGTATTACTGTGCGAGAGAGGAATTAGATGATTTTG

ATATCTGGGGCCAAGGGACAATGGTCACCGTCTCCTCA

Variable domain translated protein sequence of recombinant 9C8
(E31G, N68T, T83S) heavy chain

```
                                                      SEQ ID NO: 34
QVQLQQWGAGLLKPSETLSLTCAIYGGSFRGYYWSWIRQPPGKGLEWIGEIFHSGSTNYNPS

LKSRVTISVDTSKNQFSLKLSSVTAADTAVYYCAREELDDFDIWGQGTMVTVSS

Variable domain DNA sequence of recombinant 9C8 (I24V, N68T, T83S)
heavy chain
                                                      SEQ ID NO: 36
CAGGTGCAGCTACAGCAGTGGGGCGCAGGACTGTTGAAGCCTTCGGAGACCCTGTCCCTCAC

CTGCGCTGTCTATGGTGGGTCCTTCAGGGAGTACTACTGGAGCTGGATCCGCCAGCCCCAG

GGAAGGGGCTGGAGTGGATTGGGGAAATCTTTCATAGTGGAAGCACCAACTACAACCCGTCC

CTCAAGAGTCGAGTCACCATATCAGTAGACACGTCCAAGAACCAGTTCTCCCTGAAGCTGAG

CTCTGTGACCGCCGCGGACACGGCTGTGTATTACTGTGCGAGAGAGGAATTAGATGATTTTG

ATATCTGGGGCCAAGGGACAATGGTCACCGTCTCCTCA

Variable domain translated protein sequence of recombinant 9C8
(I24V, N68T, T83S) heavy chain
                                                      SEQ ID NO: 37
QVQLQQWGAGLLKPSETLSLTCAVYGGSFREYYWSWIRQPPGKGLEWIGEIFHSGSTNYNPS

LKSRVTISVDTSKNQFSLKLSSVTAADTAVYYCAREELDDFDIWGQGTMVTVSS
```

The CMV promoter containing expression vectors were transfected in 293 Freestyle (Invitrogen) cells according to the vendor's protocol. Supernatants from these cells were collected by centrifugation and purified by standard Protein-A affinity chromatography to isolate recombinant immunoglobulins. These proteins were then characterized by SDS-PAGE, light scatter, and spectrophotometrically.

The heavy and lght chains of the anti-IL-6 antibodies indicated in Table 5 were deposited under terms in accordance with the Budapest Treaty with the American Type Culture Collection (ATCC), 10801 University Blvd., Manassas, Va. 20110-2209. The heavy & lght chains have been assigned the following accession numbers:

TABLE 5

| Antibody | Clone Designation | ATCC Designation | Patent Deposit Designation | Deposit Date |
|---|---|---|---|---|
| 9C8 heavy chain IgG1 | E. coli; pCR2.1 TOPO 9C8H(WT) | UC25510 | PTA-8013 | Nov. 21, 2006 |
| 9C8 light chain IgG1 | E. coli; pCR2.1 TOPO 9C8L(WT) | UC25511 | PTA-8014 | Nov. 21, 2006 |
| 9C8 N68T, T83S IgG2 heavy chain | E. coli; pCR2.1 TOPO 9C8H(NT)hG2 | UC25512 | PTA-8015 | Nov. 21, 2006 |
| 9C8 N68T, T83S IgG2 light chain | E. coli; pCR2.1 TOPO 9C8L(wt)hk | UC25513 | PTA-8016 | Nov. 21, 2006 |
| 9C8 E31G, N68T, T83S variable region | E. coli; pCR2.1 TOPO 9C8H(ENT) | UC25514 | PTA-8017 | Nov. 21, 2006 |
| 9C8 I24V, N68T, T83S variable region | E. coli; pCR2.1 TOPO 9C8H(INT) | UC25515 | PTA-8018 | Nov. 21, 2006 |
| 9C8 N68T, T83S IgG1 heavy chain | E. coli; pCR2.1 TOPO 9C8H(NT)hG1 | UC25526 | PTA-8019 | Nov. 21, 2006 |

EXAMPLE 4

TF-1 Proliferation

Human cells, TF-1 cells, from American Type Culture Collection (ATCC) (Manassas, Va.), were obtained and maintained in RPMI-1640 medium containing 10% heat inactivated fetal bovine serum (FBS) (Invitrogen, Carlsbad, Calif.), with 2 ng/ml recombinant human GM-CSF. TF-1 cells were split to 1-2×10$^5$ for next day use. Prior to plating, the cells were washed three times with RPMI-1640, counted, and the volume adjusted with assay medium to yield 2×10$^5$ cells/ml. To each well, 50 µl of the washed cells was added and incubated overnight at 37° C. with 5% $CO_2$. All conditions were conducted in triplicate in 96-well tissue culture treated plates (Corning, Corning, N.Y.). To each well, either 25 ng/ml or 2.5 ng/ml IL-6 in a volume of 25 µl and test or control antibodies at various concentrations in a volume of 25 µl in sodium phosphate buffer (10 mM sodium phosphate and 150 mM sodium chloride, pH 7.4) to a final volume of 100 µl was added. Antibodies were tested alone and with human IL-6. The plates were incubated for 48 hours (hrs) at 37° C. with 5% $CO_2$. After 48 hours, 10 µl/well of 0.5 µCi $^3$H-thymidine (Amersham Biosciences, Piscataway, N.J.) was added and pulsed with the cells for 3 hrs. To detect the amount of incorporated thymidine, the cells were harvested onto pre-wet unifilter GF/C filterplates (Packard, Meriden, Conn.) and washed 10 times with water. The plates were allowed to dry overnight. Bottom seals were added to the filterplates. Next, 45 µl Microscint 20 (Packard, Meriden, Conn.) per well was added. After a top seal was added, the plates were counted in a Trilux microbeta counter (Wallac, Norton, Oh.) and data is reported as CPM (counts per minute). Tables 6a and 6b show the IC50s in the TF-1 proliferation assay of the 9C8 antibody and the various antibodies having amino acid substitutions. The results shown in Table 6a and Table 6b are from assays done on two separate occasions.

TABLE 6a

| Hc | Lc | Average IC50 (µg/ml) | Fold Difference |
|---|---|---|---|
| 9C8 | 9C8 | 0.0022 | 1.0 |
| 9C8 I24V | 9C8 | 0.0071 | 3.3 |
| 9C8 R30S | 9C8 | 0.0260 | 12.1 |
| 9C8 N68T | 9C8 | 0.0028 | 1.3 |
| 9C8 T83S | 9C8 | 0.0026 | 1.2 |
| 9C8 I24V, N68T, T83S | 9C8 | 0.0145 | 6.7 |
| 9C8 I24V, R30S, N68T, T83S | 9C8 | 0.2040 | 94.9 |
| 9C8 E31G | 9C8 | 0.0051 | 2.4 |

TABLE 6a-continued

| Hc | Lc | Average IC50 (µg/ml) | Fold Difference |
|---|---|---|---|
| 9C8 F52N | 9C8 | 1.3850 | 644.2 |
| 9C8 | 9C8 K92N | 0.0120 | 5.6 |

TABLE 6b

| Hc | Lc | Average IC50 (µg/ml) | Fold Difference |
|---|---|---|---|
| 9C8 | 9C8 | 0.0031 | 1.4 |
| 9C8 N68T, T83S | 9C8 | 0.0030 | 1.4 |
| 9C8 E31G, N68T, T83S | 9C8 | 0.0083 | 3.9 |
| 9C8 I24V, E31G, N68T, T83S | 9C8 | 0.0528 | 24.5 |
| 9C8 N68T, T83S | 9C8 9C8 K92N | 0.0186 | 8.6 |
| 9C8 E31G, N68T T83S | 9C8 K92N | 0.1015 | 47.2 |
| 9C8 I24V, E31G N68T, T83S | 9C8 K92N | 0.9670 | 449.9 |

Hc = heavy chain,
Lc = light chain

EXAMPLE 5

C-Reactive Protein from LPS-Monkey Study

The in-vivo portion of this study was conducted by Charles River Laboratories Preclinical Services at their Worcester, Mass. Test Facility. Briefly, the study consisted of fifteen male cynomolgus monkeys (five groups; 3 monkeys/group). On Day 1 animals in group 1 received vehicle; animals in Groups 2 and 3 received the antibody 9C8 N68T T83S $IgG_1$ at doses of 0.5 and 5 mg/kg, respectively; and animals in Groups 4 and 5 received 9C8 N68T T83S $IgG_2$ at doses of 0.5 and 5 mg/kg, respectively. All treatments were administered by IV bolus injection at dose volumes of 1 mL/kg each. Approximately 2 hours after treatment, all animals were challenged with 10 µg/kg bacterial lipopolysaccharide (LPS) at a volume of 1 mL/kg by slow IV bolus injection. On Day 1 blood was collected from a peripheral vessel at baseline (prior to treatment); immediately following treatment; 2 hours post-treatment (immediately prior to LPS administration); and at 30 minutes and 1, 2, 3, 4, 6, 8, and 22 hours after LPS challenge. Blood samples were also collected on Days 3, 4, 5, 6 and 7. Whole blood samples were processed for serum and serum samples were stored frozen. C-Reactive Protein (CRP) was measured using a human Vascular Injury Panel II Multi-Spot® Assay Kit from Meso Scale Discovery (MSD®), Gaithersburg, Md. Assays were performed as outlined in published kit instructions from MSD. FIG. 2 shows the total serum CRP for the 9C8 N68T T83S $IgG_2$ antibody.

EXAMPLE 6 pSTAT3 Assay by Flow Cytometry

In vitro assays were conducted in human whole blood and human peripheral blood mononuclear cells (PBMCs) stimulated with recombinant human IL-6 (rhIL-6) to measure phosphorylated STAT3 (pSTAT3) levels in the presence of anti-IL-6 antibodies.

Whole Blood Assay

Freshly collected heparinized human whole blood was incubated with anti-IL-6 antibody or vehicle control (final volume 300 µL in 15 mL polypropylene tube) for 15 minutes at 37° C. Samples were stimulated with recombinant human (rh) IL-6 for a final concentration of 25 ng/mL and incubated for 10 minutes at 37° C. Red blood cells (RBCs) were then lysed with 4 mL RBC Lysing Buffer (Sigma), and samples were mixed gently for 10 minutes at 37° C. Samples were spun at 400×g for 5 min to pellet cells. Supernatants were removed. Two milliliters of wash buffer (4% BSA in PBS, Gibco) were added to each tube, and then samples were spun at 400×g for 5 min to pellet cells. Supernatants were removed, and cell pellets were resuspended in 200 µL of preheated (37° C.) permeabilization buffer (2% formaldehyde in PBS, Polysciences, Inc.) and incubated at 37° C. for 10 minutes. Three milliliters of ice cold MeOH was added to each sample to fix the cells. Samples were mixed and placed on ice for at least 30 min. Samples were spun (400×g for 5 min.) and supernatants were removed. Pellets were washed once with wash buffer. Cell pellets were then stained with anti-phosphorylated STAT3 (Y705) antibody conjugated to Alexa Fluor 488 (BD Pharmingen) diluted in wash buffer, final volume 100 µL. Samples were incubated on ice for 30 minutes then washed 2× in wash buffer. Final cell pellets were resuspended in 400 µL IF Buffer (Hank's Buffered Saline Solution, 2% Fetal Calf Serum, 10 mM Hepes, 0.2% Sodium Azide, Gibco). A FACSCalibur instrument using CellQuest software (BD Biosciences) was used to collect and analyze data. Table 7 shows the pSTAT3 levels in the presence of anti-IL-6 antibodies as measured in human whole blood.

TABLE 7

| Anti IL-6 Antibody | IL-6 Conc ng/ml | WB IC50 µg/ml | Assay # |
|---|---|---|---|
| 9C8 | 25 | 0.487 | 1 |
|  | 25 | 0.432 | 2 |
|  | 25 | 0.482 | 3 |
| I24V, N68T, T83S | 25 | 0.420 | 1 |
|  | 25 | 0.527 | 2 |
|  | 25 | 0.749 | 3 |
| E31G, N68T, T83S | 25 | 0.626 | 1 |
|  | 25 | 0.714 | 2 |
|  | 25 | 0.968 | 3 |
| I24V, E31G, N68T, T83S | 25 | 0.364 | 1 |
|  | 25 | 0.603 | 2 |
|  | 25 | 0.821 | 3 |

PBMC Assay

Peripheral blood mononuclear cells (PBMCs) were isolated from freshly collected heparinized human whole blood using Accuspin System-Histopaque 1077 columns according to manufacture's protocol (Sigma-Aldrich A7054) and placed in (0.1% penicillin streptomycin in Macrophage SFM Media, Gibco). Approximately $2 \times 10^6$ PBMCs were incubated with anti-IL-6 antibody or vehicle control (final vol. 300 µL) for 15 min. at 37° C. PBMCs were stimulated with rhIL-6 for a final concentration of 25 ng/mL and incubated for 10 min. at 37° C. Samples were spun at 400×g for 5 min to pellet cells. Supernatants were removed. Two mL wash buffer (4% BSA in PBS) was added to each sample. Samples were spun at 400×g 5 min to pellet cells. Supernatants were removed and cell pellets were resuspended in 200 uL of preheated (37° C.) permeabilization buffer (2% formaldehyde in PBS, Polysciences, Inc.) and incubated at 37° C. for 10 min. Three milliliters of ice cold MeOH was added to each sample to fix the cells. Samples were mixed and kept on ice for at least 30 min. Samples were spun at 400×g for 5 min. and supernatants were removed. Cell pellets were washed once with wash buffer then stained and analyzed as described in the whole blood assay. Table 8 shows the pSTAT3 levels in the presence of anti-IL-6 antibodies as measured in human peripheral blood mononuclear cells.

TABLE 8

| Anti IL-6 Antibody | IL-6 conc. ng/ml | PBMC IC50 μg/ml |
|---|---|---|
| 9C8 | 25 | 0.210 |
| R&D MAB2061 | 25 | 0.580 |

EXAMPLE 7

Binding Affinity

Preparation of BIAcore Chips

The anti-IL-6 antibody 9C8 N68T T83S IgG2 was immobilized onto BIAcore CM5 chips (GE Biosciences—formerly BIAcore Inc, Piscataway, N.J.) by amine coupling to carboxymethylcellulose (CM) attached to the dextran matrix of the chip as described by Löfås & Johnsson (*J. Chem. Soc. Chem. Commun.* (1990); 21:pp 1526-1528). The chip was pretreated with 1 M NaCl and 50 mM NaOH prior to coupling. Amine coupling was accomplished by combining EDC (1-ethyl-3-(3-dimethylaminopropyl)carbodiimide and NHS (N-hydroxysuccinimide) and passing across the chip to activate the CM groups. The ligand in 10 mM acetate buffer pH 5 was passed across the chip surface and covalently bound to the activated CM group. The remaining active CM groups on the chip surface were quenched by passing 1M ethanolamine pH 8.5 across the chip. The EDC, NHS, and ethanolamine were obtained as part of the Amine Coupling kit obtained from GE Biosciences. Coupling was performed using the automated Surface Preparation Wizard included with the Bia-Control Software V3.2.

Determination of Binding Affinity

All SPR measurements were performed on a BIAcore 3000 instrument (GE Biosciences, Piscataway, N.J.). BIAcore Software—BIAcore 3000 Control Software V3.2 was used for the operation and control of the BIAcore 3000 instrument. BiaEvaluation Software V4.1 was used for the analysis of SPR data from the BIAcore 3000 instrument and data was plotted using Graph Pad Prism Software Version 5. The binding affinity of IL-6 to monoclonal antibodies (mAb) was measured in HBS-EP buffer (10 mM HEPES, 150 mM NaCl, 3.4 mM EDTA, 0.005% P20) at 25° C. The flow rate for the affinity study was 40 uL/minute to minimize mass transport effects (Myszka, D. G., et al., Biophysical chemistry. 64, 127-137, 1997). Human IgG$_K$ was used as the ligand for the construction of the reference channel of the chip. Analyte (rhIL-6; R&D Systems, Minneapolis, Minn., 206-IL) binding to the immobilized ligand (9C8 N68T T83S IgG$_2$) was measured in duplicate and the concentration of the IL-6 ranged from 0 to 25 nM. Injection time for IL-6 was 6 minutes and dissociation time was 25 minutes. The surface was regenerated between cycles by 10 mM glycine pH 1.7 for 30 seconds at a flow rate of 30 uL/min. The regeneration conditions were established to be optimal after a regeneration study (data not shown). Data was analyzed by using the Kinetics Wizard and the manual fitting programs that are both included with the BiaEvaluation Software V4.1 using a 1:1 Langmuir model (Karlson R & Fält A., *J. Immunol. Methods.* 200: pp 121-133, 1997). The anti IL-6 antibody 9C8 N68T T83S IgG$_2$ was shown to have $k_a$=9.95E+05 (Ms)$^{-1}$, a $k_d$=1.34E−04 s$^{-1}$, and a $K_D$=1.35E−10 M or 135 pM.

| SUMMARY OF SEQUENCE LISTING (sequences are amino acid sequences except those indicated by 'n.a.' for nucleic acid) ||
|---|---|
| SEQ ID NO: | SEQUENCE |
| 1 | heavy 9C8 IgG1 n.a. |
| 2 | V$_H$ 9C8 n.a. |
| 3 | heavy 9C8 IgG1 |
| 4 | V$_H$ 9C8 |
| 5 | V$_H$ CDR1 9C8 |
| 6 | V$_H$ CDR2 9C8 |
| 7 | V$_H$ CDR3 9C8 |
| 8 | V$_H$ FR1 9C8 |
| 9 | V$_H$ FR2 9C8 |
| 10 | V$_H$ FR3 9C8 |
| 11 | V$_H$ FR4 9C8 |
| 12 | light 9C8 IgG1 n.a. |
| 13 | V$_L$ 9C8 n.a. |
| 14 | light 9C8 IgG1 |
| 15 | V$_L$ 9C8 |
| 16 | V$_L$ CDR1 9C8 |
| 17 | V$_L$ CDR2 9C8 |
| 18 | V$_L$ CDR3 9C8 |
| 19 | V$_L$ FR1 9C8 |
| 20 | V$_L$ FR2 9C8 |
| 21 | V$_L$ FR3 9C8 |
| 22 | V$_L$ FR4 9C8 |
| 23 | heavy 9C8 IgG2 n.a. |
| 24 | heavy 9C8 IgG2 |
| 25 | light 9C8 IgG2 n.a. |
| 26 | light 9C8 IgG2 |
| 27 | heavy 9C8 N68T T83S IgG2 n.a. |
| 28 | heavy 9C8 N68T T83S IgG2 |
| 29 | V$_H$ 9C8 N68T T83S |
| 30 | V$_H$ FR3 9C8 N68T T83S |
| 31 | heavy 9C8 N68T T83S IgG1 n.a. |
| 32 | heavy 9C8 N68T T83S IgG1 |
| 33 | V$_H$ 9C8 E31G N68T T83S n.a. |
| 34 | V$_H$ 9C8 E31G N68T T83S |
| 35 | V$_H$ CDR1 9C8 E31G N68T T83S |
| 36 | V$_H$ 9C8 I24V N68T T83S n.a. |
| 37 | V$_H$ 9C8 I24V N68T T83S |
| 38 | V$_H$ FR1 9C8 I24V N68T T83S |
| 39 | V$_H$ 22B5 n.a. |
| 40 | V$_H$ 22B5 |
| 41 | V$_H$ CDR3 22B5 |
| 42 | V$_L$ 22B5 n.a. |
| 43 | V$_L$ 22B5 |
| 44 | Consensus 1 CDR3 |
| 45 | Consensus 2 CDR3 |

We claim:

1. A method for treating or alleviating the symptoms of an IL-6 mediated disorder in a subject in need thereof, comprising administering to said subject an anti-IL-6 antibody or an antigen-binding portion thereof, wherein the antibody comprises a heavy chain and a light chain, and wherein
   (a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
   (b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

2. The method of claim 1, wherein the monoclonal antibody or antigen-binding portion comprises
   heavy chain FR1, FR2, FR3, and FR4 comprising the amino acid sequences of (1) SEQ ID NOs: 8 or 38, (2) SEQ ID NO: 9, (3) SEQ ID NO: 10 or 30, and (4) SEQ ID NO: 11, respectively; and
   light chain FR1, FR2, FR3, and FR4 comprising the amino acid sequences of (1) SEQ ID NO: 19, (2) SEQ ID NO: 20, (3) SEQ ID NO: 21, and (4) SEQ ID NO: 22, respectively.

3. The method of claim 1, wherein the monoclonal antibody or antigen-binding portion comprises a $V_H$ domain and a $V_L$ domain comprising the amino acid sequences of:
   (a) SEQ ID NOs: 4 and 15, respectively;
   (b) SEQ ID NOs: 29 and 15, respectively;
   (c) SEQ ID NOs: 37 and 15, respectively;
   (d) the $V_H$ domain encoded by the cDNA insert of the plasmid deposited with the ATCC under accession number PTA-8013 and the $V_L$ domain encoded by the cDNA insert of the plasmid deposited with the ATCC under accession number PTA-8014, respectively;
   (e) the $V_H$ domain encoded by the cDNA insert of the plasmid deposited with the ATCC under accession number PTA-8015 and the $V_L$ domain encoded by the cDNA insert of the plasmid deposited with the ATCC under accession number PTA-8016, respectively; or
   (f) the $V_H$ domain encoded by the cDNA insert of the plasmid deposited with the ATCC under accession number PTA-8019 and the $V_L$ domain encoded by the cDNA insert of the plasmid deposited with the ATCC under accession number PTA-8014, respectively.

4. The method of claim 1, wherein the heavy and light chains comprise the amino acid sequences of:
   (a) SEQ ID NOs: 3 and 14, respectively;
   (b) SEQ ID NOs: 24 and 26, respectively;
   (c) SEQ ID NOs: 32 and 14, respectively;
   (d) SEQ ID NOs: 28 and 26, respectively;
   (e) the heavy chain encoded by the cDNA insert of the plasmid deposited with the ATCC under accession number PTA-8013 and the light chain encoded by the cDNA insert of the plasmid deposited with the ATCC under accession number PTA-8014, respectively;
   (f) the heavy chain encoded by the cDNA insert of the plasmid deposited with the ATCC under accession number PTA-8015 and the light chain encoded by the cDNA insert of the plasmid deposited with the ATCC under accession number PTA-8016, respectively; or
   (g) the heavy chain encoded by the cDNA insert of the plasmid deposited with the ATCC under accession number PTA-8019 and the light chain encoded by the cDNA insert of the plasmid deposited with the ATCC under accession number PTA-8014, respectively.

5. A method for treating or alleviating the symptoms of an IL-6 mediated disorder in a subject in need thereof, comprising administering to said subject a pharmaceutical composition comprising an anti-IL-6 monoclonal antibody or an antigen-binding portion thereof, and a pharmaceutically acceptable carrier, wherein the antibody comprises a heavy chain and a light chain, and wherein
   (a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
   (b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

6. The method of claim 1, wherein the IL-6 mediated disorder is selected from the group consisting of an inflammatory disorder, an allergic disorder, an autoimmune disorder, a graft rejection disorder, atherosclerosis, osteoporosis, neuropathic pain, type 2 diabetes mellitus, chronic obstructive pulmonary disease, multiple sclerosis, sepsis, cancer, Castleman's disease, and a fibrotic condition.

7. The method of claim 6 wherein said inflammatory disorder is selected from the group consisting of rheumatoid arthritis, juvenile idiopathic arthritis, osteoarthritis, systemic lupus erythematosus, ankylosing spondylitis, psoriasis, Crohn's disease, and adult-onset Still's disease.

8. The method of claim 6 wherein said fibrotic condition is selected from the group consisting of liver fibrosis, renal fibrosis, and pulmonary fibrosis.

9. The method of claim 6 wherein said cancer is multiple myeloma or renal cell carcinoma.

10. The method of claim 5, wherein the monoclonal antibody or antigen-binding portion comprises
    heavy chain FR1, FR2, FR3, and FR4 comprising the amino acid sequences of (1) SEQ ID NOs: 8 or 38, (2)

SEQ ID NO: 9, (3) SEQ ID NO: 10 or 30, and (4) SEQ ID NO: 11, respectively; and light chain FR1, FR2, FR3, and FR4 comprising the amino acid sequences of (1) SEQ ID NO: 19, (2) SEQ ID NO: 20, (3) SEQ ID NO: 21, and (4) SEQ ID NO: 22, respectively.

11. The method of claim 5, wherein the monoclonal antibody or antigen-binding portion comprises a $V_H$ domain and a $V_L$ domain comprising the amino acid sequences of:
   (a) SEQ ID NOs: 4 and 15, respectively;
   (b) SEQ ID NOs: 29 and 15, respectively;
   (c) SEQ ID NOs: 37 and 15, respectively;
   (d) the $V_H$ domain encoded by the cDNA insert of the plasmid deposited with the ATCC under accession number PTA-8013 and the $V_L$ domain encoded by the cDNA insert of the plasmid deposited with the ATCC under accession number PTA-8014, respectively;
   (e) the $V_H$ domain encoded by the cDNA insert of the plasmid deposited with the ATCC under accession number PTA-8015 and the $V_L$ domain encoded by the cDNA insert of the plasmid deposited with the ATCC under accession number PTA-8016, respectively; or
   (f) the $V_H$ domain encoded by the cDNA insert of the plasmid deposited with the ATCC under accession number PTA-8019 and the $V_L$ domain encoded by the cDNA insert of the plasmid deposited with the ATCC under accession number PTA-8014, respectively.

12. The method of claim 6, wherein the heavy and light chains comprise:
   (a) SEQ ID NOs: 3 and 14, respectively;
   (b) SEQ ID NOs: 24 and 26, respectively;
   (c) SEQ ID NOs: 32 and 14, respectively;
   (d) SEQ ID NOs: 28 and 26, respectively;
   (e) the heavy chain encoded by the cDNA insert of the plasmid deposited with the ATCC under accession number PTA-8013 and the light chain encoded by the cDNA insert of the plasmid deposited with the ATCC under accession number PTA-8014, respectively;
   (f) the heavy chain encoded by the cDNA insert of the plasmid deposited with the ATCC under accession number PTA-8015 and the light chain encoded by the cDNA insert of the plasmid deposited with the ATCC under accession number PTA-8016, respectively; or
   (g) the heavy chain encoded by the cDNA insert of the plasmid deposited with the ATCC under accession number PTA-8019 and the light chain encoded by the cDNA insert of the plasmid deposited with the ATCC under accession number PTA-8014, respectively.

13. The method of claim 6, wherein the IL-6 mediated disorder is selected from the group consisting of an inflammatory disorder, an allergic disorder, an autoimmune disorder, a graft rejection disorder, atherosclerosis, osteoporosis, neuropathic pain, type 2 diabetes mellitus, chronic obstructive pulmonary disease, multiple sclerosis, sepsis, cancer, Castleman's disease, and a fibrotic condition.

14. The method of claim 13 wherein said inflammatory disorder is selected from the group consisting of rheumatoid arthritis, juvenile idiopathic arthritis, osteoarthritis, systemic lupus erythematosus, ankylosing spondylitis, psoriasis, Crohn's disease, and adult-onset Still's disease.

15. The method of claim 13 wherein said fibrotic condition is selected from the group consisting of liver fibrosis, renal fibrosis, and pulmonary fibrosis.

16. The method of claim 13 wherein said cancer is multiple myeloma or renal cell carcinoma.

17. A method for treating or alleviating the symptoms of an IL-6 mediated disorder in a subject in need thereof, comprising administering to said subject an anti-IL-6 antibody comprising a heavy chain amino acid sequence of SEQ ID NO: 28 and a light chain amino acid sequence of SEQ ID NO: 26.

18. The method of claim 17, wherein the IL-6 mediated disorder is selected from the group consisting of an inflammatory disorder, an allergic disorder, an autoimmune disorder, a graft rejection disorder, atherosclerosis, osteoporosis, neuropathic pain, type 2 diabetes mellitus, chronic obstructive pulmonary disease, multiple sclerosis, sepsis, cancer, Castleman's disease, and a fibrotic condition.

19. The method of claim 18 wherein said inflammatory disorder is selected from the group consisting of rheumatoid arthritis, juvenile idiopathic arthritis, osteoarthritis, systemic lupus erythematosus, ankylosing spondylitis, psoriasis, Crohn's disease, and adult-onset Still's disease.

20. The method of claim 18 wherein said fibrotic condition is selected from the group consisting of liver fibrosis, renal fibrosis, and pulmonary fibrosis.

21. The method of claim 18 wherein said cancer is multiple myeloma or renal cell carcinoma.

22. A method for treating or alleviating the symptoms of Crohn's disease in a subject in need thereof, comprising administering to said subject an anti-IL-6 antibody or an antigen-binding portion thereof, wherein the antibody comprises a heavy chain and a light chain, and wherein
   (a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
   (b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

23. A method for treating or alleviating the symptoms of Crohn's disease in a subject in need thereof, comprising administering to said subject a pharmaceutical composition comprising an anti-IL-6 antibody or an antigen-binding portion thereof, wherein the antibody comprises a heavy chain and a light chain, and wherein
   (a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
   (b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

24. The method of claim 22 or 23, wherein the monoclonal antibody or antigen-binding portion comprises
   heavy chain FR1, FR2, FR3, and FR4 comprising the amino acid sequences of (1) SEQ ID NOs: 8 or 38, (2) SEQ ID NO: 9, (3) SEQ ID NO: 10 or 30, and (4) SEQ ID NO: 11, respectively; and
   light chain FR1, FR2, FR3, and FR4 comprising the amino acid sequences of (1) SEQ ID NO: 19, (2) SEQ ID NO: 20, (3) SEQ ID NO: 21, and (4) SEQ ID NO: 22, respectively.

25. The method of claim 22 or 23, wherein the monoclonal antibody or antigen-binding portion comprises a $V_H$ domain and a $V_L$ domain comprising the amino acid sequences of:
(a) SEQ ID NOs: 4 and 15, respectively;
(b) SEQ ID NOs: 29 and 15, respectively;
(c) SEQ ID NOs: 37 and 15, respectively;
(d) the $V_H$ domain encoded by the cDNA insert of the plasmid deposited with the ATCC under accession number PTA-8013 and the $V_L$ domain encoded by the cDNA insert of the plasmid deposited with the ATCC under accession number PTA-8014, respectively;
(e) the $V_H$ domain encoded by the cDNA insert of the plasmid deposited with the ATCC under accession number PTA-8015 and the $V_L$ domain encoded by the cDNA insert of the plasmid deposited with the ATCC under accession number PTA-8016, respectively; or
(f) the $V_H$ domain encoded by the cDNA insert of the plasmid deposited with the ATCC under accession number PTA-8019 and the $V_L$ domain encoded by the cDNA insert of the plasmid deposited with the ATCC under accession number PTA-8014, respectively.

26. The method of claim 22 or 23, wherein the heavy and light chains comprise the amino acid sequences of:
(a) SEQ ID NOs: 3 and 14, respectively;
(b) SEQ ID NOs: 24 and 26, respectively;
(c) SEQ ID NOs: 32 and 14, respectively;
(d) SEQ ID NOs: 28 and 26, respectively;
(e) the heavy chain encoded by the cDNA insert of the plasmid deposited with the ATCC under accession number PTA-8013 and the light chain encoded by the cDNA insert of the plasmid deposited with the ATCC under accession number PTA-8014, respectively;
(f) the heavy chain encoded by the cDNA insert of the plasmid deposited with the ATCC under accession number PTA-8015 and the light chain encoded by the cDNA insert of the plasmid deposited with the ATCC under accession number PTA-8016, respectively; or
(g) the heavy chain encoded by the cDNA insert of the plasmid deposited with the ATCC under accession number PTA-8019 and the light chain encoded by the cDNA insert of the plasmid deposited with the ATCC under accession number PTA-8014, respectively.

27. A method for treating or alleviating the symptoms of Crohn's disease in a subject in need thereof, comprising administering to said subject an anti-IL-6 antibody comprising a heavy chain amino acid sequence of SEQ ID NO: 28 and a light chain amino acid sequence of SEQ ID NO: 26.

28. A method for treating or alleviating the symptoms of systemic lupus erythematosus in a subject in need thereof, comprising administering to said subject an anti-IL-6 antibody or an antigen-binding portion thereof, and a pharmaceutically acceptable carrier, wherein the antibody comprises a heavy chain and a light chain, and wherein
(a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
(b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

29. A method for treating or alleviating the symptoms of systemic lupus erythematosus in a subject in need thereof, comprising administering to said subject a pharmaceutical composition comprising an anti-IL-6 monoclonal antibody or an antigen-binding portion thereof, and a pharmaceutically acceptable carrier, wherein the antibody comprises a heavy chain and a light chain, and wherein
(a) the heavy chain comprises the CDR1, CDR2 and CDR3 of the $V_H$ domain encoded by the cDNA insert of the plasmid deposited with the ATCC under accession number PTA-8015 and the light chain comprises the CDR1, CDR2 and CDR3 of the $V_L$ domain encoded by the cDNA insert of the plasmid deposited with the ATCC under accession number PTA-8016; or
(b) the heavy chain CDR1, CDR2, and CDR3 comprise the amino acid sequences of SEQ ID NOs: 5, 6, and 7, respectively, and the light chain CDR1, CDR2, and CDR3 comprise the amino acid sequences of SEQ ID NOs: 16, 17, and 18, respectively.

30. The method of claim 28 or 29, wherein the monoclonal antibody or antigen-binding portion comprises
heavy chain FR1, FR2, FR3, and FR4 comprising the amino acid sequences of (1) SEQ ID NOs: 8 or 38, (2) SEQ ID NO: 9, (3) SEQ ID NO: 10 or 30, and (4) SEQ ID NO: 11, respectively; and
light chain FR1, FR2, FR3, and FR4 comprising the amino acid sequences of (1) SEQ ID NO: 19, (2) SEQ ID NO: 20, (3) SEQ ID NO: 21, and (4) SEQ ID NO: 22, respectively.

31. The method of claim 28 or 29, wherein the monoclonal antibody or antigen-binding portion comprises a $V_H$ domain and a $V_L$ domain comprising the amino acid sequences of:
(a) SEQ ID NOs: 4 and 15, respectively;
(b) SEQ ID NOs: 29 and 15, respectively;
(c) SEQ ID NOs: 37 and 15, respectively;
(d) the $V_H$ domain encoded by the cDNA insert of the plasmid deposited with the ATCC under accession number PTA-8013 and the $V_L$ domain encoded by the cDNA insert of the plasmid deposited with the ATCC under accession number PTA-8014, respectively;
(e) the $V_H$ domain encoded by the cDNA insert of the plasmid deposited with the ATCC under accession number PTA-8015 and the $V_L$ domain encoded by the cDNA insert of the plasmid deposited with the ATCC under accession number PTA-8016, respectively; or
(f) the $V_H$ domain encoded by the cDNA insert of the plasmid deposited with the ATCC under accession number PTA-8019 and the $V_L$ domain encoded by the cDNA insert of the plasmid deposited with the ATCC under accession number PTA-8014, respectively.

32. The method of claim 28 or 29, wherein the heavy and light chains comprise the amino acid sequences of:
(a) SEQ ID NOs: 3 and 14, respectively;
(b) SEQ ID NOs: 24 and 26, respectively;
(c) SEQ ID NOs: 32 and 14, respectively;
(d) SEQ ID NOs: 28 and 26, respectively;
(e) the heavy chain encoded by the cDNA insert of the plasmid deposited with the ATCC under accession number PTA-8013 and the light chain encoded by the cDNA insert of the plasmid deposited with the ATCC under accession number PTA-8014, respectively;
(f) the heavy chain encoded by the cDNA insert of the plasmid deposited with the ATCC under accession number PTA-8015 and the light chain encoded by the cDNA insert of the plasmid deposited with the ATCC under accession number PTA-8016, respectively; or
(g) the heavy chain encoded by the cDNA insert of the plasmid deposited with the ATCC under accession number PTA-8019 and the light chain encoded by the cDNA insert of the plasmid deposited with the ATCC under accession number PTA-8014, respectively.

33. A method for treating or alleviating the symptoms of systemic lupus erythematosus in a subject in need thereof, comprising administering to said subject an anti-IL-6 antibody comprising a heavy chain amino acid sequence of SEQ ID NO: 28 and a light chain amino acid sequence of SEQ ID NO: 26.

* * * * *